(12) United States Patent
Cheung et al.

(10) Patent No.: US 9,315,585 B2
(45) Date of Patent: Apr. 19, 2016

(54) ANTI-GD2 ANTIBODIES

(75) Inventors: Nai-Kong Cheung, New York, NY (US); Mahiuddin Ahmed, Verona, NJ (US); Hong Xu, New York, NY (US)

(73) Assignee: Memorial Sloan Kettering Cancer Center, New York, NY (US)

( * ) Notice: Subject to any disclaimer, the term of this patent is extended or adjusted under 35 U.S.C. 154(b) by 0 days.

(21) Appl. No.: 13/702,319

(22) PCT Filed: Jun. 20, 2011

(86) PCT No.: PCT/US2011/041082
§ 371 (c)(1),
(2), (4) Date: May 13, 2013

(87) PCT Pub. No.: WO2011/160119
PCT Pub. Date: Dec. 22, 2011

(65) Prior Publication Data
US 2013/0216528 A1    Aug. 22, 2013

Related U.S. Application Data

(60) Provisional application No. 61/397,920, filed on Jun. 19, 2010.

(51) Int. Cl.
| | | |
|---|---|---|
| *A61K 39/395* | (2006.01) | |
| *C07K 16/46* | (2006.01) | |
| *C07K 16/30* | (2006.01) | |
| *A61K 39/00* | (2006.01) | |

(52) U.S. Cl.
CPC ............ *C07K 16/468* (2013.01); *C07K 16/3084* (2013.01); *C07K 16/46* (2013.01); *C07K 16/461* (2013.01); *A61K 2039/505* (2013.01); *C07K 2317/24* (2013.01); *C07K 2317/567* (2013.01); *C07K 2317/72* (2013.01); *C07K 2317/73* (2013.01); *C07K 2317/732* (2013.01); *C07K 2317/734* (2013.01); *C07K 2317/92* (2013.01)

(58) Field of Classification Search
None
See application file for complete search history.

(56) References Cited

U.S. PATENT DOCUMENTS

| | | | | |
|---|---|---|---|---|
| 5,530,101 | A * | 6/1996 | Queen et al. | 530/387.3 |
| 6,884,879 | B1 * | 4/2005 | Baca et al. | 536/23.53 |
| 7,423,114 | B2 * | 9/2008 | Gagnon et al. | 530/327 |
| 2003/0147881 | A1 | 8/2003 | Cheung et al. | |
| 2004/0220084 | A1 | 11/2004 | Sandhu | |
| 2004/0259771 | A1 | 12/2004 | Stahl et al. | |
| 2005/0002930 | A1 | 1/2005 | Johnson et al. | |
| 2005/0101770 | A1 | 5/2005 | Presta | |
| 2009/0004674 | A1 * | 1/2009 | Sims et al. | 435/7.2 |

FOREIGN PATENT DOCUMENTS

| | | | |
|---|---|---|---|
| JP | 2002-532079 | A | 10/2002 |
| JP | 2005-511706 | A | 4/2005 |
| JP | 2008-505174 | A | 2/2008 |
| JP | 2009-506790 | A | 2/2009 |
| WO | 91/09967 | * | 7/1991 |
| WO | WO-92/18629 | A1 | 10/1992 |
| WO | WO-00/35483 | A1 | 6/2000 |
| WO | WO-03/048321 | A2 | 6/2003 |
| WO | WO-2006/019447 | A1 | 2/2006 |
| WO | WO-2007/030642 | A2 | 3/2007 |
| WO | WO-2010/017598 | A1 | 2/2010 |

OTHER PUBLICATIONS

Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205,.*
Jurcic et al Cancer Chemotherapy and Biological Response Modifiers Annual 17, Elseviers Science 1997, Chapter 10 pp. 195-216.*
Sadelain et al Cancer Discovery vol. 3 p. 388 (2013).*
Rossig et al Int. J. Cancer vol. 94 p. 228 (2001).*
Basu et al., "Phase I Study of Anti-GD2 Humanized 3F8 (hu3F8) Monoclonal Antibody (MAb) in Patients with Relapsed or Refractory Neuroblasoma (NB) or Other GD2-Positive Solid Tumors," Advances in Neuroblastoma Research, Information Book, Abstract, p. 242 (2014).
Bindon et al., "Human Monoclonal IgG Isotypes Differ in Complement Activating Function at the Level of C4 as well as C1q" J. Exp. Med. 168: 127-142 (1988).
Cheung et al., "Ganglioside $G_{D2}$ Specific Monoclonal Antigody 3F8: A Phase I Study in Patients With Neuroblastoma and Malignant Melanoma," Journal of Clinical Oncology 5(9): 1430-1440 (1987).

(Continued)

*Primary Examiner* — Sheela J Huff
(74) *Attorney, Agent, or Firm* — Choate, Hall & Stewart, LLP; Brenda Herschbach Jarrell; Tracy L. Vrablik

(57) ABSTRACT

In this application are described chimeric, humanized, affinity matured, stability enhanced, and bispecific Anti-GD2 antibodies and fragments thereof. Also provided are methods of using individual antibodies or compositions thereof for the detection, prevention, and/or therapeutical treatment of GD2-related diseases, in particular, neuroblastoma.

35 Claims, No Drawings

(56) References Cited

OTHER PUBLICATIONS

Cheung et al., "Humanizing murine IgG3 anti-GD2 antibody m3F8 substantially improves antibody-dependent cell-mediated cytotoxicity while retaining targeting in vivo," OncoImmunology 1(4): 477-489 (2012).
Dangl et al., "Segmental flexibility and complement fixation of genetically engineered chimeric human, rabbit and mouse antibodies," The EMBO Journal 7(7): 1989-1994 (1988).
Dillman et al., "Activation of Human Complement by Totally Human Monoclonal Antibodies," Molecular Immunology 32(13): 957-964 (1995).
Gillies et al., "High-Level expression of chimeric antibodies using adapted cDNA vairable region cassettes," Journal of Immunological Methods 125: 191-202 (1989).
International Preliminary Report on Patentability for PCT/US2011/041082 (8 pages) mailed Mar. 21, 2012.
International Search Report for PCT/US2011/041082 (5 pages) mailed Mar. 21, 2012.
Kushner et al., "High-Dose Cyclophosphamide Inhibition of Humoral Immune Response to Murine Monoclonal Anitbody 3F8 in Neuroblastoma Patients: Broad Implications for Immunotherapy," Pediatr Blood Cancer 48: 430-434 (2007).
Kushner et al., "Phase II Trial of the Anti-$G_{D2}$ Monoclonal Antibody 3F8 and Granulocyte-Macrophage Colony-Stimulating Factor for Neuroblastoma," Journal of Clinical Oncology 19(22): 4189-4194 (2001).
Kushner et al., "Successful Multifold Dose Escalation of Anti-$G_{D2}$ Monoclonal Antibody 3F8 in Patients With Neuroblastoma: A Phase I Study," Journal of Clinical Oncology 29(9): 1168-1174 (2011).
Modak et al., "Disialoganglioside Directed Immunotherapy of Neuroblastoma," Cancer Investigation 25: 67-77 (2007).
Seino et al., "Activation of human complement by mouse and mouse/human chimeric monoclonal antibodies," Clin Exp Immunol 94: 291-296 (1993).
Sorkin et al., "Anti-$GD_2$ with an FC point mutation reduces complement fixation and decreases antibody-induced allodynia," PAIN 149: 135-142 (2010).
Supplementary European Search Report in European Application No. 11796578.0 (10 pages) mailed Nov. 15, 2013.
Valim et al., "The effect of antibody isotype and antigenic epitope density on the complement-fixing activity of immune complexes: a systematic study using chimaeric anti-NIP antibodies with human Fc regions," Clin. exp. Immunol. 84: 1-8 (1991).
Written Opinion for PCT/US2011/041082 (7 pages) mailed Mar. 21, 2012.
Arai, S. et al., Infusion of the allogeneic cell line NK-92 in patients with advanced renal cell cancer or melanoma: a phase I trial, Cytotherapy, 10(6):625-632 (2008).
Brentjens, R. et al., Genetically Targeted T Cells Eradicate Systemic Acute Lymphoblastic Leukemia Xenografts, Clinical Cancer Research, 13(18):5426-5432 (2007).
Daldrup-Link, H.E. et al., In vivo tracking of genetically engineered, anti-HER2/neu directed natural killer cells to HER2/neu positive mammary tumors with magnetic resonance imaging, Eur. Radiol., 15(1): 26 pages (2005).
Davies, D.M. and Maher, J., Adoptive T-cell immunotherapy of cancer using chimeric antigen receptor-grafted T cells, Arch. Immunol. Ther. Exp. (Warsz)., 58(3):165-78 (2010).
Eshhar, Z. et al., Specific activation and targeting of cytotoxic lymphocytes through chimeric single chains consisting of antibody-binding domains and the γ or zeta subunits of the immunoglobulin and T-cell receptors, Proc. Natl. Acad. Sci. USA, 90:720-724 (1993).
Extended European Search Report for EP 11796578.0, 9 pages (Nov. 15, 2013).
Finney, H.M. et al., Activation of Resting Human Primary T Cells with Chimeric Receptors: Costimulation from CD28, Inducible Costimulator, CD134, and CD137 in Series with Signals from the TCRzetaChain, The Journal of Immunology, 172:104-113 (2004).

Gong, M.G. et al., Cancer Patient T Cells Genetically Targeted to Prostate-Specific Membrane Antigen Specifically Lyse Prostate Cancer Cells and Release Cytokines in Response to Prostate-Specific Membrane Antigen, Neoplasia,1(2):123-127 (1999).
Haynes, N.M. et al., Rejection of Syngeneic Colon Carcinoma by CTLs Expressing Single-Chain Antibody Receptors Codelivering CD28 Costimulation, The Journal of Immunology, 169:5780-5786 (2002).
Haynes, N.M. et al., Single-chain antigen recognition receptors that costimulate potent rejection of established experimental tumors, Blood, 100(9): 3155-3163 (2002).
Imai, C. and Campana, D., Genetic modification of T cells for cancer therapy, J. Biol. Regul. Homeost. Agents., 18(1):62-71 (2004).
Imai, C. et al., Chimeric receptors with 4-1BB signaling capacity provoke potent cytotoxicity against acute lymphoblastic leukemia, Leukemia. 18(4):676-84 (2004).
Irving, B.A. and Weiss, A., The cytoplasmic domain of the T cell receptor zeta chain is sufficient to couple to receptor-associated signal transduction pathways, Cell, 64(5):891-901 (1991).
Korbelik, M. et al., Cancer treatment by photodynamic therapy combined with adoptive immunotherapy using genetically altered natural killer cell line, International Journal of Cancer, 93:269-274 (2001).
Kowolik, C.M. et al., CD28 Costimulation Provided through a CD19-Specific Chimeric Antigen Receptor Enhances In vivo Persistence and Antitumor Efficacy of Adoptively Transferred T Cells, Cancer Research, 66(22):10995-11004 (2006).
Krause, A. et al., Antigen-dependent CD28 Signaling Selectivity Enhances Survival and Proliferation in Genetically Modified Activated Human Primary T Lymphocytes, The Journal of Experimental Medicine, 188(4):619-626 (1998).
Kruschinski, A. et al., Engineering antigen-specific primary human NK cells against HER-2 positive carcinomas, PNAS, 105(45):17481-17486 (2008).
Loskog, A. et al., Addition of the CD28 signaling domain to chimeric T-cell receptors enhances chimeric T-cell resistance to T regulatory cells, Leukemia, 20(10):1819-28 (2006).
Maher, J. et al., Human T-lymphocyte cytotoxicity and proliferation directed by a single chimeric TCRzeta /CD28 receptor, Nat. Biotechnol., 20(1):70-5 (2002).
Moeller, M. et al., A functional role for CD28 costimulation in tumor recognition by single-chain receptor-modified T cells, Cancer Gene Ther., 11(5):371-9 (2004).
Nguyen, P. and Geiger, T.L., Antigen-specific targeting of CD8+ T cells with receptor-modified T lymphocytes, Gene Ther., 10(7):594-604 (2003).
Papapetrou, E.P. et al., Harnessing endogenous miR-181a to segregate transgenic antigen receptor expression in developing versus post-thymic T cells in murine hematopoietic chimeras, The Journal of Clinical Investigation, 119(1):157-168 (2009).
Pegram, H.J. et al., Adoptive Transfer of Gene-Modified Primary NK Cells Can Specifically Inhibit Tumor Progression In Vivo, The Journal of Immunology, 181:3449-3455 (2008).
Pulé M.A. et al., A chimeric T cell antigen receptor that augments cytokine release and clonal expansion of primary human T cells, Mol. Ther., 12(5):933-41 (2005).
Roberts, M.R. et al., Antigen-Specific Cytolysis by Neutrophils and NK Cells Expressing Chimeric Immune Receptors Bearing zeta or γ Signaling Domains, The Journal of Immunology, 161:375-384 (1998).
Romeo, C. et al., Sequence requirements for induction of cytolysis by the T cell antigen/Fc receptor zeta chain, Cell, 68(5):889-97 (1992).
Rossig, C. et al., Epstein-Barr virus-specific human T lymphocytes expressing antitumor chimeric T-cell receptors: potential for improved immunotherapy, Blood, 99(6):2009-2016 (2002).
Tam, Y.K. et al., Immunotherapy of Malignant Melanoma in a SCID Mouse Model Using the Highly Cytotoxic Natural Killer Cell Line NK-92, Journal of Hematotherapy, 8:281-290 (1999).
Teng, M.W. et al., Immunotherapy of cancer using systemically delivered gene-modified human T lymphocytes, Hum. Gene Ther., 15(7):699-708 (2004).
Vera, J. et al., T lymphocytes redirected against the κ light chain of human immunoglobulin efficiently kill mature B lymphocyte-derived malignant cells, Blood, 108(12):3890-3897 (2006).

(56) References Cited

OTHER PUBLICATIONS

Wang, G. et al., A T cell-independent anitutmor response in mice with bone marrow retrovirally transduced with an antibody/Fc-γ chain chimeric receptor gene recognizing a human ovarian cancer antigen, Nature Medicine, 4(2): 168-172 (1998).

Wang, J. et al, Optimizing adoptive polyclonal T cell immunotherapy of lymphomas, using a chimeric T cell receptor possessing CD28 and CD137 costimulatory domains, Hum. Gene Ther., 18(8):712-25 (2007).

Weijtens, M.E. et al., Single chain Ig/gamma gene-redirected human T lymphocytes produce cytokines, specifically lyse tumor cells, and recycle lytic capacity, J. Immunol., 157(2):836-43 (1996).

Wilkie, S. et al., Retargeting of Human T Cells to Tumor-Associated MUC1: The Evolution of a Chimeric Antigen Receptor, The Journal of Immunology, 180:4901-4909 (2008).

Zakrzewski, J. L. et al., Adoptive transfer of T-cell precursors enhances T-cell reconstitution after allogeneic hematopoietic stem cell transplantation, Nature Medicine, 12(9):1039-1047 (2006).

Zakrzewski, J.L. et al., Tumor immunotherapy across MHC barriers using allogeneic Tcell precursors, Nat. Biotechnol., 26(4):453-461 (2008).

Helene, M. et al., Inhibition of graft-versus-host disease. Use of a T cell-controlled suicide gene, J. Immunol., 158(11):5079-82 (1997).

Rossig, C. and Brenner, M.K., Genetic modification of T lymphocytes for adoptive immunotherapy, Mol. Ther., 10(1):5-18 (2004).

Arbit, E. et al., Quantitative studies of monoclonal antibody targeting to disialoganglioside $G_{D2}$ in human brain tumors, European Journal of Nuclear Medicine, 22(5): 419-426 (1995).

Barker, E. et al., Effect of a Chimeric Anti-Ganglioside $G_{D2}$ Antibody on Cell-mediated Lysis of Human Neuroblastoma Cells, Cancer Research 51: 144-149 (1991).

Barker, E. And Reisfeld, R.A., A Mechanism for Neutrophil-mediated Lysis of Human Neuroblastoma Cells, Cancer Research 53: 362-367 (1993).

Bergman, I. et al., Comparison of in vitro antibody-targeted cytotoxicity using mouse, rat and human effectors, Cancer Immunology, Immunotherapy, 49: 259-266 (2000).

Cheung, N.V. et al., Monoclonal Antibodies to a Glycolipid Antigen on Human Neuroblastoma Cells, Cancer Research 45: 2642-2649 (1985).

Cheung, N.V. et al., Complete Tumor Ablation With Iodine 131-Radiolabeled Disialoganglioside $G_{D2}$-Specific Monoclonal Antibody Against Human Neuroblastoma Xenografted in Nude Mice, JNCI 77(3): 739-745 (1986).

Cheung, N.V. et al., Detection of Neuroblastoma Cells in Bone Marrow Using $G_{D2}$ Specific Monoclonal Antibodies, Journal of Clinical Oncology 4(3): 363-369 (1986).

Cheung, N.V. et al., Disialoganglioside $G_{D2}$ Anti-idiotypic monoclonal antibodies, Int. J. Cancer 54: 499-505 (1993).

Cheung, N.V. et al. Single-Chain Fv-Streptavidin Substantially Improved Therapeutic Index in Multistep Targeting Directed at Disialoganglioside $G_{D2}$, The Journal of Nuclear Medicine, 45: 867-877 (2004).

Cheung, N.V. et al., FCGR2A Polymorphism Is Correlated With Clinical Outcome After Immunotherapy of Neuroblastoma With Anti-GD2 Antibody and Granulocyte Macrophage Colony-Stimulating Factor, Journal of Clinical Oncology, 24(18): 2885-2890 (2006).

Gilman, A.L. et al., Phase I Study of ch14.18 With Granulocyte-Macrophage Colony-Stimulating Factor and Interleukin-2 in Children With Neuroblastoma After Autologous Bone Marrow Transplantation or Stem-Cell Rescue: A Report From the Children's Oncology Group, Journal of Clinical Oncology, 27(1): 85-91 (2009).

Grabert, R.C. et al., Human T Cells Armed with Her2/neu Bispecific Antibodies Divide, Are Cytotoxic, and Secrete Cytokines with Repeated Stimulation, Clinical Cancer Research, 12(2): 569-76 (2006).

Grant, S.C. et al., Targeting of small-cell lung cancer using the anti-GD2 ganglioside monoclonal antibody 3F8: a pilot trial, European Journal of Nuclear Medicine, 23(2): 145-149 (1996).

Kramer, K. et al., Phase I Study of Targeted Radioimmunotherapy for Leptomeningeal Cancers Using Intra-Ommaya 131-I-3F8, Journal of Clinical Oncology, 25(34): 5465-5470 (2007).

Lazar, G.A. et al., Engineered antibody Fc variants with enhanced effector function, PNAS USA, 103(11): 4005-4010 (2006).

Modak, S. et al., Monoclonal Antibody 8H9 Targets a Novel Cell Surface Antigen Expressed by a Wide Spectrum of Human Solid Tumors, Cancer Research, 61: 4048-4054 (2001).

Mueller, B.M. et al., Serum half-life and tumor localization of a chimeric antibody deleted of the $C_H2$ domain and directed against the disialoganglioside GD2, PNAS USA, 87: 5702-5705 (1990).

Mujoo, K. et al., Functional Properties and Effect on Growth Suppression of Human Neuroblastoma Tumors by Isotype Switch Variants of Monoclonal Antiganglioside $G_{D2}$ Antibody 14.18, Cancer Research, 49: 2857-2861 (1989).

Navid, F. et al., Anti-GD2 Antibody Therapy for GD2-expressing Tumors, Current Cancer Drug Targets, 10(2): 200-209 (2010).

Patel, K. et al., Monoclonal antibody 3F8 recognises the neural cell adhesion molecule (NCAM) in addition to ganglioside GD2, Br. J. Cancer, 60: 861-866 (1989).

Saarinen, U.M. et al., Eradication of Neuroblastoma Cells in Vitro by Monoclonal Antibody and Human Complement: Method for Purging Autologous Bone Marrow, Cancer Research, 45: 5969-5975 (1985).

Saleh, M.N. et al., Phase I trial of the chimeric anti-GD2 monoclonal antibody ch14.18 in patients with malignant melanoma, Hum. Antibodies Hybridomas, 3: 19-24 (1992).

Simon, T. et al., Consolidation Treatment With Chimeric Anti-GD2-Antibody ch14.18 in Children Older Than 1 Year With Metastatic Neuroblastoma, Journal of Clinical Oncology, 22(17): 35493557 (2004).

Thakur, A. and Lum, L.G., Cancer therapy with bispecific antibodies: Clinical experience, Curr Opin. Mol. Ther., 12(3): 340-349 (2010).

Yu, A.L. et al., Anti-GD2 Antibody with GM-CSF, Interleukin-2, and Isotretinoin for Neuroblastoma, The New England Journal of Medicine, 363(14): 1324-1334 (2010).

\* cited by examiner

SEQUENCE LISTING

```
<160> NUMBER OF SEQ ID NOS: 24

<210> SEQ ID NO 1
<211> LENGTH: 449
<212> TYPE: PRT
<213> ORGANISM: Artificial sequence
<220> FEATURE:
<223> OTHER INFORMATION: Chimeric 3F8 heavy chain gamma 1

<400> SEQUENCE: 1

Gln Val Gln Leu Lys Glu Ser Gly Pro Gly Leu Val Ala Pro Ser Gln
1               5                   10                  15
```

Ser Leu Ser Ile Thr Cys Thr Val Ser Gly Phe Ser Val Thr Asn Tyr
            20                  25                  30
Gly Val His Trp Val Arg Gln Pro Gly Lys Gly Leu Glu Trp Leu
        35                  40                  45
Gly Val Ile Trp Ala Gly Gly Ile Thr Asn Tyr Asn Ser Ala Phe Met
            50                  55                  60
Ser Arg Leu Ser Ile Ser Lys Asp Asn Ser Lys Ser Gln Val Phe Leu
65                  70                  75                  80
Lys Met Asn Ser Leu Gln Ile Asp Asp Thr Ala Met Tyr Tyr Cys Ala
                85                  90                  95
Ser Arg Gly Gly His Tyr Gly Tyr Ala Leu Asp Tyr Trp Gly Gln Gly
            100                 105                 110
Thr Ser Val Thr Val Ser Ser Ala Ser Thr Lys Gly Pro Ser Val Phe
        115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430

```
Ala Leu His Asn His Tyr Thr Gln Lys Ser Leu Ser Leu Ser Pro Gly
            435                 440                 445

Lys

<210> SEQ ID NO 2
<211> LENGTH: 211
<212> TYPE: PRT
<213> ORGANISM: Artificial sequence
<220> FEATURE:
<223> OTHER INFORMATION: Chimeric 3F8 light chain kappa

<400> SEQUENCE: 2

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Thr Trp Tyr Gln Gln Lys Ala Gly Gln Ser Pro Lys Leu Leu Ile
        35                  40                  45

Tyr Ser Ala Ser Asn Arg Tyr Ser Gly Val Pro Asp Arg Phe Thr Gly
    50                  55                  60

Ser Gly Tyr Gly Thr Ala Phe Thr Phe Thr Ile Ser Thr Val Gln Ala
65                  70                  75                  80

Glu Asp Leu Ala Val Tyr Phe Cys Gln Gln Asp Tyr Ser Ser Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 3
<211> LENGTH: 446
<212> TYPE: PRT
<213> ORGANISM: Artificial sequence
<220> FEATURE:
<223> OTHER INFORMATION: Chimeric 3F8 heavy chain gamma 4

<400> SEQUENCE: 3

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Val Thr Asn Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ile Thr Asn Tyr Asn Ser Ala Phe Met
    50                  55                  60
```

```
Ser Arg Leu Ser Ile Ser Lys Asp Asn Ser Lys Ser Gln Val Phe Leu
 65                  70                  75                  80

Lys Met Asn Ser Leu Gln Ile Asp Asp Thr Ala Met Tyr Tyr Cys Ala
                 85                  90                  95

Ser Arg Gly Gly His Tyr Gly Tyr Ala Leu Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 4
<211> LENGTH: 448
<212> TYPE: PRT
<213> ORGANISM: Artificial sequence
<220> FEATURE:
<223> OTHER INFORMATION: huH1 - gamma 1
```

<400> SEQUENCE: 4

```
Gln Val Gln Leu Val Glu Ser Gly Pro Gly Val Val Gln Pro Gly Arg
  1               5                  10                  15

Ser Leu Arg Ile Ser Cys Ala Val Ser Gly Phe Ser Val Thr Asn Tyr
             20                  25                  30

Gly Val His Trp Val Arg Gln Pro Pro Gly Lys Gly Leu Glu Trp Leu
         35                  40                  45

Gly Val Ile Trp Ala Gly Gly Ile Thr Asn Tyr Asn Ser Ala Phe Met
     50                  55                  60

Ser Arg Leu Thr Ile Ser Lys Asp Asn Ser Lys Asn Thr Val Tyr Leu
 65                  70                  75                  80

Gln Met Asn Ser Leu Arg Ala Glu Asp Thr Ala Met Tyr Tyr Cys Ala
                 85                  90                  95

Ser Arg Gly Gly His Tyr Gly Tyr Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
```

```
                            405                 410                 415
Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

<210> SEQ ID NO 5
<211> LENGTH: 211
<212> TYPE: PRT
<213> ORGANISM: Artificial sequence
<220> FEATURE:
<223> OTHER INFORMATION: HuL1- kappa

<400> SEQUENCE: 5

Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 6
<211> LENGTH: 448
<212> TYPE: PRT
<213> ORGANISM: Artificial sequence
<220> FEATURE:
<223> OTHER INFORMATION: huH2 - gamma 1

<400> SEQUENCE: 6

Gln Val Gln Leu Lys Glu Ser Gly Pro Gly Val Val Gln Pro Gly Gln
1               5                   10                  15

Ser Leu Ser Ile Ser Cys Ala Val Ser Gly Phe Ser Val Thr Asn Tyr
            20                  25                  30

Gly Val His Trp Val Arg Gln Pro Pro Gly Lys Gly Leu Glu Trp Leu
        35                  40                  45
```

Gly Val Ile Trp Ala Gly Gly Ile Thr Asn Tyr Asn Ser Ala Phe Met
 50                  55                  60

Ser Arg Leu Thr Ile Ser Lys Asp Asn Ser Lys Ser Thr Val Tyr Leu
 65                  70                  75                  80

Lys Met Asn Ser Leu Gln Ala Glu Asp Thr Ala Met Tyr Tyr Cys Ala
                 85                  90                  95

Ser Arg Gly Gly His Tyr Gly Tyr Ala Leu Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 7
<211> LENGTH: 211
<212> TYPE: PRT

```
<213> ORGANISM: Artificial sequence
<220> FEATURE:
<223> OTHER INFORMATION: huL2 - kappa

<400> SEQUENCE: 7

Ser Ile Val Met Thr Gln Thr Pro Lys Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ser Pro Lys Leu Leu Ile
        35                  40                  45

Tyr Ser Ala Ser Asn Arg Tyr Ser Gly Val Pro Asp Arg Phe Ser Gly
    50                  55                  60

Ser Gly Tyr Gly Thr Ala Phe Thr Phe Thr Ile Ser Ser Val Gln Ala
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210

<210> SEQ ID NO 8
<211> LENGTH: 446
<212> TYPE: PRT
<213> ORGANISM: Artificial sequence
<220> FEATURE:
<223> OTHER INFORMATION: huH1-gamma 4

<400> SEQUENCE: 8

Gln Val Gln Leu Val Glu Ser Gly Pro Gly Val Val Gln Pro Gly Arg
1               5                   10                  15

Ser Leu Arg Ile Ser Cys Ala Val Ser Gly Phe Ser Val Thr Asn Tyr
            20                  25                  30

Gly Val His Trp Val Arg Gln Pro Pro Gly Lys Gly Leu Glu Trp Leu
        35                  40                  45

Gly Val Ile Trp Ala Gly Gly Ile Thr Asn Tyr Asn Ser Ala Phe Met
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Met Tyr Tyr Cys Ala
                85                  90                  95

Ser Arg Gly Gly His Tyr Gly Tyr Ala Leu Asp Tyr Trp Gly Gln Gly
            100                 105                 110
```

```
Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Ser Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Gly Lys
        435                 440                 445

<210> SEQ ID NO 9
<211> LENGTH: 449
<212> TYPE: PRT
<213> ORGANISM: Artificial sequence
<220> FEATURE:
<223> OTHER INFORMATION: huH3-gamma 1, with stability enhanced mutations

<400> SEQUENCE: 9

Gln Val Gln Leu Val Glu Ser Gly Pro Gly Leu Val Gln Pro Gly Arg
1               5                   10                  15

Ser Leu Arg Leu Thr Cys Ala Val Ser Gly Phe Ser Val Thr Asn Tyr
            20                  25                  30
```

-continued

```
Gly Val His Trp Val Arg Gln Pro Gly Lys Gly Leu Glu Trp Leu
         35                  40                  45
Gly Val Ile Trp Ala Gly Gly Ile Thr Asn Tyr Asn Ser Ala Phe Met
 50                  55                  60
Ser Arg Leu Thr Ile Ser Lys Asp Asn Ser Lys Asn Thr Val Tyr Leu
 65                  70                  75                  80
Gln Met Asn Ser Leu Arg Ala Glu Asp Thr Ala Val Tyr Tyr Cys Ala
                 85                  90                  95
Ser Arg Gly Gly His Tyr Gly Tyr Ala Leu Asp Tyr Trp Gly Gln Gly
                100                 105                 110
Thr Leu Val Thr Val Ser Ser Ala Ser Thr Lys Gly Pro Ser Val Phe
            115                 120                 125
Pro Leu Ala Pro Ser Ser Lys Ser Thr Ser Gly Gly Thr Ala Ala Leu
    130                 135                 140
Gly Cys Leu Val Lys Asp Tyr Phe Pro Glu Pro Val Thr Val Ser Trp
145                 150                 155                 160
Asn Ser Gly Ala Leu Thr Ser Gly Val His Thr Phe Pro Ala Val Leu
                165                 170                 175
Gln Ser Ser Gly Leu Tyr Ser Leu Ser Ser Val Val Thr Val Pro Ser
            180                 185                 190
Ser Ser Leu Gly Thr Gln Thr Tyr Ile Cys Asn Val Asn His Lys Pro
        195                 200                 205
Ser Asn Thr Lys Val Asp Lys Arg Val Glu Pro Lys Ser Cys Asp Lys
    210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
                245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Asn Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Asp Glu Leu Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys
```

<210> SEQ ID NO 10
<211> LENGTH: 211
<212> TYPE: PRT
<213> ORGANISM: Artificial sequence
<220> FEATURE:
<223> OTHER INFORMATION: HuL3 - kappa

<400> SEQUENCE: 10

```
Ser Ile Val Met Thr Gln Thr Pro Ala Phe Leu Leu Val Ser Ala Gly
1               5                   10                  15

Glu Arg Val Thr Ile Thr Cys Arg Ala Ser Gln Ser Val Ser Asn Asp
            20                  25                  30

Val Thr Trp Tyr Gln Gln Lys Ala Gly Gln Ala Pro Arg Leu Leu Ile
        35                  40                  45

Tyr Ser Ala Ser Asn Arg Tyr Thr Gly Ile Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gly Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys
    210
```

<210> SEQ ID NO 11
<211> LENGTH: 684
<212> TYPE: DNA
<213> ORGANISM: Artificial sequence
<220> FEATURE:
<223> OTHER INFORMATION: Hu3F8-H1L1-IgG1, light chain

<400> SEQUENCE: 11

```
atgggctggt cctgcatcat cctgttcctg gtggccaccg ccaccggcga gatcgtgatg    60
acccagaccc ccgccaccct gtccgtgtcc gccggcgagc gggtgaccat cacctgcaag   120
gcctcccagt ccgtgtccaa cgacgtgacc tggtaccagc agaagcccgg ccaggccccc   180
cggctgctga tctactccgc ctccaaccgg tactccggcg tgcccgcccg gttctccggc   240
tccggctacg gcaccgagtt caccttcacc atctcctccg tgcagtccga ggacttcgcc   300
gtgtacttct gccagcagga ctactcctcc ttcggccagg gcaccaagct ggagatcaag   360
cggaccgtgg ccgcccctc cgtgttcatc ttccccccct ccgacgagca gctgaagtcc   420
ggcaccgcct ccgtggtgtg cctgctgaac aacttctacc ccgggaggc caaggtgcag   480
```

| tggaaggtgg acaacgccct gcagtccggc aactcccagg agtccgtgac cgagcaggac | 540 |
| tccaaggact ccacctactc cctgtcctcc accctgaccc tgtccaaggc cgactacgag | 600 |
| aagcacaagg tgtacgcctg cgaggtgacc caccagggcc tgtcctcccc cgtgaccaag | 660 |
| tccttcaacc ggggcgagtg ctag | 684 |

<210> SEQ ID NO 12
<211> LENGTH: 1398
<212> TYPE: DNA
<213> ORGANISM: Artificial sequence
<220> FEATURE:
<223> OTHER INFORMATION: Hu3F8-H1L1-IgG1, heavy chain

<400> SEQUENCE: 12

| atgggctggt cctgcatcat cctgttcctg gtggccaccg ccaccggcca ggtgcagctg | 60 |
| gtggagtccg gccccggcgt ggtgcagccc ggccggtccc tgcggatctc ctgcgccgtg | 120 |
| tccggcttct ccgtgaccaa ctacggcgtg cactgggtgc ggcagccccc cggcaagggc | 180 |
| ctggagtggt gggcgtgat ctgggccggc ggcatcacca actacaactc cgccttcatg | 240 |
| tcccggctga ccatctccaa ggacaactcc aagaacaccg tgtacctgca gatgaactcc | 300 |
| ctgcggcccg aggacaccgc catgtactac tgcgcctccc ggggcggcca ctacggctac | 360 |
| gccctggact actggggcca gggcaccctg gtgaccgtgt cctccgcctc caccaagggc | 420 |
| ccatcggtct tccccctggc accctcctcc aagagcacct ctgggggcac agcggccctg | 480 |
| ggctgcctgg tcaaggacta cttccccgaa ccggtgacgg tgtcgtggaa ctcaggcgcc | 540 |
| ctgaccagcg gcgtgcacac cttcccggcc gtcctacagt cctcaggact ctactccctc | 600 |
| agcagcgtgg tgaccgtgcc ctccagcagc ttgggcaccc agacctacat ctgcaacgtg | 660 |
| aatcacaagc ccagcaacac caaggtggac aagagagttg agcccaaatc ttgtgacaaa | 720 |
| actcacacat gcccaccgtg cccagcacct gaactcctgg ggggaccgtc agtcttcctc | 780 |
| ttccccccaa aacccaagga caccctcatg atctcccgga cccctgaggt cacatgcgtg | 840 |
| gtggtggacg tgagccacga agaccctgag gtcaagttca actggtacgt ggacggcgtg | 900 |
| gaggtgcata atgccaagac aaagccgcgg gaggagcagt acaacagcac gtaccgtgtg | 960 |
| gtcagcgtcc tcaccgtcct gcaccaggac tggctgaatg gcaaggagta caagtgcaag | 1020 |
| gtctccaaca aagccctccc agcccccatc gagaaaacca tctccaaagc caaagggcag | 1080 |
| ccccgagaac acaggtgta caccctgccc ccatcccggg atgagctgac caagaaccag | 1140 |
| gtcagcctga cctgcctggt caaaggcttc tatcccagcg acatcgccgt ggagtgggag | 1200 |
| agcaatgggc agccggagaa caactacaag accacgcctc ccgtgctgga ctccgacggc | 1260 |
| tccttcttcc tctacagcaa gctcaccgtg gacaagagca ggtggcagca ggggaacgtc | 1320 |
| ttctcatgct ccgtgatgca tgaggctctg cacaaccact acacgcagaa gagcctctcc | 1380 |
| ctgtctccgg gtaaatga | 1398 |

<210> SEQ ID NO 13
<211> LENGTH: 684
<212> TYPE: DNA
<213> ORGANISM: Artificial sequence
<220> FEATURE:
<223> OTHER INFORMATION: Hu3F8-H1L1-IgG4 light chain

<400> SEQUENCE: 13

| atgggctggt cctgcatcat cctgttcctg gtggccaccg ccaccggcga gatcgtgatg | 60 |
| acccagaccc ccgccaccct gtccgtgtcc gccggcgagc gggtgaccat cacctgcaag | 120 |

```
gcctcccagt ccgtgtccaa cgacgtgacc tggtaccagc agaagcccgg ccaggccccc    180
cggctgctga tctactccgc ctccaaccgg tactccggcg tgcccgcccg gttctccggc    240
tccggctacg gcaccgagtt caccttcacc atctcctccg tgcagtccga ggacttcgcc    300
gtgtacttct gccagcagga ctactcctcc ttcggccagg gcaccaagct ggagatcaag    360
cggaccgtgg ccgcccctc cgtgttcatc ttcccccct ccgacgagca gctgaagtcc    420
ggcaccgcct ccgtggtgtg cctgctgaac aacttctacc ccggggaggc caaggtgcag    480
tggaaggtgg acaacgccct gcagtccggc aactcccagg agtccgtgac cgagcaggac    540
tccaaggact ccacctactc cctgtcctcc accctgaccc tgtccaaggc cgactacgag    600
aagcacaagg tgtacgcctg cgaggtgacc caccagggcc tgtcctcccc cgtgaccaag    660
tccttcaacc ggggcgagtg ctag                                          684
```

<210> SEQ ID NO 14
<211> LENGTH: 1389
<212> TYPE: DNA
<213> ORGANISM: Artificial sequence
<220> FEATURE:
<223> OTHER INFORMATION: Hu3F8-H1L1-IgG4 heavy chain

<400> SEQUENCE: 14

```
atgggctggt cctgcatcat cctgttcctg gtggccaccg ccaccggcca ggtgcagctg     60
gtggagtccg gccccggcgt ggtgcagccc ggccggtccc tgcggatctc ctgcgccgtg    120
tccggcttct ccgtgaccaa ctacggcgtg cactgggtgc ggcagccccc cggcaagggc    180
ctggagtggc tgggcgtgat ctgggccggc ggcatcacca actacaactc cgccttcatg    240
tcccggctga ccatctccaa ggacaactcc aagaacaccg tgtacctgca gatgaactcc    300 ctgcggggccg aggacaccgc catgtactac tgcgcctccc ggggcggcca ctacggctac    360
gccctggact actggggcca gggcaccctg gtgaccgtgt cctccgcctc caccaagggc    420
ccctccgtgt tcccctggc ccctgctcc cggtccacct ccgagtccac cgccgccctg    480
ggctgcctgg tgaaggacta cttccccgag cccgtgaccg tgtcctggaa ctccggcgcc    540
ctgacctccg gcgtgcacac cttccccgcc gtgctgcagt cctccggcct gtactccctg    600
tcctccgtgg tgaccgtgcc ctcctcctcc ctgggcacca agacctacac ctgcaacgtg    660
gaccacaagc cctccaacac caaggtggac aagcgggtgg agtccaagta cggcccccc    720 tgccccctcct gccccgcccc cgagttcctg ggcggcccct ccgtgttcct gttccccccc    780
aagcccaagg acaccctgat gatctcccgg accccgagg tgacctgcgt ggtggtggac    840
gtgtcccagg aggaccccga ggtgcagttc aactggtacg tggacggcgt ggaggtgcac    900
aacgccaaga ccaagcccg ggaggagcag ttcaactcca cctaccgggt ggtgtccgtg    960
ctgaccgtgc tgcaccagga ctggctgaac ggcaaggagt acaagtgcaa ggtgtccaac   1020
aagggcctgc cctcctccat cgagaagacc atctccaagg ccaagggcca gccccgggag   1080
ccccaggtgt acaccctgcc ccctcccag gaggagatga ccaagaacca ggtgtccctg   1140
acctgcctgg tgaagggctt ctaccccctc gacatcgccg tggagtggga gtccaacggc   1200
cagcccgaga acaactacaa gaccaccccc ccgtgctgg actccgacgg ctccttcttc   1260
ctgtactccc ggctgaccgt ggacaagtcc cggtggcagg agggcaacgt gttctcctgc   1320
tccgtgatgc acgaggccct gcacaaccac tacacccaga agtccctgtc cctgtccctg   1380
ggcaagtga                                                          1389
```

<210> SEQ ID NO 15
<211> LENGTH: 684
<212> TYPE: DNA
<213> ORGANISM: Artificial sequence
<220> FEATURE:
<223> OTHER INFORMATION: Hu3F8-H2L2-IgG1 light chain

<400> SEQUENCE: 15

| | | | | | |
|---|---|---|---|---|---|
| atgggctggt | cctgcatcat | cctgttcctg | gtggccaccg | ccaccggctc | catcgtgatg | 60 |
| acccagaccc | ccaagaccct | gtccgtgtcc | gccggcgagc | gggtgaccat | cacctgcaag | 120 |
| gcctcccagt | ccgtgtccaa | cgacgtgacc | tggtaccagc | agaagcccgg | ccagtccccc | 180 |
| aagctgctga | tctactccgc | ctccaaccgg | tactccggcg | tgcccaccg | gttctccggc | 240 |
| tccggctacg | gcaccgcctt | caccttcacc | atctcctccg | tgcaggccga | ggacttcgcc | 300 |
| gtgtacttct | gccagcagga | ctactcctcc | ttcggccagg | gcaccaagct | ggagatcaag | 360 |
| cggaccgtgg | ccgcccctc | cgtgttcatc | ttccccccct | ccgacgagca | gctgaagtcc | 420 |
| ggcaccgcct | ccgtggtgtg | cctgctgaac | aacttctacc | ccggggaggc | caaggtgcag | 480 |
| tggaaggtgg | acaacgccct | gcagtccggc | aactcccagg | agtccgtgac | cgagcaggac | 540 |
| tccaaggact | ccacctactc | cctgtcctcc | accctgaccc | tgtccaaggc | cgactacgag | 600 |
| aagcacaagg | tgtacgcctg | cgaggtgacc | caccagggcc | tgtcctcccc | cgtgaccaag | 660 |
| tccttcaacc | ggggcgagtg | ctag | | | | 684 |

<210> SEQ ID NO 16
<211> LENGTH: 1398
<212> TYPE: DNA
<213> ORGANISM: Artificial sequence
<220> FEATURE:
<223> OTHER INFORMATION: Hu3F8-H2L2-IgG1, heavy chain

<400> SEQUENCE: 16

| | | | | | |
|---|---|---|---|---|---|
| atgggctggt | cctgcatcat | cctgttcctg | gtggccaccg | ccaccggcca | ggtgcagctg | 60 |
| aaggagtccg | gccccggcgt | ggtgcagccc | ggccagtccc | tgtccatctc | ctgcgccgtg | 120 |
| tccggcttct | ccgtgaccaa | ctacggcgtg | cactgggtgc | ggcagccccc | cggcaagggc | 180 |
| ctggagtggc | tgggcgtgat | ctgggccggc | ggcatcacca | actacaactc | cgccttcatg | 240 |
| tcccggctga | ccatctccaa | ggacaactcc | aagtccaccg | tgtacctgaa | gatgaactcc | 300 |
| ctgcaggccg | aggacaccgc | catgtactac | tgcgcctccc | ggggcggcca | ctacggctac | 360 |
| gccctggact | actggggcca | gggcaccctg | gtgaccgtgt | cctccgcctc | caccaagggc | 420 |
| ccatcggtct | tccccctggc | accctcctcc | aagagcacct | ctgggggcac | agcggccctg | 480 |
| ggctgcctgg | tcaaggacta | cttccccgaa | ccggtgacgg | tgtcgtggaa | ctcaggcgcc | 540 |
| ctgaccagcg | gcgtgcacac | cttcccggcc | gtcctacagt | cctcaggact | ctactccctc | 600 |
| agcagcgtgg | tgaccgtgcc | ctccagcagc | ttgggcaccc | agacctacat | ctgcaacgtg | 660 |
| aatcacaagc | ccagcaacac | caaggtggac | aagagagttg | agcccaaatc | ttgtgacaaa | 720 |
| actcacacat | gcccaccgtg | cccagcacct | gaactcctgg | ggggaccgtc | agtcttcctc | 780 |
| ttcccccaa | aacccaagga | caccctcatg | atctcccgga | cccctgaggt | cacatgcgtg | 840 |
| gtggtggacg | tgagccacga | agaccctgag | gtcaagttca | actggtacgt | ggacggcgtg | 900 |
| gaggtgcata | atgccaagac | aaaaccgcgc | gaggagcagt | acaacagcac | gtaccgtgtg | 960 |
| gtcagcgtcc | tcaccgtcct | gcaccaggac | tggctgaatg | gcaaggagta | caagtgcaag | 1020 |
| gtctccaaca | aagccctccc | agccccatc | gagaaaacca | tctccaaagc | caaagggcag | 1080 |

```
cccgagaac cacaggtgta caccctgccc ccatcccggg atgagctgac caagaaccag    1140
gtcagcctga cctgcctggt caaaggcttc tatcccagcg acatcgccgt ggagtgggag    1200
agcaatgggc agccggagaa caactacaag accacgcctc ccgtgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaatga                                                  1398
```

<210> SEQ ID NO 17
<211> LENGTH: 684
<212> TYPE: DNA
<213> ORGANISM: Artificial sequence
<220> FEATURE:
<223> OTHER INFORMATION: ch3F8-IgG1, light chain

<400> SEQUENCE: 17

```
atgggctggt cctgcatcat cctgttcctg gtggccaccg ccaccggcag tattgtgatg      60
acccagactc ccaaattcct gcttgtatca gcaggagaca gggttaccat aacctgcaag     120
gccagtcaga gtgtgagtaa tgatgtaact tggtaccaac agaaggcagg gcagtctcct     180
aaactgctga tatactctgc atccaatcgc tattctggag tccctgaccg cttcactggc     240
agtggatatg ggacggcttt cactttcacc atcagcactg tgcaggctga agacctggca     300
gtttatttct gtcagcagga ttatagttcg ttcggagggg ggaccaagct ggaaataaag     360
cggaccgtgg ccgcccctc cgtgttcatc ttccccccct ccgacgagca gctgaagtcc     420
ggcaccgcct ccgtggtgtg cctgctgaac aacttctacc ccggggaggc caaggtgcag     480
tggaaggtgg acaacgccct gcagtccggc aactcccagg agtccgtgac cgagcaggac     540
tccaaggact ccacctactc cctgtcctcc accctgaccc tgtccaaggc cgactacgag     600
aagcacaagg tgtacgcctg cgaggtgacc caccagggcc tgtcctcccc cgtgaccaag     660
tccttcaacc ggggcgagtg ctag                                           684
```

<210> SEQ ID NO 18
<211> LENGTH: 1395
<212> TYPE: DNA
<213> ORGANISM: Artificial sequence
<220> FEATURE:
<223> OTHER INFORMATION: ch3F8-IgG1, heavy chain

<400> SEQUENCE: 18

```
atgggctggt cctgcatcat cctgttcctg gtggccaccg ccaccggcca ggtgcagctg      60
aaggagtcag gcctggcct ggtggcgccc tcacagagcc tgtccatcac ttgcactgtc     120
tctgggtttt cagtaaccaa ttatggtgta cactgggttc gccagcctcc aggaaagggt     180
ctggagtggc tgggagtaat atgggctggt ggaattacaa attataattc ggctttcatg     240
tccagactga gcatcagcaa agacaactcc aagagtcaag tttttcttaaa aatgaacagt     300 ctgcaaattg atgacacagc catgtactac tgtgccagtc gggggggtca ctacggctat     360 gcttttggact actggggtca aggaacctca gtcaccgtct cctcagcctc caccaagggc     420
ccatcggtct tccccctggc accctcctcc aagagcacct ctgggggcac agcggccctg     480
ggctgcctgg tcaaggacta cttccccgaa ccggtgacgg tgtcgtggaa ctcaggcgcc     540
ctgaccagcg gcgtgcacac cttcccggcc gtcctacagt cctcaggact ctactccctc     600
agcagcgtgg tgaccgtgcc ctccagcagc ttgggcaccc agacctacat ctgcaacgtg     660
```

| | |
|---|---|
| aatcacaagc ccagcaacac caaggtggac aagagagttg agcccaaatc ttgtgacaaa | 720 |
| actcacacat gcccaccgtg cccagcacct gaactcctgg ggggaccgtc agtcttcctc | 780 |
| ttccccccaa acccaagga cccctcatg atctcccgga cccctgaggt cacatgcgtg | 840 |
| gtggtggacg tgagccacga agaccctgag gtcaagttca actggtacgt ggacggcgtg | 900 |
| gaggtgcata atgccaagac aaagccgcgg gaggagcagt acaacagcac gtaccgtgtg | 960 |
| gtcagcgtcc tcaccgtcct gcaccaggac tggctgaatg gcaaggagta caagtgcaag | 1020 |
| gtctccaaca aagccctccc agcccccatc gagaaaacca tctccaaagc caaagggcag | 1080 |
| ccccgagaac cacaggtgta caccctgccc ccatcccggg atgagctgac caagaaccag | 1140 |
| gtcagcctga cctgcctggt caaaggcttc tatcccagcg acatcgccgt ggagtgggag | 1200 |
| agcaatgggc agccggagaa caactacaag accacgcctc ccgtgctgga ctccgacggc | 1260 |
| tccttcttcc tctacagcaa gctcaccgtg gacaagagca ggtggcagca ggggaacgtc | 1320 |
| ttctcatgct ccgtgatgca tgaggctctg cacaaccact acacgcagaa gagcctctcc | 1380 |
| ctgtctccgg gtaaa | 1395 |

<210> SEQ ID NO 19
<211> LENGTH: 684
<212> TYPE: DNA
<213> ORGANISM: Artificial sequence
<220> FEATURE:
<223> OTHER INFORMATION: ch3F8-IgG4 light chain

<400> SEQUENCE: 19

| | |
|---|---|
| atgggctggt cctgcatcat cctgttcctg gtgccaccg ccaccggcag tattgtgatg | 60 |
| acccagactc ccaaattcct gcttgtatca gcaggagaca gggttaccat aacctgcaag | 120 |
| gccagtcaga gtgtgagtaa tgatgtaact tggtaccaac agaaggcagg gcagtctcct | 180 |
| aaactgctga tatactctgc atccaatcgc tattctggag tccctgaccg cttcactggc | 240 |
| agtggatatg gaacggcttt cactttcacc atcagcactg tgcaggctga agacctggca | 300 |
| gtttatttct gtcagcagga ttatagttcg ttcggagggg ggaccaagct ggaaataaag | 360 |
| cggaccgtgg ccgcccctc cgtgttcatc ttcccccct ccgacgagca gctgaagtcc | 420 |
| ggcaccgcct ccgtggtgtg cctgctgaac aacttctacc ccggggaggc caaggtgcag | 480 |
| tggaaggtgg acaacgccct gcagtccggc aactcccagg agtccgtgac cgagcaggac | 540 |
| tccaaggact ccacctactc cctgtcctcc accctgaccc tgtccaaggc cgactacgag | 600 |
| aagcacaagg tgtacgcctg cgaggtgacc caccagggcc tgtcctcccc cgtgaccaag | 660 |
| tccttcaacc ggggcgagtg ctag | 684 |

<210> SEQ ID NO 20
<211> LENGTH: 1386
<212> TYPE: DNA
<213> ORGANISM: Artificial sequence
<220> FEATURE:
<223> OTHER INFORMATION: ch3F8-IgG4 heavy chain

<400> SEQUENCE: 20

| | |
|---|---|
| atgggctggt cctgcatcat cctgttcctg gtgccaccg ccaccggcca ggtgcagctg | 60 |
| aaggagtcag gcctggcct ggtggcgccc tcacagagcc tgtccatcac ttgcactgtc | 120 |
| tctgggtttt cagtaaccaa ttatggtgta cactgggttc gccagcctcc aggaaagggt | 180 |
| ctggagtggc tgggagtaat atgggctggt ggaattacaa attataattc ggctttcatg | 240 |
| tccagactga gcatcagcaa agacaactcc aagagtcaag ttttcttaaa aatgaacagt | 300 |

```
ctgcaaattg atgacacagc catgtactac tgtgccagtc ggggggtca ctacggctat      360 gctttggact actggggtca aggaacctca gtcaccgtct cctcagcctc caccaagggc      420
ccctccgtgt tccccctggc ccctgctcc cggtccacct ccgagtccac cgccgccctg      480
ggctgcctgt tgaaggacta cttccccgag cccgtgaccg tgtcctggaa ctccggcgcc      540
ctgacctccg gcgtgcacac cttccccgcc gtgctgcagt cctccggcct gtactccctg      600
tcctccgtgt tgaccgtgcc ctcctcctcc tgggcacca agacctacac ctgcaacgtg      660
gaccacaagc cctccaacac caaggtggac aagcgggtgg agtccaagta cggcccccc      720 tgcccctcct gccccgcccc cgagttcctg ggcggcccct ccgtgttcct gttccccccc      780
aagcccaagg acaccctgat gatctcccgg acccccgagg tgacctgcgt ggtggtggac      840
gtgtcccagg aggaccccga ggtgcagttc aactggtacg tggacggcgt ggaggtgcac      900
aacgccaaga ccaagccccg ggaggagcag ttcaactcca cctacgggt ggtgtccgtg      960 ctgaccgtgc tgcaccagga ctggctgaac ggcaaggagt acaagtgcaa ggtgtccaac     1020
aagggcctgc cctcctccat cgagaagacc atctccaagg ccaagggcca gccccgggag     1080
ccccaggtgt acaccctgcc ccctcccag gaggagatga ccaagaacca ggtgtccctg     1140
acctgcctgg tgaagggctt ctaccccctcc gacatcgccg tggagtggga gtccaacggc     1200
cagcccgaga caactacaa gaccaccccc ccgtgctgg actccgacgg ctccttcttc     1260
ctgtactccc ggctgaccgt ggacaagtcc cggtggcagg agggcaacgt gttctcctgc     1320
tccgtgatgc acgaggccct gcacaaccac tacacccaga gtccctgtc cctgtccctg     1380 ggcaag                                                               1386

<210> SEQ ID NO 21
<211> LENGTH: 684
<212> TYPE: DNA
<213> ORGANISM: Artificial sequence
<220> FEATURE:
<223> OTHER INFORMATION: hu3F8-H3L3 light chain

<400> SEQUENCE: 21
atgggctggt cctgcatcat cctgttcctg gtggccaccg ccaccggctc tatcgtcatg       60
actcagaccc ctgccttcct gctggtgtcc gctggagagc gtgtcactat cacttgtcgt      120
gcctcacaga gcgtgtctaa cgacgtgaca tggtaccagc agaaggccgg tcaggctccc      180
agactgctga tctactctgc aagtaatagg tatactggca ttcctgcccg gttctcaggc      240
tccggatatg gaaccgagtt cacctttaca atctccagcg tgcagagcga agattttgct      300
gtctattttt gccagcagga ttattcatca ttcggcggcg gtactaaact ggaaattaag      360
cgcaccgtgg ccgcccctcc cgtgttcatc ttccccccct ccgacgagca gctgaagtcc      420
ggcaccgcct ccgtggtgtg cctgctgaac aacttctacc ccggggaggc caaggtgcag      480
tggaaggtgg acaacgccct gcagtccggc aactcccaga gtccgtgac cgagcaggac      540 tccaaggact ccacctactc cctgtcctcc accctgaccc tgtccaaggc cgactacgag      600
aagcacaagg tgtacgcctg cgaggtgacc caccagggcc tgtcctcccc cgtgaccaag      660
tccttcaacc ggggcgagtg ctag                                             684

<210> SEQ ID NO 22
<211> LENGTH: 1398
<212> TYPE: DNA
<213> ORGANISM: Artificial sequence
<220> FEATURE:
```

<223> OTHER INFORMATION: hu3F8-H3L3 heavy chain

<400> SEQUENCE: 22

```
atgggctggt cctgcatcat cctgttcctg gtggccaccg ccaccggcca ggtgcagctg      60
gtcgaaagcg ggcctggtct ggtccagcct ggtcgttctc tgcgtctgac ttgtgccgtg     120
tccgggttct ccgtcactaa ctacggagtg cactgggtca gacagccacc tgggaagggt     180
ctggagtggc tgggagtgat ctgggcaggc ggaattacca actacaattc cgccttcatg     240
agcaggctga ccatctctaa ggacaacagt aaaaatacag tgtatctgca gatgaattcc     300
ctgagggccg aagatacagc tgtctactat tgcgcttctc ggggcggtca ctacggttac     360
gctctggact actggggtca ggggactctg gtcactgtca gcgcgcctc caccaagggc      420
ccatcggtct tccccctggc accctcctcc aagagcacct ctgggggcac agcggccctg     480
ggctgcctgg tcaaggacta cttccccgaa ccggtgacgg tgtcgtggaa ctcaggcgcc     540
ctgaccagcg gcgtgcacac cttcccggcc gtcctacagt cctcaggact ctactccctc     600
agcagcgtgg tgaccgtgcc ctccagcagc ttgggcaccc agacctacat ctgcaacgtg     660
aatcacaagc ccagcaacac caaggtggac aagagagttg agcccaaatc ttgtgacaaa     720
actcacacat gcccaccgtg cccagcacct gaactcctgg ggggaccgtc agtcttcctc     780
ttccccccaa acccaagga caccctcatg atctcccgga cccctgaggt cacatgcgtg     840
gtggtggacg tgagccacga agaccctgag gtcaagttca actggtacgt ggacggcgtg     900
gaggtgcata tgccaagac aaagccgcgg gaggagcagt acaacagcac gtaccgtgtg     960
gtcagcgtcc tcaccgtcct gcaccaggac tggctgaatg gcaaggagta caagtgcaag    1020
gtctccaaca aagccctccc agccccatc gagaaaacca tctccaaagc caagggcag     1080
ccccgagaac cacaggtgta caccctgccc ccatcccggg atgagctgac caagaaccag    1140
gtcagcctga cctgcctggt caaaggcttc tatcccagcg acatcgccgt ggagtgggag    1200
agcaatgggc agccggagaa caactacaag accacgcctc ccgtgctgga ctccgacggc    1260
tccttcttcc tctacagcaa gctcaccgtg gacaagagca ggtggcagca ggggaacgtc    1320
ttctcatgct ccgtgatgca tgaggctctg cacaaccact acacgcagaa gagcctctcc    1380
ctgtctccgg gtaaatga                                                  1398
```

<210> SEQ ID NO 23
<211> LENGTH: 518
<212> TYPE: PRT
<213> ORGANISM: Artificial sequence
<220> FEATURE:
<223> OTHER INFORMATION: (hu3F8-LC) - (huOKT3-scFv)

<400> SEQUENCE: 23

```
Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95
```

```
Gln Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys Gly Gly Gly Gly Ser Gly Gly Gly Gly Ser Gln Val Gln
    210                 215                 220

Leu Val Gln Ser Gly Gly Gly Leu Thr Leu Ser Lys Ala Asp Tyr Glu
225                 230                 235                 240

Lys His Lys Val Tyr Ala Cys Glu Val Thr His Gln Gly Leu Ser Ser
                245                 250                 255

Pro Val Thr Lys Ser Phe Asn Arg Gly Glu Cys Gly Gly Gly Gly Ser
            260                 265                 270

Gly Gly Gly Gly Ser Gln Val Gln Leu Val Gln Ser Gly Gly Gly Val
        275                 280                 285

Val Gln Pro Gly Arg Ser Leu Arg Leu Ser Cys Lys Ala Ser Gly Tyr
    290                 295                 300

Thr Phe Thr Arg Tyr Thr Met His Trp Val Arg Gln Ala Pro Gly Lys
305                 310                 315                 320

Cys Leu Glu Trp Ile Gly Tyr Ile Asn Pro Ser Arg Gly Tyr Thr Asn
                325                 330                 335

Tyr Asn Gln Lys Phe Lys Asp Arg Phe Thr Ile Ser Arg Asp Asn Ser
            340                 345                 350

Lys Asn Thr Ala Phe Leu Gln Met Asp Ser Leu Arg Pro Glu Asp Thr
        355                 360                 365

Gly Val Tyr Phe Cys Ala Arg Tyr Tyr Asp Asp His Tyr Cys Leu Asp
    370                 375                 380

Tyr Trp Gly Gln Gly Thr Pro Val Thr Val Ser Ser Gly Gly Gly Gly
385                 390                 395                 400

Ser Gly Gly Gly Gly Ser Gly Gly Gly Gly Ser Asp Ile Gln Met Thr
                405                 410                 415

Gln Ser Pro Ser Ser Leu Ser Ala Ser Val Gly Asp Arg Val Thr Ile
            420                 425                 430

Thr Cys Ser Ala Ser Ser Ser Val Ser Tyr Met Asn Trp Tyr Gln Gln
        435                 440                 445

Thr Pro Gly Lys Ala Pro Lys Arg Trp Ile Tyr Asp Thr Ser Lys Leu
    450                 455                 460

Ala Ser Gly Val Pro Ser Arg Phe Ser Gly Ser Gly Ser Gly Thr Asp
465                 470                 475                 480

Tyr Thr Phe Thr Ile Ser Ser Leu Gln Pro Glu Asp Ile Ala Thr Tyr
                485                 490                 495

Tyr Cys Gln Gln Trp Ser Ser Asn Pro Phe Thr Phe Gly Cys Gly Thr
            500                 505                 510
```

Lys Leu Gln Ile Thr Arg
      515

<210> SEQ ID NO 24
<211> LENGTH: 524
<212> TYPE: PRT
<213> ORGANISM: Artificial sequence
<220> FEATURE:
<223> OTHER INFORMATION: (hu3F8-LC) - (C8.2.5-scFv)

<400> SEQUENCE: 24

Glu Ile Val Met Thr Gln Thr Pro Ala Thr Leu Ser Val Ser Ala Gly
1               5                   10                  15

Glu Arg Val Thr Ile Thr Cys Lys Ala Ser Gln Ser Val Ser Asn Asp
            20                  25                  30

Val Thr Trp Tyr Gln Gln Lys Pro Gly Gln Ala Pro Arg Leu Leu Ile
        35                  40                  45

Tyr Ser Ala Ser Asn Arg Tyr Ser Gly Val Pro Ala Arg Phe Ser Gly
    50                  55                  60

Ser Gly Tyr Gly Thr Glu Phe Thr Phe Thr Ile Ser Ser Val Gln Ser
65                  70                  75                  80

Glu Asp Phe Ala Val Tyr Phe Cys Gln Gln Asp Tyr Ser Ser Phe Gly
                85                  90                  95

Gln Gly Thr Lys Leu Glu Ile Lys Arg Thr Val Ala Ala Pro Ser Val
            100                 105                 110

Phe Ile Phe Pro Pro Ser Asp Glu Gln Leu Lys Ser Gly Thr Ala Ser
        115                 120                 125

Val Val Cys Leu Leu Asn Asn Phe Tyr Pro Arg Glu Ala Lys Val Gln
    130                 135                 140

Trp Lys Val Asp Asn Ala Leu Gln Ser Gly Asn Ser Gln Glu Ser Val
145                 150                 155                 160

Thr Glu Gln Asp Ser Lys Asp Ser Thr Tyr Ser Leu Ser Ser Thr Leu
                165                 170                 175

Thr Leu Ser Lys Ala Asp Tyr Glu Lys His Lys Val Tyr Ala Cys Glu
            180                 185                 190

Val Thr His Gln Gly Leu Ser Ser Pro Val Thr Lys Ser Phe Asn Arg
        195                 200                 205

Gly Glu Cys Gly Gly Gly Gly Ser Gly Gly Gly Gly Ser Ala Ser His
    210                 215                 220

Val Lys Leu Gln Glu Ser Gly Pro Leu Thr Leu Ser Lys Ala Asp Tyr
225                 230                 235                 240

Glu Lys His Lys Val Tyr Ala Cys Glu Val Thr His Gln Gly Leu Ser
                245                 250                 255

Ser Pro Val Thr Lys Ser Phe Asn Arg Gly Glu Cys Gly Gly Gly Gly
            260                 265                 270

Ser Gly Gly Gly Gly Ser Ala Ser His Val Lys Leu Gln Glu Ser Gly
        275                 280                 285

Pro Gly Leu Val Gln Pro Ser Gln Ser Leu Ser Leu Thr Cys Thr Val
    290                 295                 300

Ser Gly Phe Ser Leu Thr Asp Tyr Gly Val His Trp Val Arg Gln Ser
305                 310                 315                 320

Pro Gly Lys Gly Leu Glu Trp Leu Gly Val Ile Trp Ser Gly Gly Gly
                325                 330                 335

Thr Ala Tyr Asn Thr Ala Leu Ile Ser Arg Leu Asn Ile Tyr Arg Asp
            340                 345                 350

-continued

```
Asn Ser Lys Asn Gln Val Phe Leu Glu Met Asn Ser Leu Gln Ala Glu
        355                 360                 365

Asp Thr Ala Met Tyr Tyr Cys Ala Arg Arg Gly Ser Tyr Pro Tyr Asn
    370                 375                 380

Tyr Phe Asp Ala Trp Gly Cys Gly Thr Thr Val Thr Val Ser Ser Gly
385                 390                 395                 400

Gly Gly Gly Ser Gly Gly Gly Gly Ser Gly Gly Gly Gly Ser Gln Ala
                405                 410                 415

Val Val Ile Gln Glu Ser Ala Leu Thr Thr Pro Pro Gly Glu Thr Val
            420                 425                 430

Thr Leu Thr Cys Gly Ser Ser Thr Gly Ala Val Thr Ala Ser Asn Tyr
        435                 440                 445

Ala Asn Trp Val Gln Glu Lys Pro Asp His Cys Phe Thr Gly Leu Ile
    450                 455                 460

Gly Gly His Asn Asn Arg Pro Pro Gly Val Pro Ala Arg Phe Ser Gly
465                 470                 475                 480

Ser Leu Ile Gly Asp Lys Ala Ala Leu Thr Ile Ala Gly Thr Gln Thr
                485                 490                 495

Glu Asp Glu Ala Ile Tyr Phe Cys Ala Leu Trp Tyr Ser Asp His Trp
            500                 505                 510

Val Ile Gly Gly Gly Thr Arg Leu Thr Val Leu Gly
            515                 520
```

ANTI-GD2 ANTIBODIES

Monoclonal antibody (MoAb) therapy is an accepted treatment modality for cancers, with five MoAbs having received FDA approval for solid tumors in adults, including colorectal and breast cancer, non small cell lung cancer, squamous cell carcinoma, and melanoma (Boyiadzis et al., 2008, Expert Opin Biol Ther 8, 1151-8; Yan et al., 2008, Cancer J 14, 178-83). This modality, however, has remained inadequately exploited for the treatment of pediatric cancers. Unlike chemotherapy or radiation, MoAb therapy is not myelosuppressive and genotoxic, generally with few long term toxicities. These are critical considerations for young children. More importantly, MoAb is effective against metastatic cancer in blood, bone marrow and bone, typically found in high risk neuroblastoma (NB). As a class of agents, the pharmacokinetics and toxicities of human or humanized IgG1 antibodies have been extensively studied. In addition, antibodies can carry cytotoxic payloads, whether immune based, radioisotopes, toxins or enzymes, thereby increasing the options for targeted therapy.

Neuroblastoma (NB) is the most common extracranial solid tumor of childhood. In ~50% of cases, curative strategies must tackle both soft tissue mass and metastases in the bone marrow (BM). Dose-intensive chemotherapy improves tumor respectability, and post-surgical irradiation reduces the risk of relapse in the primary site to <10% (Kushner et al., 2001, J Clin Oncol 19, 2821-8). However, BM disease, as evidenced by histology or metaiodobenzylguanidine (MIBG) scan, often persists and forebodes a lethal outcome (Matthay et al., 2003, J Clin Oncol 21, 2486-91; Schmidt et al., 2008, Eur J Cancer 44, 1552-8). In addition, osteomedullary relapse is common, despite achieving near complete remission after induction therapy. Attempts at treatment intensification have met with both acute and long-term side effects, both of grave concern for young patients. There is a scarcity of promising new agents, and to date, few if any target/pathway-specific small molecules have shown major clinical benefit in patients with NB, although many promising leads continue to accumulate. With a cure rate of <30% at toxicity limits among stage 4 patients diagnosed at >18 months of age, there is substantial room for improvement (Pearson et al., 2008, Lancet Oncol 9, 247-56).

Several factors make NB well suited for MoAb targeted immunotherapy. First, MoAb mediates highly efficient antibody-dependent cellular cytotoxicity (ADCC) of NB in the presence of human white cells. Second, MoAb induces complement-mediated cytotoxicity (CMC) of NB cells, which lack decay accelerating factor CD55 (Cheung et al., 1988, J Clin Invest 81, 1122-8) and homologous restriction factor CD59 (Chen et al., 2000, Cancer Res 60, 3013-8). Complement deposition on NB cells enhances ADCC through activation of the iC3b receptor on neutrophils (Kushner and Cheung, 1992, Blood 79, 1484-90, Metelitsa et al., 2002, Blood 99, 4166-73), available even after dose-intensive or myeloablative chemotherapy plus stem cell transplantation, if colony stimulating factors are given (Mackall, C L, 2000, Stem Cells 18, 10-8). Third, the use of intensive chemotherapy (standard of care for NB) to achieve clinical remission causes prolonged lymphopenia and immunosuppression (Mackall et al., 2000, Blood 96, 754-762), such that patients are less likely to reject murine, chimeric or humanized MoAbs (Kushner et al., 2007, Pediatr Blood Cancer 48, 430-4).

GD2 is a disialoganglioside abundant on tumors of neuroectodermal origin, including neuroblastoma and melonoma with highly restricted expression in normal tissues. At least two antibody families have been tested clinically, i.e. 3F8 (Cheung et al., 1985, Cancer Res 45, 2642-9) and 14.18 (Mujoo et al., 1989, Cancer Res 49, 2857-61). Chimeric ch14.18 consists of the variable region of murine MoAb 14.18 and the constant regions of human IgG1-K (Gillies et al., 1989, J Immunol Methods 125, 191-202). It demonstrates ADCC and CMC of NB and melanoma cells in vivo (Barker et al., 1991, Cancer Res 51, 144-9; Barker and Reisfeld, 1993, Cancer Res. 52, 362-7; Mueller et al., 1990, PNAS USA 87, 5702-05 0. Based on encouraging clinical responses in phase I studies, ch14.18 was tested in large phase II studies as consolidation therapy for stage 4 NB (German NB90 and NB97 studies). For the 166 patients >12 months at diagnosis, even though event-free survival (EFS) was similar in patients receiving ch14.18 when compared to patients on maintenance chemotherapy, overall survival (OS) was improved, and the rate of BM relapse reduced in patients treated with ch14.18 (Simon et al., 2004, J Clin Oncol 22, 3549-57). In 2001, the Children's Oncology Group (COG) initiated a randomized phase III trial to study the efficacy of the combination of ch14.18 with GMCSF and IL-2 in preventing NB relapse in patients in complete remission (CR) after autologuous stem-cell transplantation (ASCT) (ClinicalTrials.gov NCT00026312) (Gilman et al., J Clin Oncol 27:85-91, 2009), where a significant improvement in progression free survival (PFS) and OS at 2 years was found (Yu et al., N Engl J Med 363:1324-1334, 2010). 3F8, a murine IgG3 MoAb specific for GD2, induces cell death, and mediates efficient ADCC and CMC against NB in vitro (Cheung et al., 2007, supra). Among patients with chemoresistant marrow disease despite dose-intensive induction plus an aggressive salvage regimen, 80% achieved BM remission usually after 1 to 2 cycles of 5-day antibody plus GM-CSF therapy (Kushner et al., 2007, Proc Amer Soc Clin Oncol 25, 526s). Given the activity of m3F8 against chemoresistant marrow disease, the use of m3F8 was expanded to patients in their first remission with encouraging results. These favorable clinical outcomes in children could be improved if m3F8 is given as maintenance therapy over the first 3-5 years of highest recurrence risk. However, human anti-mouse antibody response (HAMA) is a limiting factor when the immune system recovers when chemotherapy is finished. One strategy to reduce HAMA is to chimerize or humanize 3F8.

Therefore, there is a need for a chimeric and/or humanized 3F8 antibody able to bind GD2 with high affinity, superior to m3F8, and able to mediate antibody-dependent cellular cytotoxicity thereby allowing long term antibody therapy in order to reduce disease recurrence.

Herein described is the engineering and isolation of chimeric 3F8 (ch3F8-IgG1) and humanized 3F8 (hu3F8-IgG1 and hu3F8-IgG4). These antibodies were made using standard recombinant methods, and selected for high expression by CHO-DG44 cell lines in serum free medium. A special glycoform of hu3F8-IgG1n (also called hu3F8-IgG1-MAGE1.5) was produced using CHO-Mage1.5 cell line. This special glycoform has no fucose, and only terminal mannose and N-acetylglucose or glucose. Measured using surface Plasmon resonance used by Biacore systems, chimeric 3F8 and humanized 3F8 maintained a $K_D$ similar to that of m3F8. In contrast to other anti-GD2 antibodies, m3F8, ch3F8-IgG1, ch3F8-IgG4, hu3F8-IgG1, hu3F8-IgG4 and hu3F8-IgG1n had substantially slower $k_{off}$, which translated into a slower wash off in vitro. Like m3F8, both chimeric and humanized 3F8 inhibited cell growth in vitro, not typical for other anti-GD2 antibodies. Similar measurements indicated that chimeric and humanized IgG1 antibodies have more favorable $K_D$ compared to 14.G2a. Both blood mononuclear cell (PBMC)-ADCC and neutrophil (PMN)-ADCC of ch3F8-IgG1, hu3F8-IgG1, and hu3F8-IgG1n were superior (10 to >1000 fold) to that of m3F8, while CMC was inferior. This superiority was consistently observed in ADCC assays, irrespective of donors or if NK92 transfected with human CD16 or CD32 were used as killers. For CD16 mediated ADCC, hu3F8-IgG1n was 10-40 fold better compared to hu3F8-IgG1. PBMC-ADCC and CMC activity was greatly reduced with hu3F8-IgG4 when compared to m3F8. Crossreactivity with other gangliosides were similar to that of m3F8. Using $^{131}$I labeled antibodies in biodistribution, hu3F8 forms had tumor to normal tissue ratios comparable to those of m3F8. Hu3F8-IgG1 showed superior anti-tumor effect against NB xenografts when compared to m3F8.

Also described herein are novel hu3F8 antibodies, hu3F8H3L3, which have been designed to have enhanced stability profiles using an experimentally derived crystal structure of m3F8 in combination with computational analysis using force methods.

SUMMARY OF THE INVENTION

Humanizing strategies share the premise that replacement of amino acid residues that are characteristic of murine sequences with residues found in the correspondent positions of human antibodies will reduce the immunogenicity in humans of the resulting antibody in humans. However, replacement of sequences between species usually results in reduction of antibody binding to its antigen, and loss of affinity. The art of humanization therefore lies in balancing replacement of the original murine sequence to reduce immunogenicity with the need for the humanized molecule to retain sufficient antigen binding to be therapeutically useful.

The present invention provides engineered and isolated chimeric and humanized 3F8 antibodies, having at least one CDR sequence derived from the m3F8, as well as antibody compositions, glycoforms of the antibody, antibodies with enhanced stability, antibodies with enhanced binding to Fc receptors, antibodies with enhanced affinity to GD2, bispecific antibodies engineered to express a second distinct binding site or a bispecific T-cell engager, or use of the Fv fragments of any of the antibodies of the present invention in modular IgG construction for bispecific, bispecific T-cell engaging (BiTE) antibodies, trispecific or multispecific antibodies. These antibodies and encoding or complementary nucleic acids, vectors, host cells, compositions, formulations, devices, transgenic animals, transgenic plants related thereto, and methods of making and using thereof, as described and enabled herein, in combination with what is known in the art are part of the present invention. The hu3F8-IgG1 antibody of the invention has significantly more PMN-ADCC and PBMC-ADCC activities than m3F8 or any other known anti-GD2 antibodies (including 14G.2a, ch14.18 or ME361), with intact complement mediated cytotoxicity (CMC), although less than m3F8. This superiority was consistently observed in ADCC assays irrespective of donors or if NK92 transfected with human CD16 or CD32 were used as killers. This was important since ADCC is the proven mechanism for anti-tumor effects of MoAb in patients in general. Both hu3F8-IgG1 and hu3F8-IgG1n, a glycoform of hu3F8-IgG1, showed superior anti-tumor effect against neuroblastoma NB) xenografts when compared with m3F8. The IgG4 form of the antibody showed reduced effector function and is effective for blocking pain side effects of anti-GD2 antibody therapy. Hu3F8-IgG1-DEL with a triple mutation in the heavy chain (or S239D/I332E/A330L) showed increased affinity to the Fc receptor (FcR). Analysis of 3F8:GD2 interaction resulted in design of a 3F8 antibody with mutation in the heavy chain producing huH1I-gamma-1 and huH3I-gamma-1 heavy chains thermodynamically calculated to confer increased affinity to GD2.

The present invention provides at least one isolated engineered chimeric, ch3F8, or humanized, hu3F8, antibody as described herein. The antibody according to the present invention includes any protein or peptide molecule that comprises at least one complementarity determining region (CDR) of a heavy or light chain or a ligand binding portion thereof, derived from m3F8, in combination with a heavy chain or light chain constant region, a framework region, or any portion thereof, that can be incorporated into an antibody of the present invention. In one embodiment the invention is directed to a hu3F8 antibody comprising a light chain and a heavy chain described herein, each of the chains comprising at least part of a human constant region and at least part of a variable region derived from m3F8 which has specificity to GD2, said antibody binding with high affinity to GD2 and mediating a desired effect, e.g. inhibiting cell growth in vitro, blocking pain side effects due to anti-GD2 antibody therapy, to name a few. The invention also includes fragments or a derivative of such an antibody, such as one or more portions of the antibody chain, such as the heavy chain constant, joining, diversity or variable regions, or the light chain constant, joining or variable regions. The antibodies can be of any class such as IgG, IgM, or IgA or any subclass such as IgG1, IgG2a, IgG4, and other subclasses known in the art. Antibodies useful in the present invention also include antigen-binding antibody fragments of the antibodies of the present invention including, but are not limited to, Fab, Fab' and F(ab')$_2$, Fd, single-chain Fvs (scFv), single-chain antibodies, disulfide-linked or disulfide-stabilized Fvs (sdFv or dsFv). The invention also includes single-domain antibodies comprising either a VL or VH domain. Further, the antibodies can be produced by any method, such as phage display, or produced in any organism, egg, or cell line, including bacteria, insect, yeast (fungi), mammal or other type of cell or cell line which produces antibodies with desired characteristics, such as humanized antibodies. The antibodies can also be formed by combining a Fab portion and a Fc region from different species, or by keeping the complementarity-determining regions and modifying the framework regions to that of another species.

The antibody can comprise at least one specified portion of at least one complementarity determining region (CDR) (e.g., CDR1, CDR2 or CDR3 of the heavy or light chain variable region) derived from a m3F8 or hu3F8 (as such terms are defined herein), and/or at least one constant or variable framework region or any portion thereof. The antibody amino acid sequence can further optionally comprise at least one specified substitution, insertion or deletion as described herein or as known in the art.

Preferred antibodies of the present invention include ch3F8-IgG1, ch3F8-IgG4, hu3F8-H1L1-IgG1, hu3F8-H2L2-IgG1, hu3F8-H1L2-IgG1, hu3F8-H2L1-IgG1, hu3F8-IgG4, hu3F8IgG1n, Hu3F8-IgG1-DEL, hu3F8H1L1S (hu3F8-IgG1 light chain interface enhanced), hu3F8H3L3 (hu3F8-IgG1 heavy and light chain stability enhanced), hu3F8H3L3S (interface and stability enhanced), hu3F8H1-1-gamma-1 (hu3F8-IgG1 affinity enhanced), hu3F8H3-1-gamma-1 (hu3F8-IgG1 stability and affinity enhanced) as well as fragments and regions thereof.

In one embodiment, the present invention relates to chimeric monoclonal antibodies having binding specificity for GD2, wherein the antibody ch3F8-IgG1 comprises heavy chain domain SEQ ID NO:1, and a light chain variable domain SEQ ID NO:2. In another embodiment, the antibody ch3F8-IgG4 comprises the heavy chain variable domain of SEQ ID NO:3 and a light chain domain of SEQ ID NO:2. Such chimeric antibodies are derived from murine 3F8 antibody, in certain embodiments, the chimeric antibodies comprise a heavy chain whose complementarity determining regions (CDR) 1, 2 and 3 are defined by amino acid residues 31-35, 50-64 and 98-108, respectively, of SEQ ID NO:1. In certain embodiments, the chimeric antibodies comprise a light chain whose CDRs 1, 2 and 3 are defined by amino acid residues 24-34, 50-56 and 89-95, respectively, of SEQ ID NO:2. In certain embodiments, the chimeric antibodies comprise a heavy chain whose framework regions (FR) 1, 2, 3 and 4 are defined by amino acid residues 1-30, 36-49, 65-97 and 109-120, respectively, of SEQ ID NO:1. In certain embodiments, the chimeric antibodies comprise a light chain whose framework regions (FR) 1, 2, 3 and 4 are defined by amino acid residues 1-23, 35-49, 57-88 and 96-108, respectively, of SEQ ID NO:2.

In one embodiment, the present invention relates to humanized monoclonal antibodies having binding specificity for GD2, wherein the antibody hu3F8-H1L1-IgG1 comprises heavy chain variable domain of SEQ ID NO:4 and light chain variable domain of SEQ ID NO:5, wherein hu3F8H2L2-IgG1 comprises heavy chain variable domain SEQ ID NO:6 and light chain variable domain SEQ ID NO:7, wherein hu3F8-H1L1-IgG4 comprises heavy chain variable domain SEQ ID NO:8 and light chain variable domain SEQ ID NO:5 or 7. Such humanized antibodies are derived from the humanization of the murine 3F8 antibody. In certain embodiments, the humanized antibodies comprise a heavy chain whose complementarity determining regions (CDR) 1, 2 and 3 are defined by amino acid residues 31-35, 50-64 and 98-108, respectively, of SEQ ID NO:4, 6 or 8. In certain embodiments, the humanized antibodies comprise a light chain whose CDRs 1, 2 and 3 are defined by amino acid residues 24-34, 50-56 and 89-95, respectively, of SEQ ID NO:5 or 7.

The present invention also relates to Anti-GD2 humanized antibodies engineered with modified carbohydrate composition, hu3F8-IgG1n, with increased effector function.

The present invention also relates to Hu3F8-IgG1-DEL antibody with a triple mutation DEL (S239D/A330L/I332E) in the heavy chain of hu3F8-IgG1 or hu3F8-IgG1n. Hu3F8-IgG1-DEL comprises substitutions in the heavy chain consisting of S239D, A330L and I332E of SEQ ID NO: 4, 6, or 8.

The present invention also relates to hu3F8H3L3 derived from computational analysis of the crystal structure and adjustment of the amino acid sequence by backmutation and forward mutation to enhance stability of the antibody. The sequence of the stability enhanced huH3 heavy chain is disclosed in SEQ ID NO:9, with the huL3 light chain in SEQ ID NO:10. These mutations can also be introduced into a heavy chain sequence alone or in combination with other mutations the heavy chain described herein.

An additional mutation to enhance stability at the VH-VL interface was added at position 43 in the light chain resulted in huL3S. Therefore, huL3S comprises a substitution consisting of Ala43Ser of SEQ ID NO:10. When this change to Serine at position 43 is incorporated in the light chain of hu3F8-IgG1, that light chain is referred to as huL1S. Similarly, huL1S comprises a substitution consisting of Ala43Ser of SEQ ID NO: 5 or 7.

Computational modeling further showed that substitution of the Gly at position 54 to Ile in the CDR3 of the heavy chain would change the shape of the binding pocket and increase the contact with the GD2 ligand. Adding this mutation Gly54Ile to the CDR regions of the sequences of huH1-IgG1 and huH3-IgG1 resulted in huH1I-gamma1 and huH3I-gamma, respectively. Therefore, huHI-gamma1 comprises a Gly54Ile substitution in SEQ ID NO:4, 6, or 8. huH3I-gamma1 comprises a Gly54Ile substitution in SEQ ID NO:9.

Preferred antibodies of the present invention are those that bind human GD2 and perform the desired function, i.e. effector function, blocking pain, or inhibiting cell growth. Preferred methods for determining monoclonal antibody specificity and affinity by competitive inhibition can be found in Harlow, et al, Antibodies: A Laboratory Manual, Cold Spring Harbor Laboratory Press, Cold Spring Harbor, N.Y., 1988), hereby incorporated by reference thereto. At least one antibody of the invention binds at least one specified epitope specific to human GD2, subunit, fragment, portion or any combination thereof. The epitope can comprise at least one antibody binding region, which epitope is preferably comprised of at least 1-5 sugar residues or ceramide of at least one portion of GD2.

In one aspect, the present invention provides at least one isolated humanized Anti-GD2 antibody, comprising at least one variable region from m3F8, and the nucleic acid sequences encoding same.

In another aspect, the present invention provides at least one isolated mammalian Anti-GD2 antibody, comprising either (i) all of the heavy chain complementarity determining regions (CDR) amino acid sequences derived from m3F8, and the nucleic acid sequences encoding them; or (ii) all of the light chain CDR amino acids sequences from m3F8, and the nucleic acid sequences encoding them.

In another aspect, the present invention provides at least one isolated mammalian Anti-GD2 antibody, comprising at least one heavy chain or light chain CDR having the amino acid sequence derived from m3F8, and the nucleic acid sequences encoding them.

In another aspect the present invention provides at least one isolated chimeric, humanized or CDR-grafted Anti-GD2 antibody, comprising at least one m3F8 CDR, wherein the antibody specifically binds at least one epitope comprising at least 1-5 sugar residues or ceramide of an epitope of human GD2.

In yet another aspect, the present invention provides a diagnostic/detection or therapeutic immunoconjugate comprising an antibody component that comprises any of the 3F8 MoAbs or fragments thereof of the present invention, or an antibody fusion protein or fragment thereof that comprises any of the 3F8 antibodies or fragments thereof of the present invention, wherein the antibody component is bound to at least one diagnostic/detection agent or at least one therapeutic agent.

In still another aspect, the present invention provides a therapeutic immunoconjugate comprising a therapeutic agent that is selected from the group consisting of a radionuclide, boron, gadolinium or uranium atoms, an immunomodulator, such as a cytokine, a stem cell growth factor, a lymphotoxin, such as tumor necrosis factor (TNF), a hematopoietic factor such as an interleukin (IL), a colony stimulating factor (CSF) such as granulocyte-colony stimulating factor (G-CSF) or granulocyte macrophage-colony stimulating factor (GM-CSF)), an interferon (IFN) such as interferons-alpha, -beta or -gamma, and a stem cell growth factor, a hematopoietic factor, erythropoietin, thrombopoietin, an antibody, a hormone, a hormone antagonist, an enzyme, an enzyme inhibitor, a photoactive therapeutic agent, a cytotoxic drug, such as antimitotic, alkylating, antimetabolite, angiogenesis-inhibiting, apoptotic, alkaloid, COX-2-inhibiting and antibiotic agents, a cytotoxic toxin, such as plant, microbial, and animal toxins, and a synthetic variations thereof, an angiogenesis inhibitor, a different antibody and a combination thereof.

In another aspect, the present invention also provides a multivalent, multispecific antibody or fragment thereof comprising one or more antigen-binding sites having affinity toward an antigen recognized by the 3F8 antibody and one or more hapten binding sites having affinity towards epitopes or haptens besides GD2. Preferably, the 3F8 antibody or fragment thereof is chimerized or humanized. Also preferred, the antibody or fragment thereof is fully human or chimerized. In one embodiment, the multivalent, multispecific antibody or fragment thereof comprises a diagnostic/detection or therapeutic agent.

In yet another aspect, the present invention provides a method of delivering a diagnostic/detection agent, a therapeutic agent, or a combination thereof to a target, comprising: (i) administering to a subject a multivalent, multispecific antibody or fragment thereof of the present invention; (ii) waiting a sufficient amount of time for an amount of the non-binding protein to clear the subject's blood stream; and (iii) administering to said subject a carrier molecule comprising a diagnostic/detection agent, a therapeutic agent, or a combination thereof, that binds to a binding site of said antibody. The diagnostic/detection agent or said therapeutic agent is selected from the group comprising isotopes, dyes, chromagens, contrast agents, drugs, toxins, cytokines, enzymes, enzyme inhibitors, hormones, hormone antagonists, growth factors, radionuclides, metals, liposomes, nanoparticles, RNA or DNA. The second specificity also includes hapten(s) conjugated to any from the group of agents described. These haptens include, but not limited to biotin and its derivatives, DOTA and its derivatives, DTPA and its derivatives, fluorescein and its derivatives, histamine and its derivatives, Deferoxamine and its derivatives).

In any of the methods of the present invention, the subject is preferably a mammal, such as a human or domestic pet.

In another embodiment of the present invention is a method of treating or identifying diseased tissues in a subject, comprising: (A) administering to said subject a bi-specific antibody or antibody fragment having at least one arm that specifically binds a diseased tissue-associated marker and at least one other arm that specifically binds a targetable conjugate, wherein said diseased tissue-associated marker is an antigen recognized by the 3F8 MoAb; (B) optionally, administering to said subject a clearing composition, and allowing said composition to clear non-localized antibodies or antibody fragments from circulation; and (C) administering to said subject a first targetable conjugate which comprises a carrier portion which comprises or bears at least one epitope recognizable by said at least one other arm of said bi-specific antibody or antibody fragment, and one or more conjugated therapeutic or diagnostic agents.

Preferably, at least one arm that specifically binds a targeted tissue is a human, chimeric or humanized Anti-GD2 antibody or a fragment of a human, chimeric or humanized Anti-GD2 antibody. A preferred embodiment is the use of the 3F8 MoAb in such applications as a chimeric, humanized, or human antibody, as described herein.

In yet another aspect, the present invention provides a method for detecting or treating tumors expressing an antigen recognized by a 3F8 MoAb in a mammal, comprising: (A) administering an effective amount of a bispecific antibody or antibody fragment comprising at least one arm that specifically binds a targeted tissue and at least one other arm that specifically binds a targetable conjugate, wherein said one arm that specifically binds a targeted tissue is a 3F8 antibody or fragment thereof; and (B) administering a targetable conjugate. The targetable conjugate can be selected from the group consisting of (i) DOTA-Phe-Lys(HSG)-D-Tyr-Lys(HSG)-NH2; (ii) Ac-Lys(HSG)D-Tyr-Lys(HSG)-Lys(Tscg-Cys)-NH2; (iii) DOTA-D-Asp-D-Lys(HSG)-D-Asp-D-Lys(HSG)-NH2; (iv) DOTA-D-Glu-D-Lys(HSG)-D-Glu-D-Lys(HSG)-NH2; (v) DOTA-D-Tyr-D-Lys(HSG)-D-Glu-D-Lys(HSG)-NH2; (vi) DOTA-D-Ala-D-Lys(HSG)-D-Glu-D-Lys(HSG)-NH2; (vii) DOTA-D-Phe-D-Lys(HSG)-D-Tyr-D-Lys(HSG)-NH2; (viii) Ac-D-Phe-D-Lys(DOTA)-D-Tyr-D-Lys(DOTA)-NH2; (ix) Ac-D-Phe-D-Lys(DTPA)-D-Tyr-D-Lys(DTPA)-NH2; (x) Ac-D-Phe-D-Lys(Bz-DTPA)-D-Tyr-D-Lys(Bz-DTPA)-NH2; (xi) Ac-D-Lys(HSG)-D-Tyr-D-Lys(HSG)-D-Lys(Tscg-Cys)-NH2; (xii) DOTA-D-Phe-D-Lys(HSG)-D-Tyr-D-Lys(HSG)-D-Lys(Tscg-Cys)-NH2; (xiii) (Tscg-Cys)-D-Phe-D-Lys(HSG)-D-Tyr-D-Lys(HSG)-D-Lys(DOTA)-NH2; (xiv) Tscg-D-Cys-D-Glu-D-Lys(HSG)-D-Glu-D-Lys(HSG)-NH2; (xv) (Tscg-Cys)-D-Glu-D-Lys(HSG)-D-Glu-D-Lys(HSG)-NH2; (xvi) Ac-D-Cys-D-Lys(DOTA)-D-Tyr-D-Ala-D-Lys(DOTA)-D-Cys-NH2; (xvii) Ac-D-Cys-D-Lys(DTPA)-D-Tyr-D-Lys(DTPA)-NH2; (xviii) Ac-D-Lys(DTPA)-D-Tyr-D-Lys(DTPA)-D-Lys(Tscg-Cys)-NH2; (xix) Ac-D-Lys(DOTA)-D-Tyr-D-Lys(DOTA)-D-Lys(Tscg-Cys)-NH2; fluororescein and its derivatives; desferrioxamine and its derivatives.

In another aspect, the present invention provides a method of targeting wherein the method comprises: (A) injecting a subject who is to undergo such a procedure with a bispecific antibody F(ab)2 or F(ab')2 fragment, or single-chain Fv fragment, wherein the bispecific antibody or fragment has a first antibody binding site which specifically binds to an antigen recognized by an 3F8 MoAb, and has a second antibody binding site which specifically binds to a hapten, and permitting the antibody fragment to accrete at target sites; (B) optionally clearing non-targeted antibody fragments using a clearing agent if the bispecific fragment is not largely cleared from circulation within about 24 hours of injection, and injecting a hapten-modified dextran, or dendrimers, or polymers, which quickly remove nontargeted antibody or fragments into the liver for degradation (C) detecting the presence of the hapten by nuclear imaging or close-range detection of elevated levels of accreted label at the target sites using scanners or probes, within hours of the first injection, and conducting said procedure, wherein said detection is performed without the use of a contrast agent or subtraction agent. In a preferred embodiment, the hapten is labeled with a diagnostic/detection radioisotope, a MRI image-enhancing agent, a fluorescent label or a chemiluminescent label. Fluorescent labels can include rhodamine, fluorescein, renographin, fluorescein isothiocyanate, phycoerytherin, phycocyanin, allophycocyanin, o-phthaldehyde and fluorescamine. Chemiluminescent labels can include luminol, isoluminol, an aromatic acridinium ester, an imidazole, an acridinium salt and an oxalate ester. MRI image-enhancing agents include gadolinium and ferromagnetic substances. Imaging of antibody-hapten localization detects intact tumor cells that carry GD2, which is critical for tumor staging, measurement of tumor response to treatment, detection of early relapse and tumor surveillance. Detection of antibody-hapten localization intraoperatively gives precise location of tumor and uncovers occult sites of disease, to allow complete surgical resection as part of a curative therapy for cancer.

Also considered in the present invention is a multivalent, multispecific antibody or fragment thereof comprising comprising one or more antigen-binding sites having affinity toward an antigen recognized by the 3F8 antibody and one or more hapten binding sites having affinity towards epitopes or haptens on cells (lymphocytes, natural killer cells, neutrophils, myeloid cells, stem cells, neuro stem cells, mesenchymal stem cells, leukemia cells, cytotoxic lymphocytes and B-lymphocytes). These bispecific antibodies or fragments can be administered through various routes, including intravenous, intrathecally, and intratumorally into mammals including humans to target endogenous cells or exogenously infused cells to sites or tissues or cells that carry the antigen GD2. Alternatively, cells can be armed ex vivo using these bispecific antibodies or fragments before administration into mammals including humans.

Also considered in the present invention is the use of sequences of 3F8 or fragments there of, to create chimeric surface receptors specific for GD2 using genetic methods, to redirect cells (lymphocytes, natural killer cells, neutrophils, myeloid cells, stem cells, neuro stem cells, mesenchymal stem cells, leukemia cells, cytotoxic lymphocytes and B-lymphocytes) to GD2 bearing tissues, organs or tumors, both for diagnostic and for therapeutic applications.

The present invention provides, in one aspect, isolated nucleic acid molecules comprising, complementary, or hybridizing to, a polynucleotide encoding the aforementioned specific Anti-GD2 antibodies, comprising at least one specified sequence, domain, portion or variant thereof. In a more specific aspect, the present invention provides nucleotide sequences encoding antibodies of the present invention wherein, wherein the Hu3F8-H1L1-IgG1 (also abbreviated as hu3F8-IgG1) light chain is encoded by SEQ ID NO:11 and the Hu3F8-H1L1-IgG1 heavy chain is encoded by SEQ ID NO:12, wherein Hu3F8-H1L1-IgG4 light chain is encoded by SEQ ID NO:13 and the Hu3F8-H1L1-IgG4 heavy chain is encoded by SEQ ID NO:14, wherein Hu3F8-H1L2-IgG1 light chain L2 is encoded by SEQ ID NO:15 and the Hu3F8-H2L2-IgG1 heavy chain H2 is encoded by SEQ ID NO:16. The heavy and light chains of hu3F8-H1L1-IgG1 are interchangeable with the heavy and light chains of hu3F8-H2L2-IgG1, forming Anti-GD2 antibodies hu3F8-H1L2-IgG1 and hu3F8-H2L1-IgG1. Further nucleotide sequences are provided herein wherein ch3F8-IgG1 light chain is encoded by SEQ ID NO:17 and the ch3F8-IgG1 heavy chain is encoded by SEQ ID NO:18, wherein ch3F8-IgG4 light chain is encoded by SEQ ID NO:19 and the ch3F8-IgG4 heavy chain is encoded by SEQ ID NO:20, and wherein hu3F8H3L3-IgG1 light chain L3 is encoded by SEQ ID NO:21 and heavy chain H3 is encoded by SEQ ID NO:22.

The present invention further provides recombinant vectors comprising said Anti-GD2 antibody nucleic acid molecules, host cells containing such nucleic acids and/or recombinant vectors, as well as methods of making and/or using such antibody nucleic acids, vectors and/or host cells. Thus, the invention comprises isolated nucleic acid encoding at least one isolated mammalian Anti-GD2 antibody or fragment thereof; an isolated nucleic acid vector comprising the isolated nucleic acid, and/or a prokaryotic or eukaryotic host cell comprising the isolated nucleic acid. The host cell can optionally be at least one selected from COS-1, COS-7, HEK293, BHK21, CHO, CHO-S, DG44, BSC-1, Hep G2, 653, SP2/0, 293, HeLa, myeloma, or lymphoma cells, or any derivative, immortalized or transformed cell thereof. Also provided is a method for producing at least one Anti-GD2 antibody, comprising translating the antibody encoding nucleic acid under conditions in vitro, in vivo or in situ, such that the antibody is expressed in detectable or recoverable amounts, including methods that use vectors which allow protein expression to be amplified using growth and survival selection under the control of metabolic pathways or enzymes that include but not limited to dhfr (dihydrofolate reductase) or GS (glutamine synthase).

The present invention also provides at least one method for expressing at least one aforementioned Anti-GD2 antibody in a host cell, comprising culturing a host cell as described herein under conditions wherein at least one Anti-GD2 antibody is expressed in detectable and/or recoverable amounts.

The present invention also provides at least one composition comprising (a) an isolated Anti-GD2 antibody encoding nucleic acid and/or antibody as described herein; and (b) a suitable carrier or diluent. The carrier or diluent can optionally be pharmaceutically acceptable, according to known carriers or diluents. The composition can optionally further comprise at least one further compound, protein or composition. In some of these compositions, the chimeric or humanized antibodies are conjugated to a cytotoxic agent (i.e., an agent that impairs the viability and/or the functions of a cell) such as a cytotoxic drug, a toxin or a radionuclide.

The present invention further provides at least one Anti-GD2 antibody method or composition, for administering a therapeutically effective amount to modulate or treat at least one GD2 related condition in a cell, tissue, organ, animal or patient and/or, prior to, subsequent to, or during a related condition, as known in the art and/or as described herein. Thus, the invention provides a method for diagnosing or treating a GD2 related condition in a cell, tissue, organ or animal, comprising contacting or administering a composition comprising an effective amount of at least one isolated Anti-GD2 antibody or fragment thereof of the invention with, or to, the cell, tissue, organ or animal. The method can optionally further comprise using an effective amount of 0.001-50 mg/kilogram of an Anti-GD2 antibody of the invention to the cells, tissue, organ or animal. The method can optionally further comprise the contacting or the administrating by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrathecal, intra-Ommaya, intravitreous, intraocular, intrasynovial, intrathoracic, intrauterine, intravesical, bolus, vaginal, rectal, buccal, sublingual, intranasal, or transdermal. The method can optionally further comprise administering, prior, concurrently, or after the antibody contacting or administering at least one composition comprising an effective amount of at least one compound or protein or cell selected from at least one of a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromsucula-r blocker, an antimicrobial, an antipsoriatic, a corticosteriod, an anabolic steroid, an erythropoietin, an immunization, an immunoglobulin, antibody or antibody derived conjugates, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog thereof, a cytotoxic or other anti-cancer agent, an anti-metabolite such as methotrexate, an anti-proliferative agent, a cytokine, interleukin, growth factors, a cytokine antagonist, and an anti-TNFα, white cells, T-cells, LAK cells, TIL cells, natural killer (NK) cells, monocytes, NKT cells, engineered T cells or NK cells or monocytes or granulocytes.

The present invention further provides at least one Anti-GD2 antibody method for diagnosing at least one GD2 related condition in a cell, tissue, organ, animal or patient and/or, prior to, subsequent to, or during a related condition, as known in the art and/or as described herein.

The present invention also provides at least one composition, device and/or method of delivery for diagnosing of at least one Anti-GD2 antibody condition, according to the present invention.

Also provided is a composition comprising at least one isolated humanized Anti-GD2 antibody and at least one pharmaceutically acceptable carrier or diluent. The composition can optionally further comprise an effective amount of at least one compound or protein selected from at least one of a detectable label or reporter, a cytotoxic or other anti-cancer agent, an anti-metabolite such as methotrexate, an anti-proliferative agent, a cytokine, or a cytokine antagonist, a TNF antagonist, an antirheumatic, a muscle relaxant, a narcotic, a non-steroid anti-inflammatory drug (NTHE), an analgesic, an anesthetic, a sedative, a local anesthetic, a neuromuscular blocker, an antimicrobial, an antipsoriatic, a corticosteriod, an anabolic steroid, an erythropoietin, an immunization, an immunoglobulin, an immunosuppressive, a growth hormone, a hormone replacement drug, a radiopharmaceutical; an antidepressant, an antipsychotic, a stimulant, an asthma medication, a beta agonist, an inhaled steroid, an epinephrine or analog.

Also provided is a medical device, comprising at least one isolated mammalian Anti-GD2 antibody of the invention, wherein the device is suitable to contacting or administering the at least one Anti-GD2 antibody by at least one mode selected from parenteral, subcutaneous, intramuscular, intravenous, intrarticular, intrabronchial, intraabdominal, intracapsular, intracartilaginous, intracavitary, intracelial, intracerebellar, intracerebroventricular, intrathecal, intra-Ommaya, intravitreous, intraocular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal.

In a further aspect, the disclosure provides a kit comprising at least one chimeric or humanized Anti-GD2 antibody or fragment of the disclosure in lyophilized form in a first container, and an optional second container comprising sterile water, sterile buffered water, or at least one preservative selected from the group consisting of phenol, m-cresol, p-cresol, o-cresol, chlorocresol, benzyl alcohol, phenylmercuric nitrite, phenoxyethanol, formaldehyde, chlorobutanol, magnesium chloride, alkylparaben, benzalkonium chloride, benzethonium chloride, sodium dehydroacetate and thimerosal, mannitol, sucrose, mannose, other sugars, tween 80, or mixtures thereof in an aqueous diluent. In one aspect, in the kit, the concentration of Anti-GD2 antibody or specified portion or variant in the first container is reconstituted to a concentration of about 0.1 mg/ml to about 500 mg/ml with the contents of the second container. In another aspect, the second container further comprises an isotonicity agent. In another aspect, the second container further comprises a physiologically acceptable buffer. In one aspect, the disclosure provides a method of treating at least one GD2 characterized condition, comprising administering to a patient in need thereof a formulation provided in a kit and reconstituted prior to administration.

Also provided is an article of manufacture for human pharmaceutical or diagnostic use, comprising packaging material and a container comprising a solution or a lyophilized form of at least one isolated chimeric or humanized Anti-GD2 antibody of the present invention. The article of manufacture can optionally comprise having the container as a component of a parenteral, subcutaneous, intramuscular, intravenous, intrarticular, intrabronchial, intraabdominal, intracapsular, intracartilaginous, intracavitary, intracelial, intracerebellar, intracerebroventricular, intrathecal, intra-Ommaya, intravitreous, intraocular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal delivery device or system.

DETAILED DESCRIPTION

In the description that follows, a number of terms used in recombinant DNA and immunology are extensively utilized. In order to provide a clearer and consistent understanding of the specification and claims, including the scope to be given such terms, the following definitions are provided.

The term "antibody" is art-recognized terminology and is intended to include molecules or active fragments of molecules that bind to known antigens. Examples of active fragments of molecules that bind to known antigens include Fab and F(ab')₂ fragments. These active fragments can be derived from an antibody of the present invention by a number of techniques. For example, purified monoclonal antibodies can be cleaved with an enzyme, such as pepsin, and subjected to HPLC gel filtration. The appropriate fraction containing Fab fragments can then be collected and concentrated by membrane filtration and the like. For further description of general techniques for the isolation of active fragments of antibodies, see for example, Khaw, B. A. et al. *J. Nucl. Med.* 23:1011-1019 (1982). The term "antibody" also includes bispecific and chimeric antibodies.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab').sub.2, F(ab).sub.2, Fab', Fab, Fv, sFv and the like. Regardless of structure, an antibody fragment binds with the same antigen that is recognized by the intact antibody. For example, an 3F8 monoclonal antibody fragment binds with an epitope recognized by 3F8. The term "antibody fragment" also includes any synthetic or genetically engineered protein that acts like an antibody by binding to a specific antigen to form a complex. For example, antibody fragments include isolated fragments consisting of the variable regions, such as the "Fv" fragments consisting of the variable regions of the heavy and light chains, recombinant single chain polypeptide molecules in which light and heavy variable regions are connected by a peptide linker ("scFv proteins"), and minimal recognition units consisting of the amino acid residues that mimic the hypervariable region.

The language "monoclonal antibody" is art-recognized terminology. Monoclonal antibodies are monospecific antibodies that are the same because they are made by one type of immune cell that are all clones of a unique parent cell.

A variety of methods exist in the art for the production of monoclonal antibodies. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). Once isolated, the DNA may be placed into expression vectors, which are then transformed into host cells such as NS0 cells, Simian COS cells, Chinese hamster ovary (CHO) cells, yeast cells, algae cells, eggs, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains of a desired species in place of the homologous human sequences (U.S. Pat. No. 4,816,567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The term "epitope" is art-recognized. It is generally understood by those of skill in the art to refer to the region of an antigen or antigens that interacts with an antibody. An epitope of a peptide or protein or sugar antigen can be linear or conformational, or can be formed by contiguous or noncontiguous amino acid and/or sugar sequences of the antigen. The GD2 molecule, like many carbohydrates, contain many epitopes. The epitopes or sugars recognized by the antibodies of the present invention and conservative substitutions of these sugars which are still recognized by the antibody, peptide of chemical mimetics of the GD2 antigen, and antiidiotypic antibodies are an embodiment of the present invention. These sugars, or mimetic peptides/chemicals, or antiidiotypic antibodies, offer a convenient method for eluting GD2 to MoAb or MoAb from GD2 on immunoaffinity columns. Further truncation of these epitopes may be possible.

A naked antibody is generally an entire antibody which is not conjugated to a therapeutic agent. This is so because the Fc portion of the antibody molecule provides effector functions, such as complement fixation and ADCC (antibody-dependent cell cytotoxicity), which set mechanisms into action that may result in cell lysis. Naked antibodies include both polyclonal and monoclonal antibodies, as well as certain recombinant antibodies, such as chimeric, humanized or human antibodies. However, it is possible that the Fc portion is not required for therapeutic function, rather an antibody exerts its therapeutic effect through other mechanisms, such as induction of cell cycle resting and apoptosis. In this case, naked antibodies also include the unconjugated antibody fragments defined above.

A chimeric antibody is a recombinant protein that contains the variable domains including the complementarity-determining regions (CDRs) of an antibody derived from one species, preferably a rodent antibody, while the constant domains of the antibody molecule is derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, is transferred from the heavy and light variable chains of the rodent antibody into human heavy and light variable domains. The constant domain of the antibody molecule is derived from those of a human antibody.

A human antibody is an antibody obtained from transgenic mice that have been "engineered" to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. See for example, McCafferty et al., Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see e.g. Johnson and Chiswell, Current Opinion in Structural Biology 3:5564-571 (1993).

Human antibodies may also be generated by in vitro activated B cells. See U.S. Pat. Nos. 5,567,610 and 5,229,275, which are incorporated in their entirety by reference.

A therapeutic agent is a molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, nucleases, hormones, immunomodulators, chelators, boron compounds, photoactive agents or dyes and radioisotopes.

A diagnostic agent is a molecule or atom which is administered conjugated to an antibody moiety, i.e., antibody or antibody fragment, or subfragment, and is useful in diagnosing or detecting a disease by locating the cells containing the antigen. Useful diagnostic agents include, but are not limited to, radioisotopes, dyes (such as with the biotin-streptavidin complex), contrast agents, fluorescent compounds or molecules and enhancing agents (e.g., paramagnetic ions) for magnetic resonance imaging (MRI). U.S. Pat. No. 6,331,175 describes MRI technique and the preparation of antibodies conjugated to a MRI enhancing agent and is incorporated in its entirety by reference. Preferably, the diagnostic agents are selected from the group consisting of radioisotopes, enhancing agents for use in magnetic resonance imaging, and fluorescent compounds. In order to load an antibody component with radioactive metals or paramagnetic ions, it may be necessary to react it with a reagent having a long tail to which are attached a multiplicity of chelating groups for binding the ions. Such a tail can be a polymer such as a polylysine, polysaccharide, or other derivatized or derivatizable chain having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose. Chelates are coupled to the antibodies using standard chemistries. The chelate is normally linked to the antibody by a group which enables formation of a bond to the molecule with minimal loss of immunoreactivity and minimal aggregation and/or internal cross-linking other, more unusual, methods and reagents for conjugating chelates to antibodies are disclosed in U.S. Pat. No. 4,824,659 to Hawthorne, entitled "Antibody Conjugates," issued Apr. 25, 1989, the disclosure of which is incorporated herein in its entirety by reference. Particularly useful metal-chelate combinations include 2-benzyl-DTPA and its monomethyl and cyclohexyl analogs, used with diagnostic isotopes for radio-imaging. The same chelates, when complexed with non-radioactive metals, such as manganese, iron and gadolinium are useful for MRI, when used along with the antibodies of the invention. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed by the invention.

An immunoconjugate is a conjugate of an antibody component with a therapeutic or diagnostic agent. The diagnostic agent can comprise a radioactive or non-radioactive label, a contrast agent (such as for magnetic resonance imaging, computed tomography or ultrasound), and the radioactive label can be a gamma-, beta-, alpha-, Auger electron-, or positron-emitting isotope.

An immunomodulator is a therapeutic agent as defined in the present invention that when present, typically stimulates immune cells to proliferate or become activated in an immune response cascade, such as macrophages, B-cells, and/or T cells. An example of an immunomodulator as described herein is a cytokine. As the skilled artisan will understand, certain interleukins and interferons are examples of cytokines that stimulate T cell or other immune cell proliferation.

An expression vector is a DNA molecule comprising a gene that is expressed in a host cell. Typically, gene expression is placed under the control of certain regulatory elements, including constitutive or inducible promoters, tissue-specific regulatory elements and enhancers. Such a gene is said to be "operably linked to" the regulatory elements.

A recombinant host may be any prokaryotic or eukaryotic cell that contains either a cloning vector or expression vector. This term also includes those prokaryotic or eukaryotic cells, as well as an transgenic animal, that have been genetically engineered to contain the cloned gene(s) in the chromosome or genome of the host cell or cells of the host cells.

A multispecific antibody is an antibody that can bind simultaneously to at least two targets that are of different structure, e.g., two different antigens, two different epitopes on the same antigen, or a hapten and an antigen or epitope. One specificity would be for, for example, a B-cell, T-cell, myeloid-, plasma-, or mast-cell antigen or epitope. Another specificity could be to a different antigen on the same cell type, such as CD20, CD19, CD21, CD23, CD46, CD80, HLA-DR, CD74, or CD22 on B-cells. Multispecific, multivalent antibodies are constructs that have more than one binding site, and the binding sites are of different specificity. For example, a bispecific diabody, where one binding site reacts with one antigen and the other with another antigen.

A bispecific antibody is an antibody that can bind simultaneously to two targets which are of different structure. Bispecific antibodies (bsAb) and bispecific antibody fragments (bsFab) have at least one arm that specifically binds to, for example, GD2 and at least one other arm that specifically binds to a targetable conjugate that bears a therapeutic or diagnostic agent. A variety of bispecific fusion proteins can be produced using molecular engineering. In one form, the bispecific fusion protein is divalent, consisting of, for example, a scFv with a single binding site for one antigen and a Fab fragment with a single binding site for a second antigen. In another form, the bispecific fusion protein is tetravalent, consisting of, for example, an IgG with two binding sites for one antigen and two identical scFv for a second antigen.

Recent methods for producing bispecific MoAbs include engineered recombinant MoAbs which have additional cysteine residues so that they crosslink more strongly than the more common immunoglobulin isotypes. See, e.g., FitzGerald et al., Protein Eng. 10(10):1221-1225, 1997. Another approach is to engineer recombinant fusion proteins linking two or more different single-chain antibody or antibody fragment segments with the needed dual specificities. See, e.g., Coloma et al., Nature Biotech. 15:159-163, 1997. A variety of bispecific fusion proteins can be produced using molecular engineering.

Bispecific fusion proteins linking two or more different single-chain antibodies or antibody fragments are produced in similar manner. Recombinant methods can be used to produce a variety of fusion proteins. A flexible linker connects the scFv to the constant region of the heavy chain of the 3F8 antibody. Alternatively, the scFv can be connected to the constant region of the light chain of another humanized antibody. Appropriate linker sequences necessary for the in-frame connection of the heavy chain Fd to the scFv are introduced into the $V_L$ and $V_{kappa}$ domains through PCR reactions. The DNA fragment encoding the scFv is then ligated into a staging vector containing a DNA sequence encoding the CH1 domain. The resulting scFv-CH1 construct is excised and ligated into a vector containing a DNA sequence encoding the $V_H$ region of an 3F8 antibody. The resulting vector can be used to transfect an appropriate host cell, such as a mammalian cell for the expression of the bispecific fusion protein.

The 3F8 antibodies and fragments thereof of the present invention can also be used to prepare functional bispecific single-chain antibodies (bscAb), also called diabodies, and can be produced in mammalian cells using recombinant methods. See, e.g., Mack et al., Proc. Natl. Acad. Sci., 92: 7021-7025, 1995, incorporated herein by reference. For example, bscAb are produced by joining two single-chain Fv fragments via a glycine-serine linker using recombinant methods. The V light-chain and V heavy-chain domains of two antibodies of interest are isolated using standard PCR methods known in the art. Bispecific single-chain antibodies and bispecific fusion proteins are included within the scope of the present invention.

The ultimate use of the bispecific diabodies described herein is for pre-targeting GD2 positive cells for subsequent specific delivery of diagnostic/detection or therapeutic agents. These diabodies bind selectively to targeted antigens allowing for increased affinity and a longer residence time at the desired location. Moreover, non-antigen bound diabodies are cleared from the body quickly and exposure of normal tissues is minimized. The diagnostic/detection and therapeutic agents can include isotopes, drugs, toxins, cytokines, hormones, growth factors, conjugates, radionuclides, and metals. For example, gadolinium metal is used for magnetic resonance imaging (MRI). Radionuclides are also available as diagnostic and therapeutic agents, especially those in the energy range of 60 to 4,000 keV.

The targetable construct can be of diverse structure, but is selected not only to avoid eliciting an immune responses, but also for rapid in vivo clearance when used within the bsAb targeting method. Hydrophobic agents are best at eliciting strong immune responses, whereas hydrophilic agents are preferred for rapid in vivo clearance; thus, a balance between hydrophobic and hydrophilic needs to be established. This is accomplished, in part, by relying on the use of hydrophilic chelating agents to offset the inherent hydrophobicity of many organic moieties. Also, subunits of the targetable construct may be chosen which have opposite solution properties, for example, peptides, which contain amino acids, some of which are hydrophobic and some of which are hydrophilic. Aside from peptides, carbohydrates may be used.

Peptides having as few as two amino-acid residues may be used, preferably two to ten residues, if also coupled to other moieties such as chelating agents. The linker should be a low molecular weight conjugate, preferably having a molecular weight of less than 50,000 daltons, and advantageously less than about 20,000 daltons, 10,000 daltons or 5,000 daltons, including the metal ions in the chelates.

The presence of hydrophilic chelate moieties on the linker moieties helps to ensure rapid in vivo clearance. In addition to hydrophilicity, chelators are chosen for their metal-binding properties, and are changed at will since, at least for those linkers whose bsAb epitope is part of the peptide or is a non-chelate chemical hapten, recognition of the metal-chelate complex is no longer an issue.

A chelator such as DTPA, DOTA, TETA, or NOTA or a suitable peptide, to which a detectable label, such as a fluorescent molecule, or cytotoxic agent, such as a heavy metal or radionuclide, can be conjugated. For example, a therapeutically useful immunoconjugate can be obtained by conjugating a photoactive agent or dye to an antibody fusion protein. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy (Jori et al. (eds.), PHOTODYNAMIC THERAPY OF TUMORS AND OTHER DISEASES (Libreria Progetto 1985); van den Bergh, Chem. Britain 22:430 (1986)). Moreover, monoclonal antibodies have been coupled with photoactivated dyes for achieving phototherapy. Mew et al., J. Immunol. 130:1473 (1983); idem., Cancer Res. 45:4380 (1985); Oseroff et al., Proc. Natl. Acad. Sci. USA 83:8744 (1986); idem., Photochem. Photobiol. 46:83 (1987); Hasan et al., Prog. Clin. Biol. Res. 288:471 (1989); Tatsuta et al., Lasers Surg. Med. 9:422 (1989); Pelegrin et al., Cancer 67:2529 (1991). However, these earlier studies did not include use of endoscopic therapy applications, especially with the use of antibody fragments or subfragments. Thus, the present invention contemplates the therapeutic use of immunoconjugates comprising photoactive agents or dyes.

The same chelators, when complexed with non-radioactive metals, such as Mn, Fe and Gd can be used for MRI, when used along with the bsAbs of the invention. Macrocyclic chelators such as NOTA (1,4,7-triaza-cyclononane-N,N',N''-triacetic acid), DOTA, and TETA (p-bromoacetamido-benzyl-tetraethylaminetetraacetic acid) are of use with a variety of metals and radiometals, most particularly with radionuclides of Ga, Y and Cu, respectively.

As used herein, the terms "prevent", "preventing" and "prevention" refer to the prevention of the recurrence or onset of one or more symptoms of a disorder in a subject as result of the administration of a prophylactic or therapeutic agent.

As used herein, the term "in combination" refers to the use of more than one prophylactic and/or therapeutic agents. The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

"Effector function" as used herein is meant a biochemical event that results from the interaction of an antibody Fc region with an Fc receptor or ligand. Effector functions include but are not limited to antibody dependent cell mediated cytotoxicity (ADCC), antibody dependent cell mediated phagocytosis (ADCP), and complement mediated cytotoxicity (CMC). Effector functions include both those that operate after the binding of an antigen and those that operate independent of antigen binding.

"Effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, large granular lymphocytes, Langerhans' cells, natural killer (NK) cells, T-lymphoctes, B-lymphocytes and may be from any organism including but not limited to humans, mice, rats, rabbits, and monkeys.

"Fc ligand" as used herein is meant a molecule, preferably a polypeptide, from any organism that binds to the Fc region of an antibody to form an Fc-ligand complex. Fc ligands include but are not limited to Fc-gamma-RIIA (CD32A), Fc-gamma-RIIB (CD32B), Fc-gamma-RIIIA (CD16A), Fc-gamma-RIIIB (CD16B), Fc-gamma-RI (CD64), Fc-epsilon-RII (CD23), FcRn, C1q, C3, staphylococcal protein A, streptococcal protein G, and viral Fc.gamma.R. Fc ligands may include undiscovered molecules that bind Fc.

In a preferred specific embodiment, the invention encompasses a molecule comprising a variant Fc region, wherein said variant Fc region comprises at least one amino acid modification relative to a wild-type Fc region, such that said molecule has an altered affinity for an FcγR, provided that said variant Fc region does not have a substitution at positions that make a direct contact with FcγR based on crystallographic and structural analysis of Fc-FcγR interactions such as those disclosed by Sondermann et al., 2000 (Nature, 406: 267-273 which is incorporated herein by reference in its entirety). Examples of positions within the Fc region that make a direct contact with FcγR are amino acids 234-239 (hinge region), amino acids 265-269 (B/C loop), amino acids 297-299 (C'/E loop), and amino acids 327-332 (F/G) loop. In some embodiments, the molecules of the invention comprising variant Fc regions comprise modification of at least one residue that makes a direct contact with an FcγR based on structural and crystallographic analysis.

One aspect of the invention includes 3F8 antibody with altered affinities for activating and/or inhibitory receptors, having variant Fc regions with one or more amino acid modifications, wherein said one or more amino acid modification is a substitution at position 239 with aspartic acid, at position 330 with Leucine and at position 332 with glutamic acid (See Example 13).

The invention encompasses molecules comprising a variant Fc region with additions, deletions, and/or substitutions to one or more amino acid in the Fc region of an antibody of the present invention in order to alter effector function, or enhance or diminish affinity of antibody to FcR. These mutations are within the skill of a person in the art. Therefore, the invention encompasses molecules comprising variant Fc regions that binds with a greater affinity to one or more FcγRs. Such molecules preferably mediate effector function more effectively as discussed infra. In other embodiments, the invention encompasses molecules comprising a variant Fc region that bind with a weaker affinity to one or more FcγRs. Reduction or elimination of effector function is desirable in certain cases for example in the case of antibodies whose mechanism of action involves blocking or antagonism but not killing of the cells bearing a target antigen. Reduction or elimination of effector function would be desirable in cases of autoimmune disease where one would block FcγR activating receptors in effector cells (This type of function would be present in the host cells). In general increased effector function would be directed to tumor and foreign cells.

The Fc variants of the present invention may be combined with other Fc modifications, including but not limited to modifications that alter effector function. The invention encompasses combining an Fc variant of the invention with other Fc modifications to provide additive, synergistic, or novel properties in antibodies or Fc fusions. Preferably the Fc variants of the invention enhance the phenotype of the modification with which they are combined. For example, if an Fc variant of the invention is combined with a mutant known to bind FcγRIIIA with a higher affinity than a comparable molecule comprising a wild type Fc region; the combination with a mutant of the invention results in a greater fold enhancement in FcγRIIIA affinity. In some embodiments, the Fc variants of the present invention are incorporated into an antibody or Fc fusion that comprises one or more engineered glycoforms, i.e., a carbohydrate composition that is covalently attached to a molecule comprising an Fc region, wherein said carbohydrate composition differs chemically from that of a parent molecule comprising an Fc region.

The invention encompasses antibodies with modified glycosylation sites, preferably without altering the functionality of the antibody, e.g., binding activity GD2. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. An Fc-glycoform, hu3F8-H1L1-IgG1n that lacked certain oligosaccharides including fucose and terminal N-acetylglucosamine was produced in special CHO cells and exhibited enhanced ADCC effector function.

In some embodiments, the invention encompasses methods of modifying the carbohydrate content of an antibody of the invention by adding or deleting a glycosylation site. Methods for modifying the carbohydrate content of antibodies are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. No. 6,218,149; U.S. Pat. No. 6,472,511; all of which are incorporated herein by reference in their entirety. In other embodiments, the invention encompasses methods of modifying the carbohydrate content of an antibody of the invention by deleting one or more endogenous carbohydrate moieties of the antibody. In a specific embodiment, the invention encompasses deleting the glycosylation site of the Fc region of an antibody, by modifying position 297 from asparagine to alanine.

Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTIll), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et al., 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland); each of which is incorporated herein by reference in its entirety. See, e.g., WO 00061739; EA01229125; US 20030115614; Okazaki et al., 2004, JMB, 336: 1239-49 each of which is incorporated herein by reference in its entirety.

As used herein, the term "derivative" in the context of polypeptides or proteins refers to a polypeptide or protein that comprises an amino acid sequence which has been altered by the introduction of amino acid residue substitutions, deletions or additions. The term "derivative" as used herein also refers to a polypeptide or protein which has been modified, i.e, by the covalent attachment of any type of molecule to the polypeptide or protein. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide or protein may be produced by chemical modifications using techniques known to those of skill in the art, including, but not limited to specific chemical cleavage, acetylation, formylation, metabolic synthesis of tunicamycin, etc. Further, a derivative polypeptide or protein derivative possesses a similar or identical function as the polypeptide or protein from which it was derived.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide.

Effective Amount: As used herein, the term "effective amount" refers to an amount of a given compound, conjugate or composition that is necessary or sufficient to realize a desired biologic effect. An effective amount of a given compound, conjugate or composition in accordance with the methods of the present invention would be the amount that achieves this selected result, and such an amount can be determined as a matter of routine by a person skilled in the art, using assays that are known in the art and/or that are described herein, without the need for undue experimentation. For example, an effective amount for treating or preventing cancer metastasis could be that amount necessary to prevent migration and invasion of a tumor cell across the basement membrane or across an endothelial layer in vivo. The term is also synonymous with "sufficient amount." The effective amount for any particular application can vary depending on such factors as the disease, disorder or condition being treated, the particular composition being administered, the route of administration, the size of the subject, and/or the severity of the disease or condition. One of ordinary skill in the art can determine empirically the effective amount of a particular compound, conjugate or composition of the present invention, in accordance with the guidance provided herein, without necessitating undue experimentation.

As used herein in connection with a measured quantity, the term "about" refers to the normal variation in that measured quantity that would be expected by the skilled artisan making the measurement and exercising a level of care commensurate with the objective of the measurement and the precision of the measuring equipment used. Unless otherwise indicated, "about" refers to a variation of +/−10% of the value provided.

By an "isolated" polypeptide or a fragment, variant, or derivative thereof is intended a polypeptide that is not in its natural milieu. No particular level of purification is required. For example, an isolated polypeptide can be removed from its native or natural environment. Recombinantly produced polypeptides and proteins expressed in host cells are considered isolated for purposed of the invention, as are native or recombinant polypeptides which have been separated, fractionated, or partially or substantially purified by any suitable technique.

Also included as polypeptides of the present invention are fragments, derivatives, analogs, or variants of the foregoing polypeptides, and any combination thereof. The terms "fragment," "variant," "derivative" and "analog" when referring to Anti-GD2 antibodies or antibody polypeptides include any polypeptides which retain at least some of the antigen-binding properties of the corresponding native antibody or polypeptide, i.e., those polypeptides that retain the ability to bind to one or more epitopes on GD2. Fragments of polypeptides of the present invention include proteolytic fragments, as well as deletion fragments, in addition to specific antibody fragments discussed elsewhere herein. Variants of Anti-GD2 antibodies and antibody polypeptides useful in accordance with the present invention include fragments as described above, and also polypeptides with altered amino acid sequences due to amino acid substitutions, deletions, or insertions. Variants may occur naturally or be non-naturally occurring. Non-naturally occurring variants may be produced using art-known mutagenesis techniques or unnatural amino acids. Variant polypeptides may comprise conservative or non-conservative amino acid substitutions, deletions or additions. Derivatives of Anti-GD2 antibodies and antibody polypeptides useful in accordance with the present invention are polypeptides which have been altered so as to exhibit additional features not found on the native polypeptide. Examples include fusion proteins. Variant polypeptides may also be referred to herein as "polypeptide analogs." As used herein a "derivative" of an Anti-GD2 antibody or antibody polypeptide refers to a subject polypeptide having one or more residues chemically derivatized by reaction of a functional side group. Also included as "derivatives" are those peptides which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

Treatment: As used herein, the terms "treatment," "treat," "treated" or "treating" refer to prophylaxis and/or therapy, particularly wherein the object is to prevent or slow down (lessen) an undesired physiological change or disorder, such as the progression of multiple sclerosis. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented. By "subject" or "individual" or "animal" or "patient" or "mammal," is meant any subject, particularly a mammalian subject, for whom diagnosis, prognosis, or therapy is desired. Mammalian subjects include humans and other primates, domestic animals, farm animals, and zoo, sports, or pet animals such as dogs, cats, guinea pigs, rabbits, rats, mice, horses, cattle, cows, and the like.

Humanized Antibodies

In one embodiment, the antibodies provided by the present invention are monoclonal antibodies, which in a preferred embodiment are humanized versions of cognate Anti-GD2 antibodies derived from other species. A humanized antibody is an antibody produced by recombinant DNA technology, in which some or all of the amino acids of a human immunoglobulin light or heavy chain that are not required for antigen binding (e.g., the constant regions and the framework regions of the variable domains) are used to substitute for the corresponding amino acids from the light or heavy chain of the cognate, nonhuman antibody. By way of example, a humanized version of a murine antibody to a given antigen has on both of its heavy and light chains (1) constant regions of a human antibody; (2) framework regions from the variable domains of a human antibody; and (3) CDRs from the murine antibody. When necessary, one or more residues in the human framework regions can be changed to residues at the corresponding positions in the murine antibody so as to preserve the binding affinity of the humanized antibody to the antigen. This change is sometimes called "back mutation." Similarly, forward mutations may be made to revert back to murine sequence for a desired reason, e.g. stability or affinity to antigen. For example, for hu3F8-H1L1-IgG1 backmutations were necessary at 19 positions in the heavy chain sequence and 17 positions in the light chain in order to maintain the in vitro affinity of binding. Humanized antibodies generally are less likely to elicit an immune response in humans as compared to chimeric human antibodies because the former contain considerably fewer non-human components.

Suitable methods for making the humanized antibodies of the present invention are described in, e.g., Winter EP 0 239 400; Jones et al., Nature 321:522-525 (1986); Riechmann et al., Nature 332:323-327 (1988); Verhoeyen et al., Science 239: 1534-1536 (1988); Queen et al., Proc. Nat. Acad. ScL USA 86:10029 (1989); U.S. Pat. No. 6,180,370; and Orlandi et al., Proc. Natl. Acad. Sd. USA 86:3833 (1989); the disclosures of all of which are incorporated by reference herein in their entireties. Generally, the transplantation of murine (or other non-human) CDRs onto a human antibody is achieved as follows. The cDNAs encoding heavy and light chain variable domains are isolated from a hybridoma. The DNA sequences of the variable domains, including the CDRs, are determined by sequencing. The DNAs, encoding the CDRs are inserted into the corresponding regions of a human antibody heavy or light chain variable domain coding sequences, attached to human constant region gene segments of a desired isotype (e.g., γl for CH and K for $C_L$), are gene synthesized. The humanized heavy and light chain genes are co-expressed in mammalian host cells (e.g., CHO or NSO cells) to produce soluble humanized antibody. To facilitate large scale production of antibodies, it is often desirable select for high expressor using a DHFR gene or GS gene in the producer line. These producer cell lines are cultured in bioreactors, or hollow fiber culture system, or WAVE technology, to produce bulk cultures of soluble antibody, or to produce transgenic mammals (e.g., goats, cows, or sheep) that express the antibody in milk (see, e.g., U.S. Pat. No. 5,827,690).

Using the above-described approaches, humanized and chimeric versions of the 3F8 antibody, were generated. The cDNAs encoding the murine 3F8 variable regions of the light and heavy chains were used to construct vectors for expression of murine-human chimeras in which the murine 3F8 variable regions were linked to human IgG1 (for heavy chain) and human kappa (for light chain) constant regions, as described in the Examples herein. In addition, novel forms of hu3F8 with variant glycosylation were created, in order to enhance binding to the Fc receptor and enhance antigen affinity.

In order to produce humanized 3F8 antibodies, the human acceptor framework domains were chosen by homology matching to human germline sequences. Using these chosen human acceptor frameworks, the light and heavy chain variable domains were designed and a number of variants/versions of each were generated and expressed, as described below in Examples.

The nucleotide and amino acid sequence of the heavy and light chain variable regions of the MoAbs of the invention are described in this application. The invention further provides polynucleotides comprising a nucleotide sequence encoding an antibody of the invention and fragments thereof. The invention also encompasses polynucleotides that hybridize under stringent or lower stringency hybridization conditions to polynucleotides that encode an antibody of the present invention.

The polynucleotides may now be obtained by any method known in the art. For example, since the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Since the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, N.Y., which are both incorporated by reference herein in their entireties), to generate antibodies having a different amino acid sequence, for example to create amino acid substitutions, deletions, and/or insertions.

Nucleic acid molecules of the present invention can be in the form of RNA, such as mRNA, hnRNA, tRNA or any other form, or in the form of DNA, including, but not limited to, cDNA and genomic DNA obtained by cloning or produced synthetically, or any combinations thereof. The DNA can be triple-stranded, double-stranded or single-stranded, or any combination thereof. Any portion of at least one strand of the DNA or RNA can be the coding strand, also known as the sense strand, or it can be the non-coding strand, also referred to as the anti-sense strand.

Isolated nucleic acid molecules of the present invention can include nucleic acid molecules comprising an open reading frame (ORF), optionally with one or more introns, e.g., but not limited to, at least one specified portion of at least one CDR, as CDR1, CDR2 and/or CDR3 of at least one heavy chain or light chain; nucleic acid molecules comprising the coding sequence for an Anti-GD2 antibody or variable region; and nucleic acid molecules which comprise a nucleotide sequence substantially different from those described above but which, due to the degeneracy of the genetic code, still encode at least one Anti-GD2 antibody as described herein and/or as known in the art.

The present invention provides isolated nucleic acids that hybridize under selective hybridization conditions to a polynucleotide disclosed herein. Thus, the polynucleotides of this embodiment can be used for isolating, detecting, and/or quantifying nucleic acids comprising such polynucleotides. For example, polynucleotides of the present invention can be used to identify, isolate, or amplify partial or full-length clones in a deposited library. In some embodiments, the polynucleotides are genomic or cDNA sequences isolated, or otherwise complementary to, a cDNA from a human or mammalian nucleic acid library.

The nucleic acids can conveniently comprise sequences in addition to a polynucleotide of the present invention. For example, a multi-cloning site comprising one or more endonuclease restriction sites can be inserted into the nucleic acid to aid in isolation of the polynucleotide. Also, translatable sequences can be inserted to aid in the isolation of the translated polynucleotide of the present invention. For example, a hexa-histidine marker sequence provides a convenient means to purify the proteins of the present invention. The nucleic acid of the present invention—excluding the coding sequence—is optionally a vector, adapter, or linker for cloning and/or expression of a polynucleotide of the present invention.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art. (See, e.g., Ausubel, supra; or Sambrook, supra).

A vector comprising any of the above-described isolated or purified nucleic acid molecules, or fragments thereof, is further provided by the present invention. Any of the above nucleic acid molecules, or fragments thereof, can be cloned into any suitable vector and can be used to transform or transfect any suitable host. The selection of vectors and methods to construct them are commonly known to persons of ordinary skill in the art and are described in general technical references (see, in general, "Recombinant DNA Part D," Methods in Enzymology, Vol. 153, Wu and Grossman, eds., Academic Press (1987)). Desirably, the vector comprises regulatory sequences, such as transcription and translation initiation and termination codons, which are specific to the type of host (e.g., bacterium, fungus, plant or animal) into which the vector is to be introduced, as appropriate and taking into consideration whether the vector is DNA or RNA. Preferably, the vector comprises regulatory sequences that are specific to the genus of the host. Most preferably, the vector comprises regulatory sequences that are specific to the species of the host.

In addition to the replication system and the inserted nucleic acid, the construct can include one or more marker genes, which allow for selection of transformed or transfected hosts. Marker genes include biocide resistance, e.g., resistance to antibiotics, heavy metals, etc., complementation in an auxotrophic host to provide prototrophy, and the like.

Suitable vectors include those designed for propagation and expansion or for expression or both. For example, a cloning vector is selected from the group consisting of the pUC series, the pBluescript series (Stratagene, LaJolla, Calif.), the pET series (Novagen, Madison, Wis.), the pGEX series (Pharmacia Biotech, Uppsala, Sweden), and the pEX series (Clontech, Palo Alto, Calif.). Bacteriophage vectors, such as λGT10, λGT11, λZapII (Stratagene), λEMBL4, and λNM1149, also can be used. Examples of plant expression vectors include pBI110, pBI101.2, pBI101.3, pBI121 and pBIN19 (Clontech). Examples of animal expression vectors include pEUK-C1, pMAM and pMAMneo (Clontech). The TOPO cloning system (Invitrogen, Carlsbad, Calif.) also can be used in accordance with the manufacturer's recommendations.

An expression vector can comprise a native or normative promoter operably linked to an isolated or purified nucleic acid molecule as described above. The selection of promoters, e.g., strong, weak, inducible, tissue-specific and developmental-specific, is within the skill in the art. Similarly, the combining of a nucleic acid molecule, or fragment thereof, as described above with a promoter is also within the skill in the art.

Suitable viral vectors include, for example, retroviral vectors, parvovirus-based vectors, e.g., adeno-associated virus (AAV)-based vectors, AAV-adenoviral chimeric vectors, and adenovirus-based vectors, and lentiviral vectors, such as Herpes simplex (HSV)-based vectors. These viral vectors can be prepared using standard recombinant DNA techniques described in, for example, Sambrook et al., Molecular Cloning, a Laboratory Manual, 2d edition, Cold Spring Harbor Press, Cold Spring Harbor, N.Y. (1989); and Ausubel et al., Current Protocols in Molecular Biology, Greene Publishing Associates and John Wiley & Sons, New York, N.Y. (1994).

A retroviral vector is derived from a retrovirus. Retrovirus is an RNA virus capable of infecting a wide variety of host cells. Upon infection, the retroviral genome integrates into the genome of its host cell and is replicated along with host cell DNA, thereby constantly producing viral RNA and any nucleic acid sequence incorporated into the retroviral genome. As such, long-term expression of a therapeutic factor (s) is achievable when using retrovirus. Retroviruses contemplated for use in gene therapy are relatively non-pathogenic, although pathogenic retroviruses exist. When employing pathogenic retroviruses, e.g., human immunodeficiency virus (HIV) or human T-cell lymphotrophic viruses (HTLV), care must be taken in altering the viral genome to eliminate toxicity to the host. A retroviral vector additionally can be manipulated to render the virus replication-deficient. As such, retroviral vectors are considered particularly useful for stable gene transfer in vivo. Lentiviral vectors, such as HIV-based vectors, are exemplary of retroviral vectors used for gene delivery. Unlike other retroviruses, HIV-based vectors are known to incorporate their passenger genes into non-dividing cells and, therefore, can be of use in treating persistent forms of disease.

Optionally, the isolated or purified nucleic acid molecule, or fragment thereof, upon linkage with another nucleic acid molecule, can encode a fusion protein. The generation of fusion proteins is within the ordinary skill in the art and can involve the use of restriction enzyme or recombinational cloning techniques (see, e.g., Gateway™. (Invitrogen)). See, also, U.S. Pat. No. 5,314,995.

In view of the foregoing, the present invention also provides a composition comprising an above-described isolated or purified nucleic acid molecule, optionally in the form of a vector. The composition can comprise other components as described further herein.

Also in view of the above, the present invention provides a host cell comprising an above-described isolated or purified nucleic acid molecule, optionally in the form of a vector. It is most preferable that the cell of the present invention expresses the vector, such that the oligonucleotide, or fragment thereof, is both transcribed and translated efficiently by the cell. Examples of cells include, but are not limited to, a human cell, a human cell line, E. coli (e.g., E. coli TB-1, TG-2, DH5a, XL-Blue MRF' (Stratagene), SA2821 andY1090), B. subtilis, P. aerugenosa, S. cerevisiae, N. crassa, insect cells (e.g., Sf9, Ea4) and others set forth herein below. The host cell can be present in a host, which can be an animal, such as a mammal, in particular a human.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules represented in SEQ ID NOS: 1, 2, 4, 7, 8, and the light chain immunoglobulin molecules represented in SEQ ID NOS: 2, 5, 6, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

In a specific embodiment, using routine recombinant DNA techniques, one or more of the CDRs identified herein may be inserted within framework regions. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds GD2. One or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/60433, WO 98/24893, WO 98/16664, WO 96/34096, WO 96/33735, and WO 91/10741; each of which is incorporated herein by reference in its entirety. The techniques of Cole et al., and Boerder et al., are also available for the preparation of human monoclonal antibodies (Cole et al., Monoclonal Antibodies and Cancer Therapy, Alan R. Riss, (1985); and Boerner et al., J. Immunol., 147(1):86-95, (1991)).

Human antibodies produced using other techniques but retaining the variable regions of the Anti-GD2 antibody of the present invention are part of this invention. Human antibodies can also be produced using transgenic mice which are incapable of expressing functional endogenous mouse immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,886,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Also human MoAbs could be made by immunizing mice transplanted with human peripheral blood leukocytes, splenocytes or bone marrows (e.g., Trioma techniques of XTL). Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

As used herein, an "Anti-GD2 antibody", "Anti-GD2 antibody portion," or "Anti-GD2 antibody fragment" and/or "Anti-GD2 antibody variant" and the like include any protein or peptide containing molecule that comprises at least a portion of an immunoglobulin molecule, containing at least one complementarity determining region (CDR) of a heavy or light chain or a ligand binding portion thereof derived from a any of the chimeric or humanized monoclonal antibodies described herein, in combination with a heavy chain or light chain variable region, a heavy chain or light chain constant region, a framework region, or any portion thereof, of non-murine origin, preferably of human origin, which can be incorporated into an antibody of the present invention. Alternatively, the term "Anti-GD2 antibody" shall refer collectively or individually to the chimeric antibody ch3F8-IgG1, ch3F8-IgG4, humanized monoclonal antibodies hu3F8-H1L1-IgG1, hu3F8H1L2-IgG1, hu3F8H2L1-IgG1 hu3F8-H2L2-IgG1, hu3F8-H1L1-IgG1n, hu3F8-H1L1-IgG4, hu3F8-H3L3, hu3F8-H1L1S, hu3F8-H3L3S, huH1-1-gamma-1, huH3-1-gamma-1, hu3F8-IgG1-DEL antibodies as well as fragments and regions thereof. Such antibody is capable of modulating, decreasing, antagonizing, mitigating, alleviating, blocking, inhibiting, abrogating and/or interfering with at least one cell function in vitro, in situ and/or in vivo, wherein said cell expresses GD2. As a non-limiting example, a suitable Anti-GD2 antibody, specified portion or variant of the present invention can bind with high affinity to an epitope of human GD2.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof, each containing at least one CDR derived from an Anti-GD2 antibody. Functional fragments include antigen-binding fragments that bind to a mammalian GD2. For example, antibody fragments capable of binding to GD2 or portions thereof, including, but not limited to Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Antibody fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the CH, domain and/or hinge region of the heavy chain. The various portions of antibodies can be joined together chemically by conventional techniques, or can be prepared as a contiguous protein using genetic engineering techniques.

As used herein "chimeric" antibodies or "humanized" antibodies or "CDR-grafted" include any combination of the herein described Anti-GD2 Abs, or any CDR derived therefrom combined with one or more proteins or peptides derived from a non-murine, preferably, human antibody. In accordance with the invention, chimeric or humanized antibodies include those wherein the CDR's are derived from one or more of the Anti-GD2 Abs described herein and at least a portion, or the remainder of the antibody is derived from one or more human antibodies. Thus, the human part of the antibody may include the framework, $C_L$, $C_H$ domains (e.g., $C_{H1}$, $C_{H2}$, $C_{H3}$), hinge, ($V_L$, $V_H$)) regions which are substantially non-immunogenic in humans. The regions of the antibody that are derived from human antibodies need not have 100% identity with human antibodies. In a preferred embodiment, as many of the human amino acid residues as possible are retained in order for the immunogenicity to be negligible, but the human residues may be modified as necessary to support the antigen binding site formed by the CDR's while simultaneously maximizing the humanization of the antibody. Such changes or variations optionally and preferably retain or reduce the immunogenicity in humans or other species relative to non-modified antibodies. It is pointed out that a humanized antibody can be produced by a non-human animal or prokaryotic or eukaryotic cell that is capable of expressing functionally rearranged human immunoglobulin (e.g., heavy chain and/or light chain) genes. Further, when the antibody is a single chain antibody, it can comprise a linker peptide that is not found in native human antibodies. For example, an Fv can comprise a linker peptide, such as two to about twenty glycine or other amino acid residues, preferably 8-15 glycine or other amino acid residues, which connects the variable region of the heavy chain and the variable region of the light chain. Such linker peptides are considered to be of human origin.

Antibody humanization can be performed by, for example, synthesizing a combinatorial library comprising the six CDRs of a non-human target monoclonal antibody fused in frame to a pool of individual human frameworks. A human framework library that contains genes representative of all known heavy and light chain human germline genes can be utilized. The resulting combinatorial libraries can then be screened for binding to antigens of interest. This approach can allow for the selection of the most favorable combinations of fully human frameworks in terms of maintaining the binding activity to the parental antibody. Humanized antibodies can then be further optimized by a variety of techniques.

Antibody Humanization can be used to evolve mouse or other non-human antibodies into "fully human" antibodies. The resulting antibody contains only human sequence and no mouse or non-human antibody sequence, while maintaining similar binding affinity and specificity as the starting antibody.

For full length antibody molecules, the immunoglobulin genes can be obtained from genomic DNA or mRNA of hybridoma cell lines. Antibody heavy and light chains are cloned in a mammalian vector system. Assembly is documented with double strand sequence analysis. The antibody construct can be expressed in other human or mammalian host cell lines. The construct can then be validated by transient transfection assays and Western blot analysis of the expressed antibody of interest. Stable cell lines with the highest productivity can be isolated and screened using rapid assay methods.

At least one Anti-GD2 antibody of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2.sup.nd Edition, Cold Spring Harbor, N.Y. (1989); Harlow and Lane, antibodies, a Laboratory Manual, Cold Spring Harbor, N.Y. (1989). Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference.

In one approach, a hybridoma is produced by fusing a suitable immortal cell line (e.g., a myeloma cell line such as, but not limited to, Sp2/0, Sp2/0-AG14, NSO, NS1, NS2, AE-1, L.5, >243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMAIWA, NEURO 2A), or the like, or heteromylomas, fusion products thereof, or any cell or fusion cell derived therefrom, or any other suitable cell line as known in the art. See, e.g., www.atcc.org, www.lifetech.com., and the like, with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Antibodies of the present invention can also be prepared using at least one Anti-GD2 antibody encoding nucleic acid to provide transgenic animals or mammals, such as goats, cows, horses, sheep, and the like, that produce such antibodies in their milk. Such animals can be provided using known methods. See, e.g., but not limited to, U.S. Pat. Nos. 5,827, 690; 5,849,992; 4,873,316; 5,849,992; 5,994,616, 5,565,362; 5,304,489, and the like, each of which is entirely incorporated herein by reference.

Antibodies of the present invention can additionally be prepared using at least one Anti-GD2 antibody encoding nucleic acid to provide transgenic plants and cultured plant cells (e.g., but not limited to tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem Soc. Trans. 22:940-944 (1994); and references cited therein. Each of the above references is entirely incorporated herein by reference.

An Anti-GD2 antibody can be recovered and purified from recombinant cell cultures by well-known methods including, but not limited to, protein A purification, protein G purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., chapters 1, 4, 6, 8, 9, and 10, each entirely incorporated herein by reference.

Antibodies of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody of the present invention can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Purified antibodies can be characterized by, for example, ELISA, ELISPOT, flow cytometry, immunocytology, Biacore™ analysis, Sapidyne KinExA™ kinetic exclusion assay, SDS-PAGE and Western blot, or by HPLC analysis as well as by a number of other functional assays disclosed herein.

A typical mammalian expression vector contains at least one promoter element, which mediates the initiation of transcription of mRNA, the antibody coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as pIRESlneo, pRetro-Off, pRetro-On, PLXSN, or pLNCX (Clonetech Labs, Palo Alto, Calif.), pcDNA3.1 (+/−), pcDNA/Zeo (+/−) or pcDNA3.1/Hygro (+/−) (Invitrogen), PSVL and PMSG (Pharmacia, Uppsala, Sweden), pRSVcat (ATCC 37152), pSV2dhfr (ATCC 37146) and pBC12MI (ATCC 67109). Mammalian host cells that could be used include human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as DHFR, GPT, neomycin, or hygromycin allows the identification and isolation of the transfected cells.

The transfected gene can also be amplified to express large amounts of the encoded antibody. The DHFR (dihydrofolate reductase) marker is useful to develop cell lines that carry several hundred or even several thousand copies of the gene of interest. Another useful selection marker is the enzyme glutamine synthase (GS) (Murphy, et al., Biochem. J. 227:277-279 (1991); Bebbington, et al., Bio/Technology 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of antibodies.

In accordance with the present invention, the Anti-GD2 antibodies comprise any one of ch3F8-IgG1, ch3F8-IgG4, hu3F8-H1L1-IgG1, hu3F8-H1L2-IgG1, hu3F8-H2L1-IgG1, hu3F8-H2L2-IgG1, hu3F8-H1L1-IgG1n, hu3F8-H1L1-IgG4, hu3F8-H3L3, hu3F8-H1L1S, hu3F8-H3L3S, huH1I-gamma-1, huH3I-gamma-1, hu3F8-IgG1-DEL antibodies or an antibody in which the variable region or CDRs are derived from any one of ch3F8-IgG1, ch3F8-IgG4, hu3F8-H1L1-IgG1, hu3F8-H1L2-IgG1, hu3F8-H2L1-IgG1, hu3F8-H2L2-IgG1, hu3F8-H1L1-IgG1n, hu3F8-H1L1-IgG4, hu3F8-H3L3, hu3F8-H1L1S, hu3F8-H3L3S, huH1I-gamma1, huH3I-gamma1, hu3F8-IgG1-DEL antibody and the framework and constant regions of the antibody are derived from one or more human antibodies. The variable region or CDRs derived from the antibody preferably have from about 90% to about 100% identity with the variable region or CDRs of any one of ch3F8-IgG1, ch3F8-IgG4, hu3F8-H1L1-IgG1, hu3F8-H1L2-IgG1, hu3F8-H2L1-IgG1, hu3F8-H2L2-IgG1, hu3F8-H1L1-IgG1n, hu3F8-H1L1-IgG4, hu3F8-H3L3, hu3F8-H1L1S, hu3F8-H3L3S, huH1I-gamma1, huH3I-gamma1, hu3F8-IgG1-DEL although any and all modifications, including substitutions, insertions and deletions, either from natural mutation or from human manipulation are contemplated so long as the antibody maintains the ability to bind to GD2. The regions of the chimeric, humanized or CDR-grafted antibodies that are derived from human antibodies need not have 100% identity with the human antibodies. In a preferred embodiment, as many of the human amino acid residues as possible are retained in order that immunogenicity is negligible, but the human residues, in particular residues of the framework region, are substituted as required and as taught herein below in accordance with the present invention. Such modifications as disclosed herein are necessary to support the antigen binding site formed by the CDRs while simultaneously maximizing the humanization of the antibody.

Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Of course, the number of amino acid substitutions a skilled artisan would make depends on many factors, including those described above. Generally speaking, the number of amino acid substitutions, insertions or deletions for any given Anti-GD2 antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an Anti-GD2 antibody of the present invention that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to at least binding to GD2. Sites that are critical for antibody binding can also be identified by structural analysis such as crystallization, nuclear magnetic resonance or photoaffinity labeling (Smith, et al., J. Mol. Biol. 224:899-904 (1992) and de Vos, et al., Science 255:306-312 (1992)).

An Anti-GD2 antibody can further optionally comprise a polypeptide of at least one of 70-100% of the contiguous amino acids of the CDRs derived from at least one of sequence described herein.

In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of at least one sequence in Tables 1-4.

Exemplary heavy chain and light chain variable regions sequences are provided herein. The antibodies of the present invention, or specified variants thereof, can comprise any number of contiguous amino acid residues from an antibody of the present invention, wherein that number is selected from the group of integers consisting of from 10-100% of the number of contiguous residues in an Anti-GD2 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

In accordance with the present invention, the nucleic acid sequences set forth in SEQ ID NOs: 11-22 and the deduced amino acid sequences of the variable regions (light and heavy chain) of the Anti-GD2 antibodies are set forth in SEQ ID NOs:1-10. Each of the heavy and light chain variable regions contain three CDRs that combine to form the antigen binding site. The three CDRs are surrounded by four framework regions that primarily function to support the CDRs. The sequences of the CDRs within the sequences of the variable regions of the heavy and light chains can be identified by computer-assisted alignment according to Kabat et al. (1987) in Sequences of Proteins of Immunological Interest, 4th ed., United States Department of Health and Human Services, U.S. Government Printing Office, Washington, D.C., or by molecular modeling of the variable regions, for example utilizing the ENCAD program as described by Levitt (1983) J. Mol. Biol. 168:595.

Human genes which encode the constant (C) regions of the humanized antibodies, fragments and regions of the present invention can be derived from a human fetal liver library, by known methods. Human C region genes can be derived from any human cell including those which express and produce human immunoglobulins. The human $C_H$ region can be derived from any of the known classes or isotypes of human H chains, including gamma, mu, alpha, delta, epsilon, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1) or gamma 4 (IgG4).

The human $C_L$ region can be derived from either human L chain isotype, kappa or lambda, preferably kappa.

Genes encoding human immunoglobulin C regions are obtained from human cells by standard cloning techniques (Sambrook, et al. (Molecular Cloning: A Laboratory Manual, 2.sup.nd Edition, Cold Spring Harbor Press, Cold Spring Harbor, N.Y. (1989) and Ausubel et al., eds. Current Protocols in Molecular Biology (1987-1993)). Human C region genes are readily available from known clones containing genes representing the two classes of L chains, the five classes of H chains and subclasses thereof.

The sequences of the variable regions of the antibody may be modified by insertions, substitutions and deletions to the extent that the chimeric antibody maintains the ability to bind to human GD2. The ordinarily skilled artisan can ascertain the maintenance of this activity by performing the functional assays described hereinbelow. The variable regions can have, for example, from about 50% to about 100% homology to the variable regions identified below. In a preferred embodiment, the variable regions of the antibody have from about 80% to about 100% homology to the variable regions identified below. In a more preferred embodiment the variable regions have from about 90% to about 100% homology to the variable regions identified below.

In one specific aspect, preferred Anti-GD2 Mabs of the disclosure comprise variable light chain regions having 95%, 96%, 97%, 98% or 99% amino acid sequence homology to sequences identified herein and further comprise variable heavy chain regions having 95%, 96%, 97%, 98% or 99% amino acid sequence homology to sequences in identified herein.

Preferably, the antibody or antigen-binding fragment of an antibody or specified portion or variant thereof of the present invention binds human GD2 and, thereby partially or substantially neutralizes one GD2 protein or fragment and thereby inhibit activities mediated through GD2. As used herein, the term "neutralizing antibody" refers to an antibody that can inhibit GD2 dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an Anti-GD2 antibody to inhibit a GD2-dependent activity is preferably assessed by at least one suitable assay, as described herein and/or as known in the art.

As stated, the invention also relates to antibodies, antigen-binding fragments, immunoglobulin chains and CDRs comprising amino acids in a sequence that is substantially the same as an amino acid sequence described herein. Such Anti-GD2 antibodies can include one or more amino acid substitutions, deletions or additions, either from natural mutations or human manipulation, as specified herein. Preferably, such antibodies or antigen-binding fragments and antibodies comprising such chains or CDRs can bind human GD2 with high affinity. [0120] As those of skill in the art will appreciate, the present invention includes at least one biologically active antibody of the present invention. Biologically active antibodies have a specific activity at least 20%, 30%, or 40%, and preferably at least 50%, 60%, or 70%, and most preferably at least 80%, 90%, or 95%-100% of that of the native (non-synthetic), endogenous or related and known antibody. Methods of assaying and quantifying measures of enzymatic activity and substrate specificity, are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments of the invention can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane, e.g. polylysine. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example $PEG_{5000}$ and $PEG_{20,000}$, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N,N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate, n-tetradecanoate, n-octadecanoate, n-eicosanoate, n-docosanoate, n-triacontanoate, n-tetracontanoate, cis-.delta.9-octadecanoate, all cis-.delta.5,8,11,14-eicosatetraenoate, octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hernanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example a divalent $C_1$-$C_{12}$ group wherein one or more carbon atoms can be replaced by a heteroatom such as oxygen, nitrogen or sulfur. Suitable linker moieties include, for example, tetraethylene glycol, —$(CH_2)_3$—, —NH—, to name a few. Modifying agents that comprise a linker moiety can be produced, for example, by reacting a mono-Boc-alkyldiamine (e.g., mono-Boc-ethylenediamine, mono-Boc-diaminohexane) with a fatty acid in the presence of 1-ethyl-3-(3-dimethylaminopropyl)carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate as described, or can be reacted with maleic anhydride and the resulting product cyclized to produce an activated maleimido derivative of the fatty acid. (See, for example, Thompson, et al., WO 92/16221 the entire teachings of which are incorporated herein by reference.)

The modified antibodies of the invention can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

The antibodies of the invention can bind human GD2 with a wide range of affinities ($K_D$) as shown below.

The affinity or avidity of an antibody for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W.H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters are preferably made with standardized solutions of antibody and antigen, and a standardized buffer, such as the buffer described herein.

Anti-GD2 antibodies useful in the methods and compositions of the present invention are characterized by binding to GD2 and preferably having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat patients for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the patients treated and/or raising low titres in the patient treated (Elliott et al., Lancet 344:1125-1127 (1994), entirely incorporated herein by reference).

Bispecific, heterospecific, heteroconjugate or similar antibodies can also be used that are monoclonal, humanized, antibodies that have binding specificities for at least two different antigens. In the present case, one of the binding specificities is for at least one GD2 protein, the other one is for any other antigen. Methods for making bispecific antibodies are known in the art. Traditionally, the recombinant production of bispecific antibodies is based on the co-expression of two immunoglobulin heavy chain-light chain pairs, where the two heavy chains have different specificities (Milstein and Cuello, Nature 305:537 (1983)). Because of the random assortment of immunoglobulin heavy and light chains, these hybridomas (quadromas) produce a potential mixture of 10 different antibody molecules, of which only one has the correct bispecific structure. The purification of the correct molecule, which is usually done by affinity chromatography steps, is rather cumbersome, and the product yields are low. Similar procedures are disclosed, e.g., in WO 93/08829, U.S. Pat. Nos. 6,210,668, 6,193,967, 6,132,992, 6,106,833, 6,060,285, 6,037,453, 6,010,902, 5,989,530, 5,959,084, 5,959,083, 5,932,448, 5,833,985, 5,821,333, 5,807,706, 5,643,759, 5,601,819, 5,582,996, 5,496,549, 4,676,980, WO 91/00360, WO 92/00373, EP 03089, Traunecker et al., EMBO J. 10:3655 (1991), Suresh et al., Methods in Enzymology 121: 210 (1986); Chan and Carter, 2010, Nature Rev. 10, 301-316; Weiner et al., 2010, Nature Rev. 10, 317-327; each entirely incorporated herein by reference.

In certain embodiments, the antibodies, that bind to GD2 can be used in unconjugated form. In other embodiments, the antibodies that bind to GD2 can be conjugated, e.g., to a detectable label, a drug, a prodrug or an isotope.

In certain methods of the invention described in more detail below, such as methods of detecting GD2 expression in cells or tissues as a measure of the metastatic potential of tumor cells, or as a way of identifying in situ carcinomas (e.g., DCIS or LCIS) in tissues, the Anti-GD2 antibodies are conjugated to one or more detectable labels. For such uses, antibodies may be detectably labeled by covalent or non-covalent attachment of a chromogenic, enzymatic, radioisotopic, isotopic, fluorescent, toxic, chemiluminescent, nuclear magnetic resonance contrast agent or other label.

Examples of suitable chromogenic labels include diaminobenzidine and 4-hydroxyazo-benzene-2-carboxylic acid.

Examples of suitable enzyme labels include malate dehydrogenase, staphylococcal nuclease, $\Delta$-5-steroid isomerase, yeast-alcohol dehydrogenase, $\alpha$-glycerol phosphate dehydrogenase, triose phosphate isomerase, peroxidase, alkaline phosphatase, asparaginase, glucose oxidase, $\beta$-galactosidase, ribonuclease, urease, catalase, glucose-6-phosphate dehydrogenase, glucoamylase, and acetylcholine esterase.

Examples of suitable radioisotopic labels include $^3$H, $^{111}$In, $^{125}$I, $^{131}$I, $^{32}$P, $^{35}$S, $^{14}$C, $^{51}$Cr, $^{57}$To, $^{58}$Co, $^{59}$Fe, $^{75}$Se, $^{152}$Eu, $^{90}$Y, $^{67}$Cu, $^{217}$Ci, $^{211}$At, $^{212}$Pb, $^{47}$Sc, $^{109}$Pd, etc. $^{111}$In is a preferred isotope where in vivo imaging is used since its avoids the problem of dehalogenation of the $^{125}$I or $^{131}$I-labeled GD2-binding antibodies by the liver. In addition, this radionucleotide has a more favorable gamma emission energy for imaging (Perkins et al, Eur. J. Nucl. Med. 70:296-301 (1985); Carasquillo et ah, J. Nucl. Med. 25:281-287 (1987)). For example, $^{111}$In coupled to monoclonal antibodies with 1-(P-isothiocyanatobenzyl)-DPTA has shown little uptake in non-tumorous tissues, particularly the liver, and therefore enhances specificity of tumor localization (Esteban et al., J. Nucl. Med. 28:861-870 (1987)).

Examples of suitable non-radioactive isotopic labels include $^{157}$Gd, $^{55}$Mn, $^{162}$Dy, $^{52}$Tr, and $^{56}$Fe.

Examples of suitable fluorescent labels include an $^{152}$Eu label, a fluorescein label, an isothiocyanate label, a rhodamine label, a phycoerythrin label, a phycocyanin label, an allophycocyanin label, a Green Fluorescent Protein (GFP) label, an o-phthaldehyde label, and a fluorescamine label.

Examples of suitable toxin labels include diphtheria toxin, ricin, and cholera toxin.

Examples of chemiluminescent labels include a luminol label, an isoluminol label, an aromatic acridinium ester label, an imidazole label, an acridinium salt label, an oxalate ester label, a luciferin label, a luciferase label, and an aequorin label.

Examples of nuclear magnetic resonance contrasting agents include heavy metal nuclei such as Gd, Mn, and iron.

Typical techniques for binding the above-described labels to Anti-GD2 antibodies, are provided by Kennedy et at., Clin. CMm. Acta 70:1-31 (1976), and Schurs et al, Clin. CMm. Acta 81:1-40 (1977). Coupling techniques mentioned in the latter are the glutaraldehyde method, the periodate method, the dimaleimide method, the m-maleimidobenzyl-N-hydroxy-succinimide ester method, all of which methods are incorporated by reference herein.

For use in certain therapeutic approaches of the invention such as ablation of residual tumor cells following surgery, or prevention of metastasis, the Anti-GD2 antibodies can be conjugated to one or more drugs, prodrugs or isotopes. Preferred such conjugates comprise one or more ligands, e.g., one or more antibodies or fragments, derivatives or variants thereof, that bind to GD2, conjugated to one or more cytotoxic agents; such conjugates are useful in the methods of treatment and prevention of tumor metastasis provided by the invention. According to certain such embodiments of the invention, the Anti-GD2 antibody, is conjugated to a cytotoxic agent. Cytotoxic, e.g., chemotherapeutic, agents useful in the generation of Anti-GD2 antibody-cytotoxic agent conjugates are well known in the art, and include but are not limited to cisplatin, carboplatin, oxaliplatin, paclitaxel, melphalan, doxorubicin, methotrexate, 5-fluorouracil, etoposide, mechlorethamine, cyclophosphamide, bleomycin, microtubule poisons, and annonaceous acetogenins. Other chemotherapeutic agents suitable' for use in accordance with this aspect of the invention are well-known and will be familiar to the ordinarily skilled artisan.

The use of conjugates of one or more Anti-GD2 antibody, and one or more small molecule toxins, such as a calicheamicin, a maytansine (U.S. Pat. No. 5,208,020), a trichothene, and CC1065, are also contemplated herein. In one embodiment of the invention, the Anti-GD2 antibody is conjugated to one or more maytansine molecules (e.g. about 1 to about 10 maytansine molecules per Anti-GD2 antibody). Maytansine may, for example, be converted to May-SS-Me which may be reduced to May-SH3 and reacted with modified Anti-GD2 antibody (Chari et al. Cancer Research 52: 127-131 (1992)) to generate a maytansinoid-Anti-GD2 antibody conjugate.

Alternatively, the Anti-GD2 antibody can be conjugated to one or more calicheamicin molecules. The calicheamicin family of antibiotics are capable of producing double-stranded DNA breaks at sub-picomolar concentrations. Structural analogues of calicheamicin which may be used (Hinman et al. Cancer Research 53: 3336-3342 (1993) and Lode et al. Cancer Research 58: 2925-2928 (1998)).

Enzymatically active toxins and fragments thereof which can be used to produce conjugates with one or more Anti-GD2 antibody, include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleuritesfordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published in the English language on Oct. 28, 1993, the disclosure of which is incorporated herein by reference in its entirety. Mytansinoids may also be conjugated to one or more Anti-GD2 antibody.

The present invention further contemplates Anti-GD2 antibody conjugated with a compound with nucleolytic activity {e.g., a ribonuclease or a DNA endonuclease such as a deoxyribonuclease; DNase).

A variety of radioactive isotopes are also available for the production of radioconjugated Anti-GD2 antibody for use in therapeutic methods of the invention. Examples include $^{211}$At, $^{131}$I, $^{125}$I, $^{90}$Y, $^{186}$Re, $^{188}$Re, $^{153}$Sm, $^{212}$Bi, $^{32}$P and radioactive isotopes of Lu.

Conjugates of the Anti-GD2 antibody and cytotoxic agents may be made using a variety of bifunctional protein coupling agents such as N-succinimidyl-3-(2-pyridyldithiol) propionate (SPDP), succinimidyl-4-(N-maleimidomethyl)cyclohexane-I-carboxylate, iminothiolane (IT), bifunctional derivatives of imidoesters (such as dimethyl adipimidate HCl), active esters (such as disuccinimidyl suberate), aldehydes (such as glutaraldehyde), his-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). $^{14}$Carbon-labeled 1-isothiocyanatobenzyl-3-methyldiethylene triaminepentaacetic acid (MX-DTPA) is an exemplary chelating agent for conjugation of radionucleotide to the Anti-GD2 antibody. See WO 94/11026. The linker may be a "cleavable linker" facilitating release of the cytotoxic drug in the cell. For example, an acid-labile linker, peptidase-sensitive linker, dimethyl linker or disulfide-containing linker (Chari et al. Cancer Research 52:127-131 (1992)) may be used.

Alternatively, a fusion protein comprising the Anti-GD2 antibody ligand and cytotoxic agent may be made, e.g. by recombinant techniques or peptide synthesis.

The present invention also provides at least one Anti-GD2 antibody composition comprising at least one, at least two, at least three, at least four, at least five, at least six or more Anti-GD2 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the Anti-GD2 antibody amino acid sequence selected from the group consisting of 70-100% of the contiguous amino acids of the CDR regions of the antibodies described herein, or specified fragments, domains or variants thereof. Preferred Anti-GD2 antibody compositions include at least one or two full length, fragments, domains or variants as at least one CDR or LBR containing portions of the Anti-GD2 antibody sequences described herein. Further preferred compositions comprise 40-99% of at least one of 70-100% of a CDR region of an Anti-GD2 Ab described herein. Such composition percentages are by weight, volume, concentration, molarity, or molality as liquid or dry solutions, mixtures, suspension, emulsions or colloids, as known in the art or as described herein.

Anti-GD2 antibody compositions of the present invention can further comprise at least one of any suitable and effective amount of a composition or pharmaceutical composition comprising at least one Anti-GD2 antibody to a cell, tissue, organ, animal or patient in need of such modulation, treatment or therapy, optionally further comprising at least one selected from at least one TNF antagonist (e.g., but not limited to a TNF antibody or fragment a soluble TNF receptor or fragment, fusion proteins thereof, or a small molecule TNF antagonist), an antirheumatic (e.g., methotrexate, auranofin, aurothioglucose, azathioprine, etanercept, gold sodium thiomalate, hydroxychloroquine sulfate, leflunomide, sulfasalzine), a muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist, and cell therapies. Non-limiting examples of such cytokines include, but are not limited to, any of IL-1 to IL-34. Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Such anti-cancer or anti-infectives can also include toxin molecules that are associated, bound, co-formulated or co-administered with at least one antibody of the present invention. The toxin can optionally act to selectively kill the pathologic cell or tissue. The pathologic cell can be a cancer or other cell. Such toxins can be, but are not limited to, purified or recombinant toxin or toxin fragment comprising at least one functional cytotoxic domain of toxin, e.g., selected from at least one of ricin, diphtheria toxin, a venom toxin, or a bacterial toxin. The term toxin also includes both endotoxins and exotoxins produced by any naturally occurring, mutant or recombinant bacteria or viruses which may cause any pathological condition in humans and other mammals, including toxin shock, which can result in death. Such toxins may include, but are not limited to, enterotoxigenic *E. coli* heat-labile enterotoxin (LT), heat-stable enterotoxin (ST), *Shigella* cytotoxin, *Aeromonas* enterotoxins, toxic shock syndrome toxin-1 (TSST-1), Staphylococcal enterotoxin A (SEA), B (SEB), or C (SEC), Streptococcal enterotoxins and the like. Such bacteria include, but are not limited to, strains of a species of enterotoxigenic *E. coli* (ETEC), enterohemorrhagic *E. coli* (e.g., strains of serotype 0157:H7), *Staphylococcus* species (e.g., *Staphylococcus aureus, Staphylococcus pyogenes*), *Shigella* species (e.g., *Shigella dysenteriae, Shigella flexneri, Shigella boydii,* and *Shigella sonnei*), *Salmonella* species (e.g., *Salmonella typhi, Salmonella cholerasuis, Salmonella enteritidis*), *Clostridium* species (e.g., *Clostridium perfringens, Clostridium dificile, Clostridium botulinum*), *Camphlobacter* species (e.g., *Camphlobacter jejuni, Camphlobacter fetus*), *Heliobacter* species, (e.g., *Heliobacter pylori*), *Aeromonas* species (e.g., *Aeromonas sobria, Aeromonas hydrophila, Aeromonas caviae*), *Pleisomonas shigelloides, Yersina enterocolitica, Vibrios* species (e.g., *Vibrios cholerae, Vibrios parahemolyticus*), *Klebsiella* species, *Pseudomonas aeruginosa,* and *Streptococci.* See, e.g., Stein, ed., INTERNAL MEDICINE, 3rd ed., pp 1-13, Little, Brown and Co., Boston, (1990); Evans et al., eds., Bacterial Infections of Humans: Epidemiology and Control, 2d. Ed., pp 239-254, Plenum Medical Book Co., New York (1991); Mandell et al, Principles and Practice of Infectious Diseases, 3d. Ed., Churchill Livingstone, N.Y. (1990); Berkow et al, eds., The Merck Manual, 16th edition, Merck and Co., Rahway, N.J., 1992; Wood et al, FEMS Microbiology Immunology, 76:121-134 (1991); Marrack et al, Science, 248:705-711 (1990), the contents of which references are incorporated entirely herein by reference.

Anti-GD2 antibody compounds, compositions or combinations of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18.sup.th Edition, Mack Publishing Co. (Easton, Pa.) 1990. Pharmaceutically acceptable carriers can be routinely selected that are suitable for the mode of administration, solubility and/or stability of the Anti-GD2 antibody, fragment or variant composition as well known in the art or as described herein.

Pharmaceutical excipients and additives useful in the present composition include but are not limited to proteins, peptides, amino acids, lipids, and carbohydrates (e.g., sugars, including monosaccharides, di-, tri-, tetra-, and oligosaccharides; derivatized sugars such as alditols, aldonic acids, esterified sugars and the like; and polysaccharides or sugar polymers), which can be present singly or in combination, comprising alone or in combination 1-99.99% by weight or volume. Exemplary protein excipients include serum albumin such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-GD2 antibody compositions can also include a buffer or a pH adjusting agent; typically, the buffer is a salt prepared from an organic acid or base. Representative buffers include organic acid salts such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts such as citrate.

Additionally, Anti-GD2 antibody compositions of the invention can include polymeric excipients/additives such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the Anti-GD2 antibody, portion or variant compositions according to the invention are known in the art, e.g., as listed in "Remington: The Science & Practice of Pharmacy", 19.sup.th ed., Williams & Williams, (1995), and in the "Physician's Desk Reference", 52.sup.nd ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents.

As noted above, the invention provides for stable formulations, which is preferably a phosphate buffer with saline or a chosen salt, as well as preserved solutions and formulations containing a preservative as well as multi-use preserved formulations suitable for pharmaceutical or veterinary use, comprising at least one Anti-GD2 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the invention provides an article of manufacture, comprising packaging material and at least one vial comprising a solution of at least one Anti-GD2 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further comprises an article of manufacture, comprising packaging material, a first vial comprising lyophilized at least one Anti-GD2 antibody, and a second vial comprising an aqueous diluent of prescribed buffer or preservative, wherein said packaging material comprises a label that instructs a patient to reconstitute the at least one Anti-GD2 antibody in the aqueous diluent to form a solution that can be held over a period of twenty-four hours or greater.

The at least one Anti-GD2 antibody used in accordance with the present invention can be produced by recombinant means, including from mammalian cell or transgenic preparations, or can be purified from other biological sources, as described herein or as known in the art.

The range of at least one Anti-GD2 antibody in the product of the present invention includes amounts yielding upon reconstitution, if in a wet/dry system, concentrations from about 1.0 microgram/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an anti-microbial effect. Such concentrations are dependent on the preservative selected and are readily determined by the skilled artisan.

Other excipients, e.g. isotonicity agents, buffers, antioxidants, preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably the formulations of the present invention have pH between about 6.8 and about 7.8. Preferred buffers include phosphate buffers, most preferably sodium phosphate, particularly phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants such as polysorbate 20 or 80 or poloxamer 184 or 188, Pluronic® polyls, other block co-polymers, and chelators such as EDTA and EGTA can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations of the present invention can be prepared by a process which comprises mixing at least one Anti-GD2 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one Anti-GD2 antibody and preservative in an aqueous diluent is carried out using conventional dissolution and mixing procedures. To prepare a suitable formulation, for example, a measured amount of at least one Anti-GD2 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed formulations can be provided to patients as clear solutions or as dual vials comprising a vial of lyophilized at least one Anti-GD2 antibody that is reconstituted with a second vial containing water, a preservative and/or excipients, preferably a phosphate buffer and/or saline and a chosen salt, in an aqueous diluent. Either a single solution vial or dual vial requiring reconstitution can be reused multiple times and can suffice for a single or multiple cycles of patient treatment and thus can provide a more convenient treatment regimen than currently available.

The present claimed articles of manufacture are useful for administration over a period of immediately to twenty-four hours or greater. Accordingly, the presently claimed articles of manufacture offer significant advantages to the patient. Formulations of the invention can optionally be safely stored at temperatures of from about 2° C. to about 40° C. and retain the biologically activity of the protein for extended periods of time, thus, allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of at least one Anti-GD2 antibody in the invention can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and optionally a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to patients as clear solutions or as dual vials comprising a vial of lyophilized at least one Anti-GD2 antibody that is reconstituted with a second vial containing the aqueous diluent. Either a single solution vial or dual vial requiring reconstitution can be reused multiple times and can suffice for a single or multiple cycles of patient treatment and thus provides a more convenient treatment regimen than currently available.

The claimed products can be provided indirectly to patients by providing to pharmacies, clinics, or other such institutions and facilities, clear solutions or dual vials comprising a vial of lyophilized at least one Anti-GD2 antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or patients.

Recognized devices comprising these single vial systems include those pen-injector devices for delivery of a solution such as BD Pens, BD Autojector®, Humaject®, e.g., as made or developed by Becton Dickensen (Franklin Lakes, N.J.,), Disetronic (Burgdorf, Switzerland; Bioject, Portland, Oreg.; National Medical Products, Weston Medical (Peterborough, UK), Medi-Ject Corp (Minneapolis, Minn.). Recognized devices comprising a dual vial system include those pen-injector systems for reconstituting a lyophilized drug in a cartridge for delivery of the reconstituted solution such as the HumatroPen®.

The products presently claimed include packaging material. The packaging material provides, in addition to the information required by the regulatory agencies, the conditions under which the product can be used. The packaging material of the present invention provides instructions to the patient to reconstitute the at least one Anti-GD2 antibody in the aqueous diluent to form a solution and to use the solution over a period of 2-24 hours or greater for the two vial, wet/dry, product. For the single vial, solution product, the label indicates that such solution can be used over a period of 2-24 hours or greater. The presently claimed products are useful for human pharmaceutical product use.

The formulations of the present invention can be prepared by a process that comprises mixing at least one Anti-GD2 antibody and a selected buffer, preferably a phosphate buffer containing saline or a chosen salt. Mixing the at least one antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed stable or preserved formulations can be provided to patients as clear solutions or as dual vials comprising a vial of lyophilized at least one Anti-GD2 antibody that is reconstituted with a second vial containing a preservative or buffer and excipients in an aqueous diluent. Either a single solution vial or dual vial requiring reconstitution can be reused multiple times and can suffice for a single or multiple cycles of patient treatment and thus provides a more convenient treatment regimen than currently available.

At least one Anti-GD2 antibody in either the stable or presented formulations or solutions described herein, can be administered to a patient in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

In one embodiment of the present invention, the pharmaceutical compositions comprising an Anti-GD2 antibody of the disclosure facilitate administration of humanized antibodies to an organism, preferably an animal, preferably a mammal. Particular mammals include bovine, canine, equine, feline, ovine, and porcine animals, non-human primates, and humans. Humans are particularly preferred.

A high affinity, neutralizing chimeric or human antibody to GD2 would be desirable to be used in diseases where GD2 is expressed, for example, GD2 is expressed in >50% of melanoma (Zhang et al., 1997, Int. J. Cancer. 73, 42-49), 88% of osteosarcoma (Heiner et al., 1987, Cancer Res. 47, 5377-5388), and 93% of soft tissue sarcomas including liposarcoma, fibrosarcoma, malignant fibrous histiocytoma, leiomyosarcoma, and spindle cell sarcoma (Chang et al., 1992, Cancer 70, 633-638), as well as brain tumors (Longee et al., 1991, Acta Neuropathol. 82, 45-54). Anti-GD2 antibodies have been tested in patients with melanoma (Saleh et al, 1992, Hum. Antibodies Hybridomas 3, 19-24; Cheung et al., 1987, J. Clin. Oncol. 5, 1430-1440; Choi et al., 2006, Cancer Immunol. Immunother. 55, 761-774), sarcomas (Choi et al., 2006, supra; Yeh et al., 1992, The fifth Asia and Oceania Congress of Nuclear Medicine and Biology Proceedings, p. 104), small cell lung cancer (Grant et al., 1996, Eur. J. Nucl. Med. 23, 145-149), brain tumors (Arbit et al., 1995, Eur. J. Nucl. Med. 22, 419-426), by iv injection as well as by compartmental therapy using Ommaya reservoirs (Kramer et al., 2007, J. Clin. Oncol. 25, 5465-5470). GD2 is also a tumor target for retinoblastoma (Chantada et al., 2006, J. Pediatr. Hematol. Oncol. 28, 369-373) and HTLV-1 infected T cells leukemia cells (Furukawa et al., 1993, PNAS USA 90, 1972-1976). In one preferred aspect, an Anti-GD2 antibody of the disclosure can be used to treat neuroblastoma. Anti-GD2 antibodies or derivatives thereof can be used either as a single agent or in combination with other therapeutic agents. In addition, these Mabs can be used as a chemosensitizer whereby their use can increase therapeutic efficacy of cytotoxic agents. These antibodies can be used as a radiosensitizer whereby their use can improve efficacy of radiation. They can also be used in combination with other tumor-immunomodulating agents such as IL-2, IL-12 and/or IFNalpha. Additionally, the Anti-GD2 antibodies can be used in combination with other monoclonal antibodies such as anti-TNF-alpha, IL-12/IL-23, IL-2, GpIIb/IIIa receptor, CD52, CD20, RSV proteins, HER2/neu receptor, and the like; as well as with commercially approved antibodies including Rituxan, Herceptin, Mylotarg, Campath, Zevalin, Bexxar, Erbitux, Avastin and Vectibix.

Thus, the present invention also provides a method for modulating or treating at least one GD2 related disease, in a cell, tissue, organ, animal, or patient, as known in the art or as described herein, using at least one Anti-GD2 antibody of the present invention.

The present invention includes a method for modulating or treating at least one malignant disease in a cell, tissue, organ, animal or patient, including, but not limited to, at least one of: multiple myeloma, leukemia, acute leukemia, acute lymphoblastic leukemia (ALL), B-cell, T-cell or FAB ALL, acute myeloid leukemia (AML), chromic myelocytic leukemia (CML), chronic lymphocytic leukemia (CLL), hairy cell leukemia, myelodysplastic syndrome (MDS), a lymphoma, Hodgkin's disease, a malignant lymphoma, non-hodgkin's lymphoma, Burkitt's lymphoma, multiple myeloma, Kaposi's sarcoma, colorectal carcinoma, renal cell carcinoma, pancreatic carcinoma, prostatic carcinoma, nasopharyngeal carcinoma, malignant histiocytosis, paraneoplastic syndrome/hypercalcemia of malignancy, solid tumors, adenocarcinomas, sarcomas, malignant melanoma, hemangioma, metastatic disease, cancer related bone resorption, cancer related bone pain; the suppression of cancer metastasis; the amelioration of cancer cachexia; and the treatment of inflammatory diseases such as mesangial proliferative glomerulonephritis and the like. Such a method can optionally be used in combination with, by administering before, concurrently or after administration of such GD2 antibody, radiation therapy, an anti-angiogenic agent, a chemotherapeutic agent, a farnesyl transferase inhibitor or the like.

The present invention also provides a method for modulating or treating at least one GD2 mediated immune related disease, in a cell, tissue, organ, animal, or patient including, but not limited to, at least one of rheumatoid arthritis, juvenile rheumatoid arthritis, systemic onset juvenile rheumatoid arthritis, psoriatic arthritis, ankylosing spondilitis, gastric ulcer, seronegative arthropathies, osteoarthritis, inflammatory bowel disease, ulcerative colitis, systemic lupus erythematosis, antiphospholipid syndrome, iridocyclitis/uveitis/optic neuritis, idiopathic pulmonary fibrosis, systemic vasculitis/wegener's granulomatosis, sarcoidosis, orchitis/vasectomy reversal procedures, allergic/atopic diseases, asthma, allergic rhinitis, eczema, allergic contact dermatitis, allergic conjunctivitis, hypersensitivity pneumonitis, transplants, organ transplant rejection, graft-versus-host disease, systemic inflammatory response syndrome, sepsis syndrome, gram positive sepsis, gram negative sepsis, culture negative sepsis, fungal sepsis, neutropenic fever, urosepsis, meningococcemia, trauma/hemorrhage, burns, ionizing radiation exposure, acute pancreatitis, adult respiratory distress syndrome, rheumatoid arthritis, alcohol-induced hepatitis, chronic inflammatory pathologies, sarcoidosis, Crohn's pathology, sickle cell anemia, diabetes, nephrosis, atopic diseases, hypersensitivity reactions, allergic rhinitis, hay fever, perennial rhinitis, conjunctivitis, endometriosis, asthma, urticaria, systemic anaphylaxis, dermatitis, pernicious anemia, hemolytic disease, thrombocytopenia, graft rejection of any organ or tissue, kidney transplant rejection, heart transplant rejection, liver transplant rejection, pancreas transplant rejection, lung transplant rejection, bone marrow transplant (BMT) rejection, skin allograft rejection, cartilage transplant rejection, hone graft rejection, small bowel transplant rejection, fetal thymus implant rejection, parathyroid transplant rejection, xenograft rejection of any organ or tissue, allograft rejection, anti-receptor hypersensitivity reactions, Graves disease, Raynoud's disease, type B insulin-resistant diabetes, asthma, myasthenia gravis, antibody-meditated cytotoxicity, type III hypersensitivity reactions, systemic lupus erythematosus, POEMS syndrome (polyneuropathy, organomegaly, endocrinopathy, monoclonal gammopathy, and skin changes syndrome), polyneuropathy, organomegaly, endocrinopathy, monoclonal gammopathy, skin changes syndrome, antiphospholipid syndrome, pemphigus, scleroderma, mixed connective tissue disease, idiopathic Addison's disease, diabetes mellitus, chronic active hepatitis, primary billiary cirrhosis, vitiligo, vasculitis, post-MI cardiotomy syndrome, type IV hypersensitivity, contact dermatitis, hypersensitivity pneumonitis, allograft rejection, granulomas due to intracellular organisms, drug sensitivity, metabolic/idiopathic, Wilson's disease, hemachromatosis, alpha-1-antitrypsin deficiency, diabetic retinopathy, hashimoto's thyroiditis, osteoporosis, hypothalamic-pituitary-adrenal axis evaluation, primary biliary cirrhosis, thyroiditis, encephalomyelitis, cachexia, cystic fibrosis, neonatal chronic lung disease, chronic obstructive pulmonary disease (COPD), familial hematophagocytic lymphohistiocytosis, dermatologic conditions, psoriasis, alopecia, nephrotic syndrome, nephritis, glomerular nephritis, acute renal failure, hemodialysis, uremia, toxicity, preeclampsia, okt3 therapy, anti-cd3 therapy, cytokine therapy, chemotherapy, radiation therapy (e.g., including but not limited to asthenia, anemia, cachexia, and the like), chronic salicylate intoxication, sleep apnea, obesity, heart failure, sinusitis, inflammatory bowel disease, and the like. See, e.g., the Merck Manual, 12th-17th Editions, Merck & Company, Rahway, N.J. (1972, 1977, 1982, 1987, 1992, 1999), Pharmacotherapy Handbook, Wells et al., eds., Second Edition, Appleton and Lange, Stamford, Conn. (1998, 2000), each entirely incorporated by reference.

The present invention also provides a method for modulating or treating at least one infectious disease in a cell, tissue, organ, animal or patient, including, but not limited to, at least one of: acute or chronic bacterial infection, acute and chronic parasitic or infectious processes, including bacterial, viral and fungal infections, HIV infection/HIV neuropathy, meningitis, hepatitis (A, B or C, or the like), septic arthritis, peritonitis, pneumonia, epiglottitis, *E. coli* 0157:h7, hemolytic uremic syndrome/thrombolytic thrombocytopenic purpura, malaria, dengue hemorrhagic fever, leishmaniasis, leprosy, toxic shock syndrome, streptococcal myositis, gas gangrene, *mycobacterium tuberculosis, mycobacterium avium intracellulare, pneumocystis carinii* pneumonia, pelvic inflammatory disease, orchitis/epidydimitis, *legionella*, lyme disease, influenza a, epstein-barr virus, vital-associated hemaphagocytic syndrome, vital encephalitis/aseptic meningitis, and the like;

Any of such methods can optionally comprise administering an effective amount of at least one composition or pharmaceutical composition comprising at least one Anti-GD2 antibody to a cell, tissue, organ, animal or patient in need of such modulation, treatment or therapy.

Any method of the present invention can comprise administering an effective amount of a composition or pharmaceutical composition comprising at least one Anti-GD2 antibody to a cell, tissue, organ, animal or patient in need of such modulation, treatment or therapy. Such a method can optionally further comprise co-administration or combination therapy for treating such immune diseases or malignant diseases, wherein the administering of said at least one Anti-GD2 antibody, specified portion or variant thereof, further comprises administering, before concurrently, and/or after, at least one selected from at least one TNF antagonist (e.g., but not limited to a TNF antibody or fragment, a soluble TNF receptor or fragment, fusion proteins thereof, or a small molecule TNF antagonist), an IL-18 antibody or fragment, small molecule IL-18 antagonist or IL-18 receptor binding protein, an IL-1 antibody (including both IL-1 alpha and IL-1 beta) or fragment, a soluble IL-1 receptor antagonist, an antirheumatic (e.g., methotrexate, auranofin, aurothioglucose, azathioprine, etanercept, gold sodium thiomalate, hydroxychloroquine sulfate, leflunomide, sulfasalazine, radiation therapy, an anti-angiogenic agent, a chemotherapeutic agent, Thalidomidea muscle relaxant, a narcotic, a non-steroid anti-inflammatory drug (NSAID), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a fluoroquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an erythropieitin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, domase alpha (Pulmozyme), a cytokine or a cytokine antagonist. Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which is entirely incorporated herein by reference.

TNF antagonists suitable for compositions, combination therapy, co-administration, devices and/or methods of the present invention (further comprising at least one anti body, specified portion and variant thereof, of the present invention), include, but are not limited to, anti-TNF antibodies, antigen-binding fragments thereof, and receptor molecules which bind specifically to TNF; compounds which prevent and/or inhibit TNF synthesis, TNF release or its action on target cells, such as thalidomide, tenidap, phosphodiesterase inhibitors (e.g., pentoxifylline and rolipram), A2b adenosine receptor agonists and A2b adenosine receptor enhancers; compounds which prevent and/or inhibit TNF receptor signalling, such as mitogen activated protein (MAP) kinase inhibitors; compounds which block and/or inhibit membrane TNF cleavage, such as metalloproteinase inhibitors; compounds which block and/or inhibit TNF activity, such as angiotensin converting enzyme (ACE) inhibitors (e.g., captopril); and compounds which block and/or inhibit TNF production and/or synthesis, such as MAP kinase inhibitors.

Any method of the present invention can comprise a method for treating a GD2 mediated disorder or a disorder characterized by GD2 expression, comprising administering an effective amount of a composition or pharmaceutical composition comprising at least one Anti-GD2 antibody to a cell, tissue, organ, animal or patient in need of such modulation, treatment or therapy. Such a method can optionally further comprise co-administration or combination therapy for treating such immune diseases, wherein the administering of said at least one Anti-GD2 antibody, specified portion or variant thereof, further comprises administering, before concurrently, and/or after, at least one agent as described above.

Typically, treatment of pathologic conditions is effected by administering an effective amount or dosage of at least one Anti-GD2 antibody composition that total, on average, a range from at least about 0.01 to 500 milligrams of at least one Anti-GD2 antibody per kilogram of patient per dose, and preferably from at least about 0.1 to 100 milligrams antibody/kilogram of patient per single or multiple administration, depending upon the specific activity of contained in the composition. Alternatively, the effective serum concentration can comprise 0.1-5000 ug/ml serum concentration per single or multiple administration. Suitable dosages are known to medical practitioners and will, of course, depend upon the particular disease state, specific activity of the composition being administered, and the particular patient undergoing treatment in some instances, to achieve the desired therapeutic amount, it can be necessary to provide for repeated administration, i.e., repeated individual administrations of a particular monitored or metered dose, where the individual administrations are repeated until the desired daily dose or effect is achieved.

Preferred doses can optionally include 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration, or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 1.6, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000.mu.g/ml serum concentration per single or multiple administration, or any range, value or fraction thereof.

Alternatively, the dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. Usually a dosage of active ingredient can be about 0.1 to 100 milligrams per kilogram of body weight. Ordinarily 0.1 to 50, and preferably 0.1 to 10 milligrams per kilogram per administration or in sustained release form is effective to obtain desired results.

As a non-limiting example, treatment of humans or animals can be provided as a one-time or periodic dosage of at least one antibody of the present invention 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Dosage forms (composition) suitable for internal administration generally contain from about 0.1 milligram to about 500 milligrams of active ingredient per unit or container. In these pharmaceutical compositions the active ingredient will ordinarily be present in an amount of about 0.5-99.999% by weight based on the total weight of the composition.

For parenteral administration, the antibody can be formulated as a solution, suspension, emulsion or lyophilized powder in association, or separately provided, with a pharmaceutically acceptable parenteral vehicle. Examples of such vehicles are water, saline, Ringer's solution, dextrose solution, and 1-10% human serum albumin. Liposomes and non-aqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Formulations for parenteral administration can contain as common excipients sterile water or saline, polyalkylene glycols such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent such as aqueous solution or a sterile injectable solution or suspension in a solvent. As the usable vehicle or solvent, water, Ringer's solution, isotonic saline, etc. are allowed; as an ordinary solvent, or suspending solvent, sterile involatile oil can be used. For these purposes, any kind of involatile oil and fatty acid can be used, including natural or synthetic or semisynthetic fatty oils or fatty acids; natural or synthetic or semisynthetic mono- or di- or tri-glycerides. Parental administration is known in the art and includes, but is not limited to, conventional means of injections, a gas pressured needle-less injection device as described in U.S. Pat. No. 5,851,198, and a laser perforator device as described in U.S. Pat. No. 5,839,446 entirely incorporated herein by reference.

The invention further relates to the administration of at least one Anti-GD2 antibody by parenteral, subcutaneous, intramuscular, intravenous, intrarticular, intrabronchial, intraabdominal, intracapsular, intracartilaginous, intracavitary, intracelial, intracerebellar, intracerebroventricular, intrathecal, intra-Ommaya, intraocular, intravitreous, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, or transdermal means. At least one Anti-GD2 antibody composition can be prepared for use for parenteral (subcutaneous, intramuscular or intravenous) or any other administration particularly in the form of liquid solutions or suspensions; for use in vaginal or rectal administration particularly in semisolid forms such as, but not limited to, creams and suppositories; for buccal, or sublingual administration such as, but not limited to, in the form of tablets or capsules; or intranasally such as, but not limited to, the form of powders, nasal drops or aerosols or certain agents; or transdermally such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement"; Hsieh, D. S., Eds., pp. 59-90, Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways such as electroporation, or to increase the mobility of charged drugs through the skin such as iontophoresis, or application of ultrasound such as sonophoresis (U.S. Pat. Nos. 4,309,989 and 4,767,402) (the above publications and patents being entirely incorporated herein by reference).

For pulmonary administration, preferably at least one Anti-GD2 antibody composition is delivered in a particle size effective for reaching the lower airways of the lung or sinuses. According to the invention, at least one Anti-GD2 antibody can be delivered by any of a variety of inhalation or nasal devices known in the art for administration of a therapeutic agent by inhalation. These devices capable of depositing aerosolized formulations in the sinus cavity or alveoli of a patient include metered dose inhalers, nebulizers, dry powder generators, sprayers, and the like. Other devices suitable for directing the pulmonary or nasal administration of antibodies are also known in the art. All such devices can use of formulations suitable for the administration for the dispensing of antibody in an aerosol. Such aerosols can be comprised of either solutions (both aqueous and non aqueous) or solid particles. Metered dose inhalers like the Ventolin® metered dose inhaler, typically use a propellent gas and require actuation during inspiration (See, e.g., WO 94/16970, WO 98/35888). Dry powder inhalers like Turbuhaler™ (Astra), Rotahaler® (Glaxo), Diskus® (Glaxo), devices marketed by Inhale Therapeutics, to name a few, use breath-actuation of a mixed powder (U.S. Pat. No. 4,668,218 Astra, EP 237507 Astra, WO 97/25086 Glaxo, WO 94/08552 Dura, U.S. Pat. No. 5,458,135 Inhale, WO 94/06498 Fisons, entirely incorporated herein by reference). Nebulizers like the Ultravent® nebulizer (Mallinckrodt), and the Acorn II® nebulizer (Marquest Medical Products) (U.S. Pat. No. 5,404,871 Aradigm, WO 97/22376), the above references entirely incorporated herein by reference, produce aerosols from solutions, while metered dose inhalers, dry powder inhalers, etc. generate small particle aerosols. These specific examples of commercially available inhalation devices are intended to be a representative of specific devices suitable for the practice of this invention, and are not intended as limiting the scope of the invention. Preferably, a composition comprising at least one Anti-GD2 antibody is delivered by a dry powder inhaler or a sprayer. There are several desirable features of an inhalation device for administering at least one antibody of the present invention. For example, delivery by the inhalation device is advantageously reliable, reproducible, and accurate. The inhalation device can optionally deliver small dry particles, e.g. less than about 10 um, preferably about 1-5 um, for good respirability.

A spray including GD2 antibody composition protein can be produced by forcing a suspension or solution of at least one Anti-GD2 antibody through a nozzle under pressure. The nozzle size and configuration, the applied pressure, and the liquid feed rate can be chosen to achieve the desired output and particle size. An electrospray can be produced, for example, by an electric field in connection with a capillary or nozzle feed. Advantageously, particles of at least one Anti-GD2 antibody composition protein delivered by a sprayer have a particle size less than about 10 um, preferably in the range of about 1 um to about 5 um, and most preferably about 2 um to about 3 um.

Formulations of at least one Anti-GD2 antibody composition protein suitable for use with a sprayer typically include antibody composition protein in an aqueous solution at a concentration of about 0.1 mg to about 100 mg of at least one Anti-GD2 antibody composition protein per ml of solution or mg/gm, or any range or value therein, e.g., but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/ml or mg/gm. The formulation can include agents such as an excipient, a buffer, an isotonicity agent, a preservative, a surfactant, and, preferably, zinc. The formulation can also include an excipient or agent for stabilization of the antibody composition protein, such as a buffer, a reducing agent, a bulk protein, or a carbohydrate. Bulk proteins useful in formulating antibody composition proteins include albumin, protamine, or the like. Typical carbohydrates useful in formulating antibody composition proteins include sucrose, mannitol, lactose, trehalose, glucose, or the like. The antibody composition protein formulation can also include a surfactant, which can reduce or prevent surface-induced aggregation of the antibody composition protein caused by atomization of the solution in forming an aerosol. Various conventional surfactants can be employed, such as polyoxyethylene fatty acid esters and alcohols, and polyoxy ethylene sorbitol fatty acid esters. Amounts will generally range between 0.001 and 14% by weight of the formulation. Especially preferred surfactants for purposes of this invention are polyoxyethylene sorbitan monooleate, polysorbate 80, polysorbate 20, or the like. Additional agents known in the art for formulation of a protein such as GD2 antibodies, or specified portions, or variants, can also be included in the formulation.

Antibody composition protein can be administered by a nebulizer, such as jet nebulizer or an ultrasonic nebulizer. Typically, in a jet nebulizer, a compressed air source is used to create a high-velocity air jet through an orifice. As the gas expands beyond the nozzle, a low-pressure region is created, which draws a solution of antibody composition protein through a capillary tube connected to a liquid reservoir. The liquid stream from the capillary tube is sheared into unstable filaments and droplets as it exits the tube, creating the aerosol. A range of configurations, flow rates, and baffle types can be employed to achieve the desired performance characteristics from a given jet nebulizer. In an ultrasonic nebulizer, high-frequency electrical energy is used to create vibrational, mechanical energy, typically employing a piezoelectric transducer. This energy is transmitted to the formulation of antibody composition protein either directly or through a coupling fluid, creating an aerosol including the antibody composition protein. Advantageously, particles of antibody composition protein delivered by a nebulizer have a particle size less than about 10 um, preferably in the range of about 1 um to about 5 um, and most preferably about 2 um to about 3 um.

Formulations of at least one Anti-GD2 antibody suitable for use with a nebulizer, either jet or ultrasonic, typically include a concentration of about 0.1 mg to about 100 mg of at least one Anti-GD2 antibody protein per ml of solution. The formulation can include agents such as an excipient, a buffer, an isotonicity agent, a preservative, a surfactant, and, preferably, zinc. The formulation can also include an excipient or agent for stabilization of the at least one Anti-GD2 antibody composition protein, such as a buffer, a reducing agent, a bulk protein, or a carbohydrate. Bulk proteins useful in formulating at least one Anti-GD2 antibody composition proteins include albumin, protamine, or the like. Typical carbohydrates useful in formulating at least one Anti-GD2 antibody include sucrose, mannitol, lactose, trehalose, glucose, or the like. The at least one Anti-GD2 antibody formulation can also include a surfactant, which can reduce or prevent surface-induced aggregation of the at least one Anti-GD2 antibody caused by atomization of the solution in forming an aerosol. Various conventional surfactants can be employed, such as polyoxyethylene fatty acid esters and alcohols, and polyoxyethylene sorbital fatty acid esters. Amounts will generally range between 0.001 and 4% by weight of the formulation. Especially preferred surfactants for purposes of this invention are polyoxyethylene sorbitan mono-oleate, polysorbate 80, polysorbate 20, or the like. Additional agents known in the art for formulation of a protein such as antibody protein can also be included in the formulation.

In a metered dose inhaler (MDI), a propellant, at least one Anti-GD2 antibody, and any excipients or other additives are contained in a canister as a mixture including a liquefied compressed gas. Actuation of the metering valve releases die mixture as an aerosol, preferably containing particles in the size range of less than about 10 um, preferably about 1 um to about 5 um, and most preferably about 2 um to about 3 um. The desired aerosol particle size can be obtained by employing a formulation of antibody composition protein produced by various methods known to those of skill in the art, including jet-milling, spray drying, critical point condensation, or the like. Preferred metered dose inhalers include those manufactured by 3M or Glaxo and employing a hydrofluorocarbon propellant.

Formulations of at least one Anti-GD2 antibody for use with a metered-dose inhaler device will generally include a finely divided powder containing at least one Anti-IL-6 antibody as a suspension in a non-aqueous medium, for example, suspended in a propellant with the aid of a surfactant. The propellant can be any conventional material employed for this purpose, such as chlorofluorocarbon, a hydrochlorofluorocarbon, a hydrofluorocarbon, or a hydrocarbon, including trichlorofluoromethane, dichlorodifluoromethane, dichlorotetrafluoroethanol and 1,1,1,2-tetrafluoroethane, HFA-134a (hydrofluoroalkane-134a), HFA-227 (hydrofluoroalkane-227), or the like. Preferably the propellant is a hydrofluorocarbon. The surfactant can be chosen to stabilize the at least one Anti-GD2 antibody as a suspension in the propellant, to protect the active agent against chemical degradation, and the like. Suitable surfactants include sorbitan trioleate, soya lecithin, oleic acid, or the like. In some cases solution aerosols are preferred using solvents such as ethanol. Additional agents known in the art for formulation of a protein can also be included in the formulation.

One of ordinary skill in the art will recognize that the methods of the current invention can be achieved by pulmonary administration of at least one Anti-GD2 antibody compositions via devices not described herein.

Formulations for oral administration rely on the co-administration of adjuvants (e.g., resorcinols and nonionic surfactants such as polyoxyethylene oleyl ether and n-hexadecylpolyethylene ether) to increase artificially the permeability of the intestinal walls, as well as the co-administration of enzymatic inhibitors (e.g., pancreatic trypsin inhibitors, diisopropylfluorophosphate (DFF) and trasylol) to inhibit enzymatic degradation. The active constituent compound of the solid-type dosage form for oral administration can be mixed with at least one additive, including sucrose, lactose, cellulose, mannitol, trehalose, raffinose, maltitol, dextran, starches, agar, arginates, chitins, chitosans, pectins, gum tragacanth, gum arabic, gelatin, collagen, casein, albumin, synthetic or semisynthetic polymer, and glyceride. These dosage forms can also contain other type(s) of additives, e.g., inactive diluting agent, lubricant such as magnesium stearate, paraben, preserving agent such as sorbic acid, ascorbic acid, alpha.-tocopherol, antioxidant such as cysteine, disintegrator, binder, thickener, buffering agent, sweetening agent, flavoring agent, perfuming agent, etc.

Tablets and pills can be further processed into enteric-coated preparations. The liquid preparations for oral administration include emulsion, syrup, elixir, suspension and solution preparations allowable for medical use. These preparations can contain inactive diluting agents ordinarily used in said field, e.g., water. Liposomes have also been described as drug deliver systems for insulin and heparin (U.S. Pat. No. 4,239,754). More recently, microspheres of artificial polymers of mixed amino acids (proteinoids) have been used to deliver pharmaceuticals (U.S. Pat. No. 4,925,673). Furthermore, carrier compounds described in U.S. Pat. No. 5,879,681 and U.S. Pat. No. 5,871,753 are used to deliver biologically active agents orally are known in the art.

For absorption through mucosal surfaces, compositions and methods of administering at least one Anti-GD2 antibody include an emulsion comprising a plurality of submicron particles, a mucoadhesive macromolecule, a bioactive peptide, and an aqueous continuous phase, which promotes absorption through mucosal surfaces by achieving mucoadhesion of the emulsion particles (U.S. Pat. No. 5,514,670). Mucous surfaces suitable for application of the emulsions of the present invention can include corneal, conjunctival, buccal, sublingual, nasal, vaginal, pulmonary, stomachic, intestinal, and rectal routes of administration. Formulations for vaginal or rectal administration, e.g. suppositories, can contain as excipients, for example, polyalkyleneglycols, vaseline, cocoa butter, and the like. Formulations for intranasal administration can be solid and contain as excipients, for example, lactose or can be aqueous or oily solutions of nasal drops. For buccal administration excipients include sugars, calcium stearate, magnesium stearate, pregelinatined starch, and the like (U.S. Pat. No. 5,849,695).

For transdermal administration, the at least one Anti-GD2 antibody is encapsulated in a delivery device such as a liposome or polymeric nanoparticles, microparticle, microcapsule, or microspheres (referred to collectively as microparticles unless otherwise stated). A number of suitable devices are known, including microparticles made of synthetic polymers such as polyhydroxy acids such as polylactic acid, polyglycolic acid and copolymers thereof, polyorthoesters, polyanhydrides, and polyphosphazenes, and natural polymers such as collagen, polyamino acids, albumin and other proteins, alginate and other polysaccharides, and combinations thereof (U.S. Pat. No. 5,814,599).

It can be sometimes desirable to deliver the compounds of the present invention to the subject over prolonged periods of time, for example, for periods of one week to one year or more from a single administration. Various slow release, depot or implant dosage forms can be utilized. For example, a dosage form can contain a pharmaceutically acceptable non-toxic salt of the compounds that has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzyl-ethylenediamine or ethylenediamine; or (c) combinations of (a) and (b) e.g. a zinc tannate salt. Additionally, the compounds of the present invention or, preferably, a relatively insoluble salt such as those just described, can be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed for encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above can also be formulated in cholesterol matrix silastic pellets, particularly for use in animals. Additional slow release, depot or implant formulations, e.g. gas or liquid liposomes are known in the literature (U.S. Pat. No. 5,770,222 and "Sustained and Controlled Release Drug Delivery Systems", J. R. Robinson ed., Marcel Dekker, Inc., N.Y., 1978).

The contents of all cited references (including literature references, issued patents, published patent applications, and co-pending patent applications) cited throughout this application are hereby expressly incorporated by reference.

Other features of the invention will become apparent in the course of the following descriptions of exemplary embodiments which are given for illustration of the invention and are not intended to be limiting thereof.

The following MATERIALS AND METHODS were used in the examples that follow.

Materials and Methods

Cell Culture and Human Tissues

Human neuroblastoma cell line LAN-1 was provided by Dr. Robert Seeger (Children's Hospital of Los Angeles, Los Angeles, Calif.), and NB1691 by Dr. Peter Houghton (St. Jude Children's Research Hospital, Memphis, Term.). NK-92MI was obtained from American Type Culture Collection (ATCC), Manassas, Va. All cell lines were grown in F10 [RPMI 1640 medium supplemented with 10% fetal bovine serum (Hyclone, South Logan, Utah), 2 mM glutamine, 100 U/ml penicillin, and 100 ug/ml streptomycin] at 37° C. in a 5% $CO_2$ incubator. Normal tissues as well as solid tumor samples of different histological types obtained at Memorial Sloan-Kettering Cancer Center (MSKCC) were snap frozen in liquid nitrogen. Written informed consent was obtained from the patients and/or their guardians in accordance to the guidelines of the institutional review board of MSKCC.

Monoclonal Antibodies

Murine 3F8 was a mouse IgG3 antibody with kappa light chain (Cheung et al., 1985, Cancer Res 45, 2642-9). Monoclonal antibodies 3F8 (mouse IgG3, kappa), 5F11 (mouse IgM, kappa), and 8H9 (mouse IgG1, kappa) reactive with neuroblastoma have been previously described (Cheung et al, 1985, supra; Cheung et al., 2004, J Nucl Med 45, 867-77; Modak et al., 2001, Cancer Res 61, 4048-54). They were produced as ascites and purified by affinity chromatography: protein A (GE Healthcare, Piscataway, N.J.) for 3F8, protein G for 8H9, and Clq-sepharose (Pierce, Rockford, Ill.) for 5F11. These antibodies were >90% pure by SDS-PAGE. F(ab')2 fragments were prepared by pepsin digestion as previously reported (Cheung et al., 1988, J Clin Invest 81, 1122-28). Anti-GD2 hybridoma ME361 and TIB114 (N.S.7), a hybridoma secreting an IgG3 control antibody, were obtained from ATCC. 14.G2a was purchased from BD Biosciences, San Jose, Calif. Chimeric 14.18 was kindly provided by Dr. Stephen Gillies of Lexigen Pharmaceuticals, Lexington, Mass. MAB1027 (anti-B7-H3 MoAb) was purchased from R&D System, Minneapolis, Minn. Mouse IgG3 antibody S220-51 specific for GD2 was purchased from Northstar Bioproducts, Cape Cod, Mass.

Construction of the hu3F8-IgG1, hu3F8-IgG4, ch3F8-IgG1, and ch3F8-IgG4 Antibody Producer Lines.

Based on human homologs of m3F8, CDR sequences of both heavy and light chains of m3F8 were grafted into the human IgG1 framework and optimized. From two heavy chain and two light chain genes, four versions of hu3F8 were designed. These hu3F8 genes were synthesized and optimized for CHO cells (Blue Heron Biotechnology, Bothhell, Wash. or Genscript, Piscataway, N.Y.). Using the bluescript vector (Eureka, Calif.), these heavy and light chain genes of hu3F8 were transfected into DG44 cells and selected with G418 (InVitrogen, Calif.). When transfected into Mage1.5 CHO cells (Eureka, Calif.), special IgG glycoforms are produced. Similarly mouse VH and VL sequences were grafted onto human IgG1 and IgG4 frameworks to make the ch3F8-IgG1 and ch3F8-IgG4 recombinant antibodies.

Purification of hu3F8 and ch3F8

Hu3F8 and ch3F8 producer lines were cultured in Opticho serum free medium (InVitrogen, Calif.) and the mature supernatant harvested. Protein A affinity column was preequilibrated with 25 mM sodium citrate buffer with 0.15 M NaCl, pH 8.2. Bound hu3F8 was eluted with 0.1 M citric acid/sodium citrate buffer, pH 3.9 and alkalinized (1:10 v/v ratio) in 25 mM sodium citrate, pH 8.2. It was passed through a Sartobind-Q membrane and concentrated to 5-10 mg/ml in 25 mM sodium citrate, 0.15 M NaCl, pH 8.2. Stability studies were performed on hu3F8-IgG1 in 25 mM sodium citrate 0.15 M NaCl pH 8.2 versus PBS pH 7.4 in the presence or absence of 0.7 mg/ml of tween 80 (Sigma).

SDS-PAGE 2 ug each of the proteins is analyzed by SDS-PAGE under nonreducing or reducing conditions using 4-15% Tris-Glycine Ready Gel System (Bio-Rad, Hercules, Calif.). Invitrogen SeeBlue Plus2 Pre-Stained Standard was used as the protein molecular weight marker. After electrophoresis, the gel was stained using PIERCE's GelCode Blue Stain Reagent. The gel was scanned using Bio-Rad Fluor-S Multi-Imager (Bio-Rad), and the band intensity quantified with Quantity One software (Bio-Rad).

Quantitation of hu3F8 and ch3F8 by ELISA

Microtiter plates were coated with GD2 at 20 ng per well. 150 ul per well of 0.5% BSA in PBS (diluent) was added to each plate for at least 30 min at ambient temperature to block excess binding sites, the washed at least three times with PBS. A purified batch of hu3F8-IgG1 (stock concentration 1 mg/ml) was used to construct a standard curve starting with 0.5 ug/ml followed by two fold dilutions. 100 ul of standard and samples (also diluted 2-fold) were added to each well and incubated for 2.5 hours at 37° C. After washing plates 5 times with PBS, 100 ul of goat anti human-IgG (H+L) (Jackson Research Laboratory) diluted at 1:3500 in diluent added to each well and incubated for 1 hour at 4° C. ELISA color reaction was developed with chromogen OPD (Sigma) with the substrate hydrogen peroxide for 30 min at RT in the dark. The reactions were stopped with 5N $H_2SO_4$ and the OD read with ELISA plate reader MRX (Dynex) at 490. Based on the standard curve, quantitation of hu3F8 supernatants was calculated in ug/ml or ug/mg of protein.

In Vitro Binding Kinetics on Biacore T-100 Biosensor (Biacore AB of GE Healthcare, Uppsala, Sweden)

CM5 sensor chip (Research grade) and related reagents were purchased from Biacore USA (Piscataway, N.J.). The gangliosides GM1 was from ALEXIS Biochemicals (AXXORA LLC, San Diego, Calif.), and GD2 from Advanced ImmunoChemical (Long Beach, Calif.). GM1 was dissolved (0.5 mg/ml) in 90% ethanol, 10% methanol (v/v) and GD2 was dissolved (0.5 mg/ml) in ethanol. Gangliosides were directly immobilized onto the CM5 sensor chip via hydrophobic interaction. Reference surface was immobilized with GM1. GM1 was 1:1 diluted with 100% ethanol and then was 1/5 diluted in HBS-E buffer (10 mM HEPES, pH 7.4, 150 mM NaCl, and 3 mM EDTA). Diluted GM1 (50 µg/ml) was injected (300 µl) at a flow rate of 15 µl/min over 20 min. Extensive washing was followed with 10 mM NaOH (typically five washes of 20 µl at a flow rate of 5 µl/min) until a stable baseline was obtained. Active surface was immobilized with GD2 and GM1 in 1:1 ratio. GD2 and GM1 were 1:1 diluted with 100% ethanol and mixed in 1:1 ratio. The mixture of GD2 and GM1 was 1/5 diluted in HBS-E buffer (10 mM HEPES, pH 7.4, 150 mM NaCl, and 3 mM EDTA). Diluted mixture of GD2 and GM1 (50 µg/ml) was injected (300 µl) at a flow rate of 15 µl/min over 20 min. Extensive washing was followed with 10 mM NaOH (typically five washes of 20 µl at a flow rate of 5 µl/min) until a stable baseline was obtained.

Purified Anti-GD2 MoAbs were diluted in HBS-E buffer containing 250 mM NaCl at varying concentrations (50-1600 nM) prior to analysis. 2. Samples (60 µl) were injected over the sensor surface at a flow rate of 30 µl/min over 2 min. Following completion of the association phase, dissociation was monitored in HBS-E buffer containing 250 mM NaCl for 300 sec at the same flow rate. At the end of each cycle, the surface was regenerated using 50 µl 20 mM NaOH at a flow rate of 50 µl/min over 1 min and 100 µl 4M MgCl2 at a flow rate of 50 µl/min over 2 min. The biosensor curves obtained following injection of the samples over immobilized GD2 were subtracted with the control curves obtained with the samples injected over immobilized GM1 prior to kinetics analysis. The data were analyzed by the bivalent analyte model and default parameter setting for the rate constants using the Biacore T-100 evaluation software, and the apparent association on rate constant (kon, ka1), dissociation off rate constant (koff, kd1) and equilibrium dissociation constant (KD=kd1/ka1) were calculated.

Hu3F8 and ch3F8 were further characterized with rat anti-3F8 anti-idiotypic antibodies (Cheung et al., 1993, Int J Can 54, 499-505). These rat IgG1 antibodies were also digested into Fab fragments and purified using Fab preparation kit (Pierce Protein Research Products, Thermo Fisher Scientific). Their reactivities of ch3F8 and hu3F8 were assayed by ELISA and by BIACORE.

ELISA for Cross Reactivity with Other Gangliosides

GD2, GM2, GD1a, GD1b, GT1b, as well as GD3, GM3, GM1, GD1a were coated at 20 ng per well in 90% ethanol. Following air drying, wells were blocked with 0.5% BSA in PBS at 150 ul per well for 1 hour at RT before washing for 3 times in PBS. Antibodies were added in triplicates at 1 ug/ml (100 ul per well) in 0.5% BSA. For background subtraction, wells with (1) no antigen and (2) no sample were used. Following incubation for 2 hour at 37° C. and washing with PBS 5 times, HRP-goat anti mouse IgG (Jackson Laboratory, diluted to 1:1000) for mouse antibodies (e.g. 3F8) or HRP-goat anti human IgG (Jackson Laboratory, 1:1000) for humanized antibodies were used. Following additional incubation for 1 hour at 4° C. and further washing, the OD was read using ELISA plate reader MRX (Dynex) at 490 and cross reactivity expressed as % maximal binding to GD2.

Biotinylation of Antibody

Biotin (Long Arm)-N-hydroxysuccinimide ester (BNHS, Vector Laboratories, Inc., Burlingame, Calif.) was dissolved in dimethylsulfoxide (DMSO) at a concentration of 50 mg/ml. The biotinylating reagent is added at 1/10 weight ratio of reagent to the antibody. With occasional stirring, the reaction mixture was incubated at RT for 2 hours. The biotinylated antibody was dialyzed in PBS at RT for 4 hours or at 4° C. overnight. The immunoreactivity of biotinylated antibody was compared to the native antibody and ensured that EC50 be within 20% of each other.

Tissue Cross-Reactivity by Immunostaining 5-7 micron thick frozen sections were cut using cryostat, fixed with 250 ul of acetone at −20° C. for 30 min. After washing slides with PBS, slides were exposed to freshly prepared 0.1% hydrogen peroxide for 15 min at RT. After washing, blocking Avidin solution (VECTOR Avidin-Biotin blocking kit) was added and incubated for 20 min at RT. After washing, a drop of a blocking Biotin solution (VECTOR Avidin-Biotin blocking kit) was added and incubated for 20 min at RT. After further washing, >100 ul blocking serum (10% horse serum freshly diluted in PBS) was added and incubated for 1 h at RT. This step can be longer. Note: Must not reuse serum. After aspirating the blocking serum from each slide, 100 ul of 1 ug/ml biotinylated MOPC21 (negative control) or biotinylated antibody diluted in 1% horse serum was added and incubated for 1 hour at RT. After washing, 100 ul of Avidin-Biotin Complex [ABC] (Vectastain ABC kit, VECTOR) at a 1:100 dilution in PBS was added and incubated for 30 min at RT. After washing, 200 ul of the dye (DAB Peroxidase Substrate kit, VECTOR) was added to each section and color allowed to develop for 2 min (until the desired intensity of staining was achieved based on color development in the standard). Sections were washed in running tap water for 5 min and counterstained with stock Myer's hematoxylin, and further washing done in running tap water for 5 min. Slides were dehydrated sequentially in 75%, then 95%, and then 100% ethyl alcohol. Final dehydrating step was in xylene or xylene substitute. One drop of fresh Cytoseal was added, and then section sealed with cover slip.

Direct Cytotoxicity

Antibodies were tested for their direct effect on tumor cell growth and survival in the absence of human serum or human effector cells. Tumor targets were dissociated with 2 mM EDTA or Trypsin-EDTA, washed and plated into 96-well flat bottomed plates in F10 at $1.2 \times 10^3$ to $3.5 \times 10^4$ per well. After incubation for 24 hours in a CO2 incubator at 37° C., 5% CO2, increasing concentrations of antibodies in F10 are added to each well. Control wells received F10 alone. After incubation for 72 hours at 37° C. in 5% CO2, WST-8 reagent was added to each well and incubated in the dark in a CO2 incubator at 37° C. for 2-6 hours. OD was read at 450 nm and 690 nm using ELISA plate reader MRX (Dynex). WST-8 assay was validated using direct cell counting using Trypan Blue (Sigma) or Beckman Coulter Counter (Beckman Coulter, Brea, Calif.).

Antibody Dependent Cellular Cytotoxicity (ADCC) by $^{51}$Chromium Release

Target cells were detached with 2 mM EDTA in Ca2+ Mg2+ free PBS and washed in 10% calf medium (Gibco) in RPMI 1640 (F10). 100 μCi of $^{51}$Cr was inucubated with $10^6$ target cells to in a final volume of 250 μl and incubated for 1 hr at 37° C. with gentle resuspension of pellet at 15-minute intervals. Cells were then washed and resuspended in 250 ul F10 and incubated for 30 min in 37° C. After washing, cells were counted and viability determined with trypan blue (Sigma) and quickly plated onto 96 well U-bottom plates. Peripheral blood from normal volunteers were collected into heparinized tubes. The blood was mixed with 3% dextran/PBS and kept at RT for 20 minute to sediment the red cells. White cells were then ficolled and separated into peripheral blood mononuclear cells (PBMC) and granulocytes (PMN) for PBMC-ADCC and PMN-ADCC, respectively. Cells were washed in F10, counted and viability determined. PBMC-ADCC was done in the presence of 10 U/ml of IL-2 and PMN-ADCC in 2 ng/ml of GMCSF. Final volume of ADCC was 250 ul/well. Antibodies were diluted in F10 from 1 ug/ml in 3-fold or 5-fold dilutions. Plates were centrifuged at 500 rpm for snap spin at RT and then incubated in a 37° C., 5% CO2 incubator for 4 hrs. Released $^{51}$Cr in the ADCC supernatant was collected for gamma counting. Total release was determined using 10% SDS and background spontaneous release was determined with F10 only without effectors. A E:T ratio of 50:1 was generally used. Similarly, ADCC assays were carried out using NK92-MI cells stably transfected with the human CD16 or human CD32 Fc receptors. Unlike PBMC or PMN, no cytokines were needed in the assay. E:T ratio was generally kept at 20:1.

$$\% \text{ specific lysis} = \frac{(\text{experimental} - \text{background})}{(\text{total} - \text{background})} \times 100\%$$

Iodination of Antibodies

Iodination using $^{124}$I and $^{131}$I was carried out using the iodogen method (Divgi et al., 2007, Lancet Oncol. 8, 304-10). A glass vial was coated with 50 μg of iodogen and 100 μg of IgG in 50 mM phosphate buffer (pH 7.4) was added together with 1 mCi of $^{124}$I (or $^{131}$I). Iodine 124 was produced on site by cyclotron at MSKCC. 10 mCi of $^{124}$I (0.02-0.05 mL) in 0.05 M NaOH was mixed with 1 mg of MoAb (~0.5 mL), 0.063 mL 1 M Tris base and 0.4 mL 0.2 M sodium phosphate pH 7.4 in the reaction vial. The reaction was allowed to proceed on ice for 15 minutes before the solution was removed and purified by size exclusion chromatography with a P6 size exclusion column and an eluant of 1% BSA in PBS.

Radioimmunoassay (RIA)

The method of Lindmo was used to estimate immunoreactivity (Lindmo et al., 1984, J Immunol Methods 72, 77-89). Radiolabeled MoAb was diluted with 1% BSA until 50 μl contained about 15,000-20,000 cpm (approximately 1-1.5 uCi/3 ml). 50 μl was added to 500 μl 0.5% BSA containing 6.25, 3.75, 2.5, 2.2, 1.9 million tumor cells and mixed for 1 hour at ambient temperature. After centrifuge at 1500 rpm for 5 minutes the supernatant was removed and washed with 1 ml ice cold 0.5% BSA. Following another centrifugation at 1500 rpm for 5 minutes, the cell pellets were counted in the gamma counter. Background counts in the absence of cells or iodinated antibodies were subtracted and immunoreactivity estimated by the Lindmo method (Lindmo et al., 1984, supra).

Biodistribution of MoAb in Xenografted Mice

Athymic nude mice xenografted with sc LAN1 neuroblastoma tumors were used to study pharmacokinetics/biodistribution and anti-tumor properties. Tumors were measured with a caliper. Experiments commenced when sc tumors reached ~200 mg. ~100 uCi of radioiodinated antibody per mouse was injected intravenously and animals sacrificed usually at 48 hours, and their organs removed and counted in a gamma counter (Packard Instruments, Perkin Elmer). These organs included skin, liver, spleen, kidney, adrenal, stomach, small intestine, large intestine, bladder, femur, muscle, tumor, heart, lung, spine, and brain. Based on the uCi accumulated in the organ and the organ weight, % injected dose (ID)/gm of mouse was calculated. Tumor to normal tissue ratios of % ID/gm were also calculated.

Sugar Analysis

Monosaccharide and oligosaccharide analyses of antibodies were carried by the Complex Carbohydrate Research Center, Athens, Ga. Monosaccharide analysis was assayed by HPAEC. N-glycan profiling was carried out by MALDI-MS.

Example 1

Amino Acid Sequences of Chimeric-IgG1 and Four Humanized IgG1

The CDRs of the heavy and light chains of m3F8 were grafted onto human IgG1 frameworks based on their homology with human frameworks IGG HV3-33 and IGKV3-15, respectively. From two heavy chain and two light chain designs, four versions of hu3F8 were gene synthesized and expressed in DG44 cells. The amino acid sequences of chimeric human heavy and light chains are shown SEQ ID NO:1 and 2, respectively, humanized heavy chain sequence huH1-gamma1 in SEQ ID NO:4, huH2-gamma1 in SEQ ID NO:6, and humanized light chain sequences huL1-kappa in SEQ ID NO:5 and huL2-kappa in SEQ ID NO:7.

When expressed as whole IgG, the four hu3F8-IgG1 are named hu3F8-H1L1-IgG1, hu3F8-H1L2-IgG1, hu3F8-H2L2-IgG1 and hu3F8-H2L1-IgG1. Additional constructs were made replacing the heavy chain sequences of m3F8 and hu3F8-H1L1-IgG1 with the human IgG4 framework (chimeric heavy chain gamma4, SEQ ID NO:4 and humanized 3F8 heavy chain gamma 4, SEQ ID NO:8) transfected into DG44 cells using the bluescript vectors. In another set of experiments, the hu3F8-H1L1-IgG1 sequence was transfected into a special MAGE1.5 CHO cell line selected for a special glycosylation signature (See Materials and Methods). Both chimeric and humanized 3F8 were purified using standard protein A affinity chromatography.

On SDS gel, chimeric and humanized antibodies migrated as IgG with the appropriate size heavy and light chains; and by HPLC they all eluted as whole IgG with <10% aggregate formation (data not shown). By ELISA they all bound to GD2 with similar avidity. By FACS analysis (LAN-1, data not shown) antibodies showed an optimal antibody concentration (~0.1-1 ug/million cells) beyond which mean fluorescence intensity (MFI) dropped because of cell death at higher antibody concentrations. With M14 melanoma, cell death did not occur with excess antibody beyond 1 ug per million cells (data not shown). IgG4 tended to have lower MFI because of preferential reactivity of the fluorescent second antibody with human IgG1. Compared to the other hu3F8 constructs, hu3F8-H1L1-IgG1 was the most stable after freezing and thawing, retaining its binding to tumor cells by FACS and by ELISA (data not shown). By sugar analysis hu3F8-IgG1n had mostly mannose and some N-acetyl-glucosamine, in contrast to hu3F8-IgG1 and hu3F8-IgG4 which contained near equal molar ratios of fucose and N-acetyl-glucosamine (table 1).

Example 2

Avidity Measurements by SPR (BIACORE)

With GD2 coated onto CM5 chips, kinetics of antibody binding (kon, koff and KD) were compared by Surface Plasmon Resonance using BIACORE T-100 at low GD2 density at low GD2 density (table 2). Both $k_{off}$ and $K_D$ were improved proportionally for all antibodies at high GD2 density (data not shown). The Sensorgrams of representative antibodies at different antibody concentrations were compared at both low GD2 density (data not shown) and at high GD2 density (data not shown) on the BIACORE CM5 chips.

TABLE 1

| Monosaccharide composition | | | |
|---|---|---|---|
| Antibody Residue | hu3F8-IgG1n mole % | hu3F8-IgG1 mole % | hu3F8-IgG4 mole % |
| Arabinose (Ara) | 0 | 0 | 0 |
| Ribose (Rib) | 0 | 0 | 0 |
| Rhamnose (Rha) | 0 | 0 | 0 |
| Fucose (Fuc) | 0 | 15.1 | 13.2 |
| Xylose (Xyl) | 0 | 0 | 0 |
| Glucuronic Acid (GlcUA) | 0 | 0 | 0 |
| Galacturonic acid (GalUA) | 0 | 0 | 0 |
| Mannose (Man) | 95.2 | 44.1 | 49 |
| Galactose (Gal) | 0 | 0 | 0 |
| Glucose (Glc) | 0 | 0 | 0 |
| N Acetyl Mannosamine (ManNAc) | 0 | | |
| N Acetyl Galactosamine (GalNAc) | 0 | 0 | 0 |
| N Acetyl Glucosamine (GlcNAc) | 4.8 | 40.8 | 37.8 |
| Heptose(Hep) | 0 | 0 | 0 |
| 3 Deoxy-2-manno-2 Octulsonic acid (KDO) | 0 | 0 | 0 |
| Sum | 100 | 100 | 100 |

The slow $k_{off}$ of antibodies translated into a slower washoff when antibodies were reacted with GD2-postive tumor cells. Here LAN-1 cells (data not shown) or M14 cells (data not shown) were reacted with monoclonal antibodies and washed multiple times in wash buffer. With each wash, the remaining antibodies on the cell surface were detected using a secondary FITC-labeled goat anti-mouse antibody. MFI was expressed as a percent of the baseline (i.e. after first wash). On LAN-1 cells, 3F8 and anti-B7-H3 8H9 antibodies had slow wash off (~80% retention after 10 washes) compared to 14.G2a (~30% retention, data not shown). Similarly for M14 tumor cells, by the $5^{th}$ wash, there was substantial difference in the retention of antibody on tumor cells. While 3F8, 3F8-(Fab')2, and hu3F8-IgG1 (all with slow koff) had >80% retention, other Anti-GD2 antibodies 14.G2a (mIgG2a), ME361 (mIgG2a), and S220-51 (mIgG3) (all with fast koff by BIACORE) leaked off to <30%. Hu3F8-IgG1, hu3F8-IgG4, ch3F8-IgG1 and ch3F8-IgG4 also reacted specifically to rat anti-3F8 anti-idiotypic antibodies (Cheung et al., 1993, Inter J Cancer 54, 499-505) and their Fab fragments with high avidity in ELISA and by SPR (See Methods).

Example 3

Crossreactivity with Other Antigens

In cross reactivity studies, hu3F8-H1L1-IgG1 had similar profile as ch3F8-IgG1 and m3F8 (table 3). There was low level of cross reactivity with GD1b expressed as percent OD by ELISA relative to the OD on solid phase GD2. There was no cross reactivity of m3F8, hu3F8 or 14.G2a with human N-CAM (Patel et al., 1989, Br. J. Cancer 60, 861-866) either by Western blots or by SPR (data not shown).

TABLE 2

Binding kinetics of chimeric and humanized 3F8 by SPR (BIACORE-T100)

| Antibody | n | kon | koff | KD (nM) |
|---|---|---|---|---|
| ch3F8-IgG1 | 2 | 1.15E+05 | 1.45E−03 | 13 ± 3 |
| hu3F8-H1L1-IgG1 | 12 | 9.19E+04 | 1.03E−03 | 11 ± 1 |
| hu3F8-H1L2-IgG1 | 3 | 1.74E+05 | 1.07E−03 | 7 ± 2 |
| hu3F8-H2L1-IgG1 | 3 | 1.92E+05 | 5.04E−03 | 31 ± 14 |
| hu3F8-H2L2-IgG1 | 3 | 1.52E+05 | 3.51E−03 | 26 ± 11 |
| hu3F8-H1L1-IgG1n | 3 | 9.76E+04 | 6.88E−04 | 11 ± 2 |
| ch3F8-IgG4 | 2 | 9.40E+04 | 1.28E−03 | 14 ± 2 |
| hu3F8-H1L1-IgG4 | 3 | 1.18E+05 | 1.76E−03 | 15 ± 1 |
| m3F8 | 10 | 1.75E+05 | 1.04E−03 | 5 ± 1 |
| m3F8 (Fab')2 | 3 | 1.44E+05 | 1.23E−03 | 9 ± 3 |
| 14.G2a | 6 | 1.30E+05 | 1.11E−02 | 100 ± 26 |

Example 4

Direct Cytotoxicity

When these antibodies were added to neuroblastoma cells in vitro, they induced direct cell death and slowed down in vitro cell growth. When assayed by WST-8 in a 3-day culture system, m3F8 and hu3F8 had similar potency when their EC50s were compared (see table 4), in contrast to 14.G2a which was ~10-fold weaker.

TABLE 3

Cross reactivity with other gangliosides by ELISA

| Antibody | # exp | GM2/GD2 | GD1a/GD2 | GD1b/GD2 | GT1b/GD2 | GD3/GD2 | GQ1b/GD2 |
|---|---|---|---|---|---|---|---|
| 14.G2a | 7 | 0 | 0 | 0 | 0 | 0 | 0 |
| m3F8 | 19 | 0 | 0 | 4.1% | 0 | 0 | 0 |
| ch3F8-IgG1 | 5 | 0 | 0.2% | 8.8% | 0 | 0.2% | 0 |
| ch3F8-IgG4 | 6 | 0 | 0 | 6.1% | 0 | 0 | 0 |
| hu3F8-H1L1-IgG1 | 44 | 0 | 0 | 4.5% | 0 | 0 | 0 |
| hu3F8-H1L2-IgG1 | 4 | 0 | 0 | 2.9% | 0 | 0 | Nd |
| hu3F8-H2L1-IgG1 | 8 | 0 | 0 | 1.9% | 0 | 0 | 0 |
| hu3F8-H2L2-IgG1 | 9 | 0 | 0 | 1.6% | 0 | 0 | 0 |
| hu3F8-H1L1-IgG4 | 11 | 0 | 0 | 3.1% | 0 | 0 | 0 |
| hu3F8-H1L1-IgG1n | 6 | 0 | 0 | 6.9% | 1.0% | 0 | 0 |

Example 5

Antibody Dependent Cell Mediated Cytotoxicity

The four hu3F8 IgG1 antibodies (H1L1, H1L2, H2L1, H2L2) were compared in ADCC assays using volunteer PBMC (data not shown) and volunteer PMN (data not shown) as effectors. Other than H1L2, all three hu3F8 had comparable PBMC-ADCC. But most importantly, they were all superior to m3F8 by a factor of >10-100.

TABLE 4

Direct cytotoxicity of neuroblastoma LAN-1 in the presence of antibodies
Direct Cytotoxicity

| Antibody | EC50 (ug/ml) |
|---|---|
| m3F8 | 1.9 |
| hu3F8-IgG1-H1L2 | 10.5 |
| hu3F8-IgG1-H2L1 | 16.5 |
| hu3F8-IgG1-H2L2 | 17.5 |
| hu3F8-IgG1-H1L1 | 5.1 |
| hu3F8-IgG1n | 2.6 |
| hu3F8-IgG4 | 3.1 |
| ch3F8-IgG1 | 4.5 |
| ch3F8-IgG4 | 6.4 |
| 14.G2a | 47.1 |

Hu3F8-H1L1-IgG1 (abbreviated as hu3F8-IgG1) was the most stable in vitro and was chosen for further characterization. Ch3F8-IgG1, hu3F8-IgG1, hu3F8-IgG1n, 14.G2a, and m3F8 were compared in ADCC assays against LAN-1 using PBMC (data not shown) or PMN (data not shown) as effectors. The ADCC potencies of these antibodies were computed as the ratio (EC50 for 3F8)/(EC50 for MoAb) (table 5). Relative to m3F8, hu3F8-IgG1 was 217 fold stronger in PBMC-ADCC, and 19 stronger in PMN-ADCC. For hu3F8-IgG1n, it was 3901 fold and 5 fold, respectively. In addition, the maximal cytotoxicity achieved with both chimeric and humanized 3F8 were substantially and consistently higher than that of m3F8 or 14.G2a, irrespective if it was PBMC-ADCC or PMN-ADCC.

In order to examine the capability of MoAb in ADCC for individual FcR in isolation (in the absence of inhibitory FcR), we tested ADCC using NK92 cells. NK92 cells do not carry human FcR on their cell surface. When transfected with human CD16 and CD32, they could mediate efficient ADCC. When these effector cells were tested against neuroblastoma LAN-1 targets, hu3F8-IgG1n was substantially (~10 fold) more efficient than hu3F8-IgG1, which was in turn more efficient (12 fold) than m3F8 in CD16-ADCC (data not shown). In contrast, with CD32 as FcR, the potency was nearly 10-fold higher for hu3F8-IgG1 compared to that of hu3F8-IgG1n (data not shown). Similar trends were observed when melanoma M14 was used as targets. Hu3F8-IgG1n was ~10-fold more efficient than hu3F8-IgG1 or ch3F8-IgG1, which were in turn-20-fold more efficient than m3F8 or 14G.2a (data not shown) in CD16-ADCC. In contrast, hu3F8-IgG1, hu3F8-IgG1n and ch3F8-IgG1 were similar when CD32 was the FcR, all >10-fold more efficient than m3F8 in CD32-ADCC (table 6). IgG4 subclass antibodies had <3% of CMC activity, minimal CD16-ADCC activity, but better C32-ADCC than m3F8.

Example 6

Complement Mediated Cytotoxicity

In human complement mediated lysis (CMC), the different hu3F8 IgG1 forms (H1L1, H1L2, H2L1, and H2L2) were comparable in efficiency (table 6). Ch3F8 and hu3F8 were 40-60%, while 14G.2a and ch14.18 were 4-12% as efficient in CMC as m3F8 (table 6).

TABLE 5

Relative antibody potency in ADCC and CMC against neuroblastoma LAN-1

| Antibody | LAN1-PBMC Potency | LAN1-PMN Potency | LAN1-CMC Potency | LAN1-CD16 Potency | LAN1-CD32 Potency |
|---|---|---|---|---|---|
| 14.G2a | 0.03 | 1.0 | 0.12 | 4 | 2 |
| ch14.18 | 11 | 3 | 0.04 | 2 | 8 |
| ch3F8-IgG1 | 390 | 18 | 0.64 | 24 | 13 |
| ch3F8-IgG4 | 0 | 1 | 0.01 | 0 | 3 |
| hu3F8-IgG1 | 217 | 19 | 0.40 | 12 | 15 |
| hu3F8-IgG1n | 3901 | 5 | 0.41 | 106 | 2 |
| hu3F8-IgG4 | 0 | 4 | 0.03 | 0 | 1 |
| m3F8 | 1 | 1 | 1 | 1 | 1 |
| hu3F8-H1L2-IgG1 | 7 | 11 | 0.22 | 12 | 17 |
| hu3F8-H2L1-IgG1 | 355 | 14 | 0.64 | 1 | 7 |
| hu3F8-H2L2-IgG1 | 390 | 15 | 0.47 | 10 | 3 |

Example 7

Targeting Human Neuroblastoma Xenografts

Hu3F8-IgG1, hu3F8-IgG1n, and hu3F8-IgG4 were radiolabeled with $^{131}$I with comparable immunoreactivity of around 40-45% (Table 7). Their biodistributions at 48 hours were compared with that of $^{131}$I-m3F8 in mice bearing sc LAN-1 neuroblastoma xenografts. Tumor uptake when measured by % ID/gm was comparable between hu3F8-IgG1 (29.6%) and m3F8 (28.6%), both nearly double those of hu3F8-IgG1n and hu3F8-IgG4 (data not shown). Tumor to normal tissue ratios were comparable among these 4 antibodies for NB LAN-1 xenografts. In comparison, with melanoma M14 both the % ID/gm and the Tumor to normal tissue ratios of all three hu3F8 antibodies were similar to that of m3F8 (data not shown).

TABLE 6

Relative antibody potency in ADCC and CMC against Melanoma M14

| Antibody | M14-CD16 Potency | M14-CD32 Potency |
|---|---|---|
| 14.G2a | 1 | 6 |
| ch14.18 | 9 | 21 |
| ch3F8-IgG1 | 39 | 17 |
| ch3F8-IgG4 | 0 | 0.5 |
| hu3F8-IgG1 | 20 | 31 |
| hu3F8-IgG1n | 252 | 10 |
| hu3F8-IgG4 | 0.1 | 4 |
| m3F8 | 1 | 1 |
| hu3F8-H1L2-IgG1 | 40 | 44 |
| hu3F8-H2L1-IgG1 | 6 | 9 |
| hu3F8-H2L2-IgG1 | 15 | 11 |

Example 8

Treatment of Neuroblastoma Xenografts

Mice xenografted with established human neuroblastoma LAN-1 (0.5-1 cm diameter) were treated with iv m3F8 or hu3F8-H1L1-IgG1 twice weekly for 4 weeks. Tumor response and mice survival were monitored. Delay in tumor growth was dependent on hu3F8-H1L1-IgG1 antibody dose (200 ug>100 ug>20 ug, data not shown). Survival of mice receiving 100-200 ug were significantly longer (p=0.003) than mice receiving PBS control or m3F8 (data not shown).

TABLE 7

RIA of 131I-labeled antibodies in biodistribution studies

| LAN1 | m3F8 | hu3F8-IgG1 | hu3F8-IgG1n | hu3F8-IgG4 |
|---|---|---|---|---|
| RIA | 45% | 45% | 42% | 40% |
| TCA | 94% | 96% | 96% | 96% |
| # mice | 18 | 19 | 17 | 19 |

Discussion

Anti-GD2 antibody is a proven therapy for GD2-positive neuroblastoma (Yu et al., N Engl J Med 363:1324-1334, 2010). The murine antibody 14.18 and its derivatives (14.G2a and ch14.18) have provided benchmarks for future improvements of anti-GD2 therapy. We chose murine IgG3 antibody m3F8 for clinical development because of its 10-fold slower koff during GD2 binding compared to 14.G2a or ch14.18. Among patients with chemoresistant metastatic neuroblastoma in the bone marrow, m3F8 plus GMCSF induced 80% complete remissions (Kushner et al., 2001, J Clin Oncol 19, 4189-94). However, human anti-mouse antibodies (HAMA) can diminish the effect of the murine antibody by neutralizing its ability to bind to its antigen, by blocking the direct effect of the antibody and by accelerating the clearance of the antibody from circulation. Genetic engineering to change murine to human IgG frameworks should reduce the HAMA response. Ch14.18 and hu14.18 (both derived from the VH and VL of 14.G2a) have minimal immunogenicity in patients. We therefore tested the chimeric and humanized forms of 3F8 as potential next generation Anti-GD2 antibodies One criterium for successful chimerization and humanization is the preservation of affinity during genetic engineering. This is particularly uncertain with CDR grafting in the humanization process. The preservation of a slow koff in ch3F8 and hu3F8 was reassuring. But more importantly, the preservation and enhancement of in vitro effector function, as well as in vivo tumor targeting plus in vivo therapeutic properties could be critical. Both ch3F8-IgG1 and hu3F8-IgG1 showed >200 fold more efficient PBMC-ADCC than m3F8, while PMN-ADCC were >20 fold. In addition, the special glycoform hu3F8-IgG1n had >3500 fold more efficient PBMC-ADCC, and 5 fold more efficient PMN-ADCC than those of m3F8. In sharp contrast, for CMC, ch3F8 and hu3F8 had lower complement activating ability than m3F8.

This large improvement in ADCC is most desirable given recent evidence for its role in the anti-tumor effects of monoclonal antibodies in patients. Among lymphoma patients treated with rituximab, both high affinity FcR2A and FcR3A were shown to have better response and survival advantage (Weng and Levy, 2003, J Clin Oncol 21, 3940-7). While the high affinity receptor FcR3A translated into <10 improvement in ADCC in vitro (Niwa et al., 2004, Clin Cancer Res 10, 6248-55), overall response and time to progression improved by 200% (Weng and Levy, 2003, supra). When metastatic breast cancer was treated with Herceptin, patients with high affinity FcR3A had better overall response (83% versus 35%, p=0.03), and longer progression-free survival (p=0.005)(Musolino et al., 2008, J Clin Oncol 26, 1789-96). For metastastic colorectal cancer treated with Cetuximab, patients with low affinity FcR2A and FcR3A had comparable hazard ratios as patients with mutated KRAS (Bibeau et al., 2009, J Clin Oncol 27, 1122-9). With murine 3F8, patients with the high affinity FcR3A receptor for m3F8 on myeloid cells were shown to have better survival (Cheung et al., 2006, J Clin Oncol 24, 2885-90).

While binding affinity and effector functions are critical for therapeutic applications, cross-reactivity can pose unexpected toxicity issues. We showed that these chimeric and humanized forms for 3F8 had comparable cross-reactivity patterns as the murine 3F8 both by ELISA assays with purified gangliosides, as well as by immunohistochemistry on a panel of normal humans tissues (data not shown). Similar to m3F8, both chimeric and humanized forms of 3F8 showed low levels of reactivity to GD1b when compared to GD2. GD1b has been shown to be highly prevalent ganglioside among neuroblastoma tumors, especially when differentiated by retinoids (Hettmer et al., 2004, Br J Cancer 91, 389-97; Gong et al., 2002, Brain 125, 2491-506). This maybe relevant since cis-retinoic acid is routinely given to patients undergoing immunotherapy for high-risk neuroblastoma. However, anti-GD1b antibodies have also been associated with sensory ataxic neuropathies (Gong et al., 2002, supra). Nevertheless, the safety profile of m3F8 (with similar cross reactivity to GD1b) with no permanent or late sensory neuropathies in more than 500 patients was reassuring.

Complement-mediated cytotoxicity (CMC) is unusually effective against human neuroblastoma (Saarinen et al., 1985, Proc Amer Assoc Cancer Res 26, 291) because of their low expression of CD55 (Cheung et al., 1987, Proc Natl Am Assoc Cancer Res 28, 387) and CD59 (Chen et al., 2000, supra). All Anti-GD2 antibodies mediate efficient complement mediated cytotoxicity, and m3F8 seems particularly efficient. Yet, studies of rituximab have suggested a negative role of complement activation in down regulating ADCC (Wang et al., 2009, Blood 114, 5322-30). In clinical studies, higher activity of complement component C1qA was associated with less favorable response to rituximab therapy (Racila et al., 2008, Clin Cancer Res 14, 6697-703). For anti-GD2 antibodies, complement activation was thought to be responsible for the pain side effects (Navid et al., Curr Cancer Drug Targets 10:200-209, 2010) hence the Fc-CH2 domain mutated version (hu14.18K322A) currently in clinical trial. Given these considerations, an overdrive of CMC is probably not desirable. It is reassuring that both ch3F8 and hu3F8 had slightly less efficient CMC.

Example 9

Using Antibody to Block Acute Pain Side Effects

It was hypothesized that antibody with slow koff but depleted of ADCC or CMC activity could be used to block GD2 on nerve fibers surrounding the perivascular space. Heat treatment of 3F8 (HM3F8) depletes its ADCC and CMC activities without affecting its GD2 binding (Kushner et al. 2011, J Clin Oncol 29, 1168-1174). When rats were pre-injected with heat-treated 3F8, their pain response to a subsequent injection of 5-10 molar excess of native 3F8 was substantially reduced. More importantly, anti-tumor effect was not compromised. In a phase I clinical trial (IRB-05015, NCT00450307), 30 patients with resistant neuroblastoma (NB) received one to two cycles of 3F8 plus granulocyte-macrophage colony-stimulating factor in the outpatient setting. 3F8 dosing began at 20 mg/m$^2$/d and increased by 20 mg/m$^2$/d in the absence of dose-limiting toxicity (DLT). Pre-medication included analgesics, antihistamines, and 5-minute infusions of 2 mg/m$^2$ HM3F8. Opioid use was compared with a contemporary control group treated with 3F8 at 20 mg/m$^2$/d but no HM3F8. Dose escalation stopped at 160 mg/m$^2$/d because of drug supply limitations; even through this dosage level, analgesic requirements were similar to historical controls, and there were no DLTs. Analgesic requirements at 3F8 dosage levels through 80 mg/m$^2$/d were significantly less compared with controls. Anti-NB activity occurred at all dosages. This multifold dose escalation of 3F8 was feasible and suggested that HM3F8 could modify toxicity without blunting anti-NB activity.

Pain Blocking Potential of hu3F8-IgG4

Based on the clinical results of the HM3F8, we hypothesize that perivascular pain fibers can be preferentially blocked by a small dose of an antibody devoid of CMC or ADCC function. Although heating of m3F8 destroys its CMC and ADCC functions (while retaining binding), heat modified hu3F8 retains near full CMC and ADCC functions. The inability of hu3F8-IgG4 to activate CMC and ADCC in different NB cell lines such as Lan1, NMB7, SKNLP, BE(1)N and SHEP1 (Table 8 and data not shown) makes this antibody subclass a viable alternative for HM3F8. Unlike heating with unknown effects on antibody structure and immunogenicity, hu3F8-IgG4 is an engineered protein. Besides the absence of CMC and ADCC function, IgG4 subclass has unique biochemical properties. Typically induced by chronic antigen stimulation, they are known to interfere with immune complex formation by other antibody isotypes, thereby dampening the inflammatory reactions (Losen et al., 2008, Ann NY Acad Sci 1132, 174-9). Most importantly, it has a natural ability to reduce itself to monovalency, thereby losing its ability to compete with hu3F8-IgG1 after a period of hours in blood (van der Neut Kolfschoten et al., 2007, Science 317, 1554-7). Such monovalency derives from its known property to exchange Fab arms by swapping a heavy chain and attached light chain (half-molecule) with a heavy-light chain pair from another IgG4 molecule, which results in monovalency towards the specific antigen in question (e.g. GD2).

TABLE 8

| Antibody potency using NK92-CD16 ADCC as effectors on different NB lines | | | | | |
|---|---|---|---|---|---|
| | LAN1 | NMB7 | SKNLP | BE(1)N | SHEP1 |
| 14G2a | 0.4 | 1 | 1 | 1 | 1 |
| ch14.18 | 4 | 94 | 8 | 2 | 3 |
| hu3F8-IgG1 | 26 | 1428 | 23 | 68 | 3 |
| hu3F8-IgG4 | 0 | 0 | 0 | 0 | 0 |
| m3F8 | 1 | 1 | 1 | 1 | 1 |
| HM3F8 | 0.2 | — | — | — | — |

Rat Allodynia Model

The rat model was used to test the ability of hu3F8-IgG4 to block pain side effects (MSK protocol #09-05-010). Both m3F8 (an efficient activator of rat complement, Bergman et al., 2000, Cancer Immunol Immunother 49, 259-66) and hu3F8 were used to induce allodynia. Hu3F8-IgG4 (0.1, 0.25 or 0.5 mg/kg) was administered as iv push 30 minutes prior to iv m3F8 (5 mg/kg), or hu3F8-IgG1 (5 mg/kg), or ch14.18 (5 mg/kg). Other groups receive heat modified m3F8 (HM3F8) or control antibodies instead of hu3F8-IgG4. Von Frey filaments method was used to evaluate pain at baseline prior to and after MoAb injection (Chassaing et al., 2006, Br J Clin Pharmacol 61, 389-97; Benani et al., 2003, Eur J Neurosci 18, 2904-14).

Effect of hu3F8-IgG4 on Biodistribution and Efficacy of $^{131}$I-hu3F8-IgG1

Neuroblastoma (LAN-1) tumors were planted subcutaneously in groups of female NOD/SCID/IL2-gc$^{null}$ immunodeficient mice (n=10 per group) with low serum IgG. Mice were injected with human IgG at 1 gm/kg 24 h prior to experiment. Hu3F8-IgG4 (0.1, 0.25 or 0.5 mg/kg) or control huIgG4 (0.1, 0.25 or 0.5 mg/kg), or HM3F8 (0.5 mg/kg), or saline were administered as iv push, 30 minutes prior to m3F8, or hu3F8-IgG1 or ch14.18 (5 mg/kg) trace labeled with $^{131}$I-labeled respective MoAb (50 uCi/mouse). Blood was collected from the tail at 1, 3, 6, 12, 24, 36, 48 and 96 h. In biodistribution studies mice were sacrificed at 2 time points (24 h and 48 h after $^{131}$I-MoAb injection) for tissue counts. The major organs were removed and counted in a gamma counter with a known volume of the injectate and the data expressed as a percentage ID/gm tissue. Pharmacokinetics analysis was be carried out by non-compartmental analysis of the serum concentration-time data using the WinNonlin software program (Pharsight Corp., Mountain View, Calif.). In separate sets of experiments, xenografted mice were treated similarly but without $^{131}$I-trace label, and their sc tumor response measured overtime for 2 months.

The ability of hu3F8-IgG4 to block allodynia in the rat can be compared to that of heat-treated m3F8. Based on the dose response curves of the blocking antibody used (while keeping the challenge by native m3F8, or hu3F8-IgG1 or ch14.18, all at 5 mg/kg) a relative potency in blocking allodynia in the rat can be derived. We anticipate hu3F8-IgG4 to be equivalent or more efficient when compared to heat-treated 3F8 in blocking allodynia. These studies will provide preclinical rationale for transitioning hu3F8-IgG4 to a clinical trial.

Example 10

Optimization of Hu3F8 Framework Sequence for Enhanced Stability

In the process of humanizing murine antibodies, framework residues at structurally important positions are often back mutated to the murine sequence in order to preserve both antibody stability and antigen binding (Honegger, A, 2008, Engineering Antibodies for Stability and Efficient Folding, In: Therapeutic Antibodies. Handbook of Experimental Pharmacology, 181).
Materials and Methods
Structural Model of m3F8 Variable Domain A homology model of m3F8 variable domain was created using MODELER (Eswar et al., 2006, Curr Prot Bioinfor, Supplement 15, 5.6.1-5.6.30) in Discovery Studio (Accerlys, San Diego, Calif.). The crystal structure of malaria antigen AMA1 antibody Fab (Protein Data Bank code 2Q8A) was chosen as a template for the variable light chain (84% identity). The crystal structure of antibody 13G5 Fab (Protein Data Bank code 2GJZ) was chosen as the template for the variable heavy chain.
Crystal Structure of m3F8 Fab Fragment Fab fragments of m3F8 were generated by papain digestion using a standard Fab preparation kit (Pierce Biotechnology, Rockford, Ill.). The purified m3F8 was concentrated to 12 mg/ml in 20 mM HEPES pH 6.5 and was crystallized in a hanging drop by vapor diffusion at 16° C. against a reservoir containing Hampton Index reagent D9 containing 0.1M Tris pH 8.5, 25% w/v PEG 3350 (Hampton Research, Aliso Viejo, Calif.). The droplet was formed by mixing 1 μl of protein solution and 1 of reservoir solution. The crystals were protected by cryoprotectant containing 25% glycerol, 0.1M Tris pH 8.5, 25% w/v PEG 3350. Data was collected at the Argonne Advanced Photon Source beamline 24IDC. The crystals belong to the space group C2 and diffract to 1.7 Å resolution.

The Fab structure was solved by molecular replacement using Phaser (CCP4 suite) (McCoy et al., 2007, J Appl Crystallogr 40, 658-674) and PDB entry 2AJU as the search model (Qin et al., 2008, J Biol Chem 283, 29473-84). The best molecular replacement model was refined using Refmac5 (Murshudov et al., 1997, Acta Crystallogr. D: Biol. Crystallogr 53, 240-255), manual fitting was performed with O (The CCP4 suite: programs for protein crystallography. Acta Crystallogr., D: Biol. Crystaollogr. 50 (1994) 760-763), adding solvent with Arp-Warp (Lamzin and Wilson, 1993, Acta Crystallogr, D: Biol. Crystallogr. 49, 129-147). The final model contained two polypeptide chains of m3F8 Fab and 585 solvent molecules.
Computational Analysis of m3F8 Crystal Structure Based on the human templates IgHV3-33-HC and IGKV3-15-LC, each humanizing mutation that would be introduced into the framework on m3F8 was analyzed using computational chemistry methods. The crystal structure of m3F8 was simulated using CHARMm (Chemistry at Harvard Molecular mechanics) force fields (Brooks et al, 2009, J. Comp Chem 30, 1545-1615), and the effect of each point mutation was calculated from the difference between the folding free energy of the mutated structure and the wild type protein. Generalized Born approximation was used to account for the effect of the solvent and all electrostatic terms were calculated as a sum of coulombic interactions and polar contributions to the solvation energy. A weighted sum of the van der Waals, electrostatic, entropy and non-polar terms was calculated for each point mutation. All calculations were performed using Discovery Studio 3.0 (Accelrys, San Diego, Calif.).
Results For the hu3F8-H1L1 heavy chain sequence, the human IgG heavy chain sequence IgHV3-33-HC was used as a template and back mutations were made at positions 5, 9, 16, 19, 20, 24, 28, 29, 30, 40, 48, 49, 67, 71, 76, 78, 81, 86, and 92. For the hu3F8-H1L1 light chain, the human IgG light chain sequence IGKV3-15-LC was used as a template and back mutations were made at positions 1, 7, 9, 15, 19, 21, 22, 43, 45, 58, 60, 67, 70, 73, 78, 80, and 87. The back mutations were deduced based on a homology models of m3F8, and involved determining that these whether the mutations would influence the folding of the CDR loops or affect backbone stability (mutations involving Gly and Pro).

To verify the accuracy of the homology model and further enhance the humanization strategy, the crystal structure of m3F8 was solved at 1.7 Å (data not shown). The homology model of m3F8 variable region was superimposed with the solved crystal structure (data not shown). The homology model for the majority of the framework region outside of the CDR closely matched the experimentally derived crystal structure. Notable differences were, however, observed in the CDR region, particularly in loops H3, H2, and L3. The homology model also failed to accurately predict any of the interactions at the VH-VL interface that are crucial to the stability of the Fv structure. There are 6 pairs of amino acids that hydrogen bond at the VH-VL interface and two pairs of amino acids that participates in pi-interactions (Table 10). After the crystal structure of m3F8 was solved, computational analysis was applied to determine the energetic effect of each humanizing mutations based on IgHV3-33-HC and IGKV3-15-LC templates. The difference in the folding free energy was calculated for each mutation. Based on this analysis, five of the humanizing mutations were found to be destabilizing to the overall fold of m3F8 (see Table 9). These include heavy chain positions 11 and 21, and light chain positions 1, 10, 12, 40, and 97. It was also determined that humanizing mutations involving Pro and Gly in the light chain at positions 40 and 97, respectively, would significantly affect the backbone flexibility. These five destabilizing mutation in addition to the two Gly/Pro mutations were considered candidates for back mutation and are included in the sequence of hu3F8-H3L3 (SEQ ID NO:9 and 10). The computational analysis of the m3F8 crystal structure also identified five humanizing mutations that would have neutral affects to antibody stability (data not shown). These mutations are positions 24 and 56 of the light chain and at positions 20, 58 and 92 of the heavy chain. These mutations were not included in sequence of hu3F8-H1L1 (SEQ ID NO:4 and 5), which was based on the homology model, but are included in the design on hu3F8-H3L3.

An analysis of the VH-VL interface of the crystal structure of m3F8 was done to preserve each of the hydrogen bonds and pi-interactions in hu3F8 (Table 10). Of the 15 amino acids that are involved in interface interactions, 14 were preserved in the design of hu3F8-H1L1 and hu3F8-H3L3. The one missing interaction involves Ser43 in the light chain. This mutation was added to the design of hu3F8-L1 and hu3F8-L3 to generate Hu3F8-L1S and Hu3F8-L3S.

These stability-enhanced frameworks would not have possible with the current state of the art, which involves the use of homology modeling to design stable humanized frameworks. The use of an experimentally derived crystal structure of m3F8 in combination with computational analysis using force field methods were needed to design novel antibodies with enhanced stability profiles.

TABLE 9

Computational analysis of humanizing mutations on crystal structure of m3F8 Fv
Mutations that will destabilize the mouse structure or alter backbone flexibility.

| Mutation | ΔG (kcal/mol) | Observation |
| --- | --- | --- |
| Light chain S1E | 0.82 | Destabilizing |
| Light chain F10T | 1.36 | Destabilizing |
| Light chain L12S | 1.98 | Destabilizing |
| Heavy chain L11V | 1.90 | Destabilizing |
| Heavy chain T21S | 1.71 | Destabilizing |
| Light chain A40P | −1.03 | Changes backbone flexibility |
| Light chain G97Q | −1.42 | Changes backbone flexibility |

Mutations that Will have Negligible Affects on Stability.

| Mutation | ΔG (kcal/mol) | Observation |
| --- | --- | --- |
| Light chain K24R | −0.30 | Neutral effect |
| Light chain S56T | 0.24 | Neutral effect |
| Light chain V58I | −0.73 | Neutral effect |
| Heavy chain I20L | −0.44 | Neutral effect |
| Heavy chain M92V | −0.56 | Neutral effect |

TABLE 10

Important interactions between amino acids at the VH-VL interface of m3F8 Fv crystal structure

| Interaction | Light chain residue | Heavy chain residue |
| --- | --- | --- |
| H-bond | Gln38 | Gln39 |

TABLE 10-continued

Important interactions between amino acids at the VH-VL interface of m3F8 Fv crystal structure

| Interaction | Light chain residue | Heavy chain residue |
| --- | --- | --- |
| H-bond | Ser43 | Gly110 |
| H-bond | Tyr55 | Asp107 |
| H-bond | Gln89 | Tyr104 |
| H-bond | Tyr92 | Arg98 |
| H-bond | Tyr36 | Leu106 |
| Pi-Pi | Tyr92 | Trp47 |
| Pi-sigma | Tyr92 | Tyr104 |

Example 11

Higher Affinity 3F8 Antibody Based on Computational Analysis of 3F8:GD2 Interaction The crystal structure of m3F8 was used as a template for computational studies to determine the molecular details of antigen recognition. The GD2 antigen is composed of a penta-saccharide head group linked to a ceramide lipid tail. In the absence of an experimentally derived 3F8:GD2 co-complex, computational docking was attempted with the GD2 penta-saccharide head group only, where the ceramide moiety was replaced by a methyl-group. The GD2 penta-saccharide molecule presented a major challenge for docking studies given the state of the field in computational docking. Firstly, the docking of large flexible ligands are difficult to accurately predict. The GD2 head group has over 30 rotatable bonds. There is no established docking protocol that has been reported to be accurate for a ligand with such a high degree of flexibility. Secondly, the GD2 head group is a carbohydrate molecule, and there are few reports on the accuracy of docking studies when force field methods are applied to carbohydrate molecules. Thirdly, the GD2 head group is a special class of carbohydrates since it contains two charged groups found in its sialic acid moieties. No established docking methods have been shown to accurately predict the binding conformation of such large, flexible, and charged carbohydrates.

One docking algorithms that has been reported to be reliable for predicting the binding conformation of oligosaccharides (although not containing charged sialic residues) is GLIDE (Agostino et al., 2009, J Chem Inf Model 49, 2749-60). The report showed that GLIDE outperformed AutoDock, GOLD, and FlexX in predicting the binding conformation of oligosaccharides to antibodies as compared to experimentally derived co-crystal structures. It should be noted that none of the antigens tested were larger a tetra-saccharide. Another promising docking algorithm in the literature was CDOCKER (Wu et al., 2003, J. Comp Chem 24, 1549), a CHARMm based docking algorithm that was shown to outperform DOCK, FlexX, and GOLD in accurately predicting the docking conformation of ligands with 8 or more rotatable bonds (Erickson et al., 2004, J Med Chem 47, 45-55). It should be noted that oligosaccharides were not analyzed in the study, and the ligands tested were much smaller and less flexible that the GD2 head group (>30 rotatable bonds).

A head-to-head comparison between GLIDE and CDOCKER was performed in docking ligands similar to GD2 (sialic acid containing oligosaccharides) using three available test cases from the protein data bank (PDB code 2HRL: Siglec-7 in complex with GT1b; PDB code 3BWR: Simian virus VP1 in complex with GM1; and PDB code 3HMY: Tetanus toxin HCR/T in complex with GT2). In all two of three test cases, CDOCKER was able to accurately predict the correct binding mode of the respective oligosaccharide (within 2 Ångstom root-mean-square deviation).

GLIDE inaccurately docked two to the three test cases (>2 Ångstom root-mean-square deviation) and failed to find a docked pose in the third test case. (see Table 11). By this analysis, CDOCKER outperformed GLIDE in docking charged oligosaccharides.

GLIDE failed in each one of the cases (see Table 11). CDOCKER was then used to dock the GD2 penta-saccharide head group to the antigen-binding pocket of the crystal structure of m3F8. The top docked structure was then energy minimized using CHARMm force fields. The analysis indicated 14 amino acids that directly interact with the GD2 head group (Table 12). Each of these positions was then mutated in silico to all of the possible amino acids and the CHARMm based interaction energies were calculated. The highest interacting mutants are listed in Table 13. Based on this approach, one mutation (Heavy Chain Gly54Ile) was predicted to increase the interaction energy significantly. Computational modeling showed that substitution of the Gly at position 54 to Ile in the CDR3 of the heavy chain would change the shape of the binding pocket and increase the contact with the GD2 ligand. This analysis was used to add the heavy chain mutation Gly54Ile to the CDR regions of the sequences of huH1-gamma1 and huH3-gamma1 to create huH1I-gamma1 and huH3I-gamma respectively.

Docking Methods

GLIDE docking was performed using the Schrodinger Suite 2009 (Schrodinger, New York, N.Y.). OPLS force fields were used to parameterize the proteins and ligands. Top ligand poses were clustered within a root-mean-square deviation of 2.0 Å and scored by GlideScore.

CDOCKER docking and interaction energy measurements were performed using Discovery Studio 3.0 (Accelrys, San Diego, Calif.). CHARMm force fields were used to parameterize the proteins and ligands. Top ligand poses were clustered within a root-mean-square deviation of 2.0 Å and scored by CDOCKER Interaction Energy.

TABLE 11

Comparison of docking algorithms GLIDE versus CDOCKER in predicting known protein:ganglioside complexes

| Method | Protein | Ligand | RMSD of top pose (Å) |
|---|---|---|---|
| CDOCKER | Siglec-7 | GT1b | 1.3 |
|  | Simian virus VP1 | GM1 | 3.2 |
|  | Tetanus toxin HCR/T | GT2 | 1.2 |
| GLIDE | Siglec-7 | GT1b | 9.6 |
|  | Simian virus VP1 | GM1 | Unable to find docked pose |
|  | Tetanus toxin HCR/T | GT2 | 4.2 |

Example 12

Improving Effector Functions by Enhancing Affinities for Antigen and Fc Receptor (FcR)

Anti-GD2 MoAb is a proven therapy for chemo-resistant metastatic neuroblastoma (NB), with ch14.18 providing a benchmark for next generation MoAb. The combination of anti-GD2 MoAb mouse 3F8 (m3F8) and granulocyte-macrophage colony-stimulating factor (GM-CSF) has consistently induced complete marrow remission in 80% of patients with primary refractory NB. Among patients treated in first complete/very good partial remission (CR/VGPR), this combination plus 13-cis-Table 12. 3F8 amino acids residues that directly interact with GD2 based on CDOCKER and CHARMm energy minimization retinoic acid improved PFS to 51%±7% and OS to 80%±5% past 5 years. Outcome analyses have repeatedly shown the importance of FcR affinity based on gene polymorphisms in MoAb therapy of NB and other solid tumors. Improving affinities for antigen and for FcR without sacrificing specificity should improve MoAb efficacy in vitro and in vivo.

TABLE 12

3F8 amino acid residues that directly interact with GD2 based on CDOCKER and CHARMm energy minimization

| Chain | Amino Acid and Position |
|---|---|
| Light chain | Asp 91 |
|  | Tyr 92 |
| Heavy chain | Gly 33 |
|  | Trp 52 |
|  | Ala 53 |
|  | Gly 54 |
|  | Gly 55 |
|  | Ile 56 |
|  | Asn 58 |
|  | Arg 98 |
|  | His 101 |
|  | Tyr 102 |
|  | Gly 103 |
|  | Tyr 104 |

TABLE 13

Top CDR mutants from in silico mutational analysis of 3F8 interacting residues with GD2 head group

| Wildtype | Mutation | Change in interaction energy (kcal/mol) |
|---|---|---|
| HC GLY54 | ILE | −8.23 |
| HC GLY103 | LEU | −2.38 |
| HC GLY103 | TRP | −1.9 |
| HC GLY55 | THR | −1.38 |
| HC ILE56 | ARG | −0.93 |
| HC GLY54 | SER | −0.86 |

Methods:

Chimeric 3F8 (ch3F8) and humanized 3F8 (hu3F8) of the huIgG1 subclass were constructed by genetic engineering, expressed in CHO cells and purified by protein A affinity chromatography. An Fc-glycoform of hu3F8 (hu3F8n or hu3F8-MAGE1.5) that lacked fucose and N-acetylglucosamine was produced in special MAGE1.5 CHO cells. Affinities of these MoAb forms for GD2 and for FcR were compared using BIACORE T-100. Effector functions were tested using antibody-dependent cell-mediated cytotoxicity (ADCC) and complement-mediated cytotoxicity (CMC) assays, and their potencies derived from EC50 of MoAb. These strategies were applied to MoAb against other tumor antigen systems (B7-H3, HER-2, CSPG4, L1 CAM) with clinical potential.

Results:

Ch3F8 and hu3F8 maintained a Kd similar to that of m3F8, all sharing a 10-fold slower koff, when compared to 14G.2a or ch14.18, resulting in a more favorable KD and longer residence time. M3F8, ch3F8 or hu3F8 inhibited proliferation of NB cell lines in vitro, while other anti-GD2 antibodies were ineffective. In peripheral blood mononuclear cell (PBMC)-ADCC, granulocyte (PMN)-ADCC, or CMC, ch3F8 and hu3F8 were more than 10-fold stronger than ch14.18. PBMC-ADCC by hu3F8n was 10 fold more efficient than hu3F8, and >100 fold more potent than m3F8. While $^{131}$I-hu3F8 in biodistribution studies showed tumor to normal tissue ratios comparable to those of $^{131}$I-m3F8, hu3F8 demonstrated superior anti-tumor effect against NB xenografts. Although similar conclusions could be drawn for chimeric and humanized antibodies specific for other tumor antigen systems, the nature of the tumor epitope/antigen was critical in determining the efficiency of tumor kill.

Conclusions:

While koff (or $K_D$) for antigen or FcR individually improved effector functions, together their effects appeared multiplicative for anti-GD2 MoAb 3F8. Future strategies directed at improving both affinities should further extend the clinical efficacy of MoAb observed so far.

Example 13

Further Fc Modification to Improve FcR Binding

Hu3F8-IgG1-DEL with the triple mutation DEL (S239D/A330L/I332E)(Lazar et al., 2006, PNAS USA 103, 4005-10) in the heavy chain have been made with substantial increase in affinity to FcR3A and FcR2A, but also to FcR2B (see BIACORE data in table 14). However, the A/I ratio for activating versus inhibitory signals for hu3F8-IgGn is 196 for CD16-158V, compared to 30 for hu3F8-IgG1-DEL, which has been postulated to have clinical advantage (Nimmerjahn and Ravetch, Immunol Rev, 236:265-275, 2010).

TABLE 14

Relative affinity. $K_D$ was determined by flowing antibodies over recombinant FcR on CM5 chip using BIACORE T-100. All values were normalized to hu3F8-IgG1 binding on FcRIII-158F.

| Antibody form | FcRIII | | | FcRII | | |
| --- | --- | --- | --- | --- | --- | --- |
| | 158V | 158F | CD16B | 131H | 131R | CD32B |
| hu3F8-IgG1 | 2.5 | 1.0 | 0.8 | 2.1 | 1.0 | 0.1 |
| hu3F8-IgG1-DEL | 35.9 | 24.2 | 24.1 | 2.8 | 2.0 | 1.2 |
| hu3F8-IgG1n | 19.6 | 6.0 | 2.3 | 1.2 | 0.4 | 0.1 |

CD16 Mediated ADCC on Neuroblastoma LAN-1.

NK92-CD16 effector cells were added to LAN1 neuroblastoma tumor targets at effector:target ratio of 5:1 at different antibody concentrations in a 4 hour $^{51}$Cr release assay.

The increase in affinity for FcR translated into increase in ADCC potency mediated by CD16 or CD32. For ADCC mediated by CD16 (data not shown), hu3F8-IgG1-DEL and hu3F8-IgG1n were equivalent.

Complement Mediated Lysis of Neuroblastoma LAN-1.

Human complement was added to neuroblastoma LAN-1 tumor targets at a final serum complement dilution of 1:100, at increasing antibody concentrations in a 4 hour $^{51}$Cr release assay. In complement mediated lysis (CMC, data not shown), hu3F8-IgG1-DEL was not worse than hu3F8-IgG1 or hu3F8-IgG1n. When triple mutation in IgG heavy chain was combined with hu3F8-IGg1n, there was no additional improvement in ADCC.

Example 15

Arming T Cells and Effectors In Vivo

T cells or T lymphocytes are WBC that are key players in cell-mediated immunity. They can be distinguished from other lymphocyte types, such as B cells and natural killer (NK) cells by the presence of a special receptor on their cell surface called T cell receptors (TCR). They also carry a unique surface marker called CD3. T stands for thymus, which is the principal organ responsible for the maturation of T cells. Several subsets of T cells exist, each with a distinct function. T helper cells (TH cells) assist other WBC in immunologic processes, including maturation of B cells to secrete antibodies and activation of cytotoxic T cells and macrophages. They have come to be called CD4+ T cells because they carry the CD4 protein. When activated, Helper T cells divide rapidly and secrete cytokines to regulate or assist the immune response. These cells can differentiate into several subtypes (e.g. TH1, TH2, TH3, TH17, or TFH) secreting different cytokines to modulate the immune response. In some tumor models, CD4+ T cells are also sufficient in suppressing cancer growth. Although the regular activation signals come from the antigen presenting cells (APC), CD4+ T cells can become activated when their surface CD3 is cross linked by antibodies. Cytotoxic T cells (CTLs) destroy virally infected cells and tumor cells, and also responsible for transplant or graft rejection. They are called CD8+ T cells because they express the surface CD8 glycoprotein. They engage targets by recognizing antigens associated with major histocompatibility complex (MHC) class I molecules, which are absent or low on many human tumors. Memory T cells are antigen-specific T cells that persist for a long time after the virus or the tumor cells are killed. They can quickly expand to large numbers when challenged with the tumor antigen, thus empowering the immune system with "memory" against cancers. Natural killer T cells (NKT cells) are a special kind of T-cells that bridges the adaptive immune system with the innate immune system. Unlike conventional T cells that recognize peptide antigen on the MHC, NKT cells recognize glycolipid antigen presented by a molecule called CD1d. Once activated, these cells can perform functions similar to both Th and Tc cells (i.e., cytokine production and release of cytolytic/cell killing molecules). They are known to recognize and eliminate tumor cells. γδT cells (gamma delta T cells) represent a small subset of T cells that carry a TCR on their surface. A majority of T cells have a TCR composed of two glycoprotein chains called α- and β-TCR chains. However, in γδT cells, the TCR is made up of one γ-chain and one δ-chain. They represent only 5% of total T cells, but are most abundant in the gut mucosa (and named intraepithelial lymphocytes, IELs). The antigens that activate γδT cells are not known; however, γδT cells are not MHC restricted, and probably recognize whole proteins rather than peptides on MHC.

Adoptive immunotherapy trials in 1986 using lymphokine-activated killer cells (LAK) and tumor infiltrating lymphocytes (TIL) reported occasional tumor responses in patients. Donor lymphocyte infusions have shown even more successes in patients with chronic myelogenous leukemia following allogeneic stem cell transplant or in patients with post-transplant EBV-associated lymphoproliferative disease (PTLD). In solid tumors, CTL was successful in treating malignant melanoma during the lymphopenic phase created by high dose chemotherapy. Bispecific antibodies are made by fusing two hybridomas to create hybrid immunoglobulin molecules with two binding sites. The antibodies not only handcuff tumors to T-cells; they cross-link CD3 on T-cells and initiate the activation cascade. This way, TCR-based cytotoxicity is redirected to desired tumor targets bypassing MHC restrictions. Arming of polyclonally activated T cells (ATC) with anti-CD3×anti-TAA (BsAb or BiTE antibody) combines the targeting specificity of MoAb (e.g. hu3F8 where TAA is GD2) with the non-MHC-restricted perforin/granzyme mediated cytotoxicity of T cells. BsAb or BiTE can arm ex vivo expanded activated T cells before infusion into a patient. This strategy converts every ATC into a specific CTL (Thakur and Lum, 2010, Curr Opin Mol Ther 12, 340-349; Grabert et al., 2006, Clin Cancer Res 12, 569-576).

Tumors evade T cells by a number of mechanisms: low or no expression of MHC (e.g. in NB), derailing T cell signaling, decreased presentation of tumor peptides on MHC, absence of co-stimulatory molecules, and induction of regulatory T-cells that inhibit CTL and humoral responses. Since the killing carried out by BsAb or BiTE armed ATC is non-MHC-restricted, this strategy should overcome some of these tumor escape mechanisms. Tumors secrete TGF-β shifting the T-cell immune response to a Th2 type, downregulating interleukin 2 (IL-2) and IFN-γ secretion, while upregulating IL-10 and IL-6, all leading to immune suppression. T-cells redirected by BsAb or BiTE may bypass these negative effects of regulatory cytokines, since armed ATC lyse tumor targets in an IL-2 independent manner. Patients treated with BsAb or BiTE armed T cells directed at their tumors have increased levels of TNF-α and IFN-γ, which should shift the T-cells towards a Th1 response. In addition, cytotoxic T cells kill through their Fas ligand (FasL) that engage Fas receptors (CD95) on tumor cells. Unfortunately, FasL on tumors cells can also induce apoptosis of T cells. TCR stimulation through CD3 cascade protects CD8+ cells from CD95-mediated suicide. Armed ATC resist CD95-induced cell death through crosslinking of the TCR with BsAb or BiTE. The ability of T-cells to kill serially, i.e. one T-cell killing consecutive tumor targets, proliferate during the process, and move into lymphatics and soft tissues increased the chance of catching NB cells while they metastasize out of the marrow space to form tumor masses. Recent studies using BsAb or BiTE targeting human cancers have shown promise.

There is mounting evidence, particularly from analyses of patients who have received allogenic hematopoietic cell transplants, supporting the potential of T-cells to suppress or eradicate lymphomas and certain forms of leukemia (O'reilly et al., 2010, Semin Immunol 22, 162-172). However, there are no convincing data supporting a role for T-cells in the control of solid tumors in children. This is consistent with the fact that severed of these tumors either do not express inherited class I or II HLA alleles (e.g. neuroblastoma) (Raffaghello et al., 2005, Oncogene 24, 4634-4644; Wolfl et al., 2005, Cancer Immunol Immunother 54, 400-406) or express only class I alleles and at low levels (e.g. rhabdomyosarcomas) (Prados et al., 2006, Neoplasma 53, 226-231). Furthermore, expression of critical costimulatory molecules such as B7.1 and ICAM-1 is often low or undetectable. As a result, the capacity of these tumors to elicit T-cell responses is poor and the potential of effector T-cells to engage the tumors through T-cell receptor by binding tumor antigens presented by HLA alleles is limited. Furthermore, the most effective therapies currently available for neuroblastoma, rhabdomyosarcoma, Ewing's sarcoma and desmoplastic small round cell tumors employ immunosuppressive alkylating agents, particularly cyclophosphamide at doses inducing profound T-lymphopenia. Bifunctional antibodies permit the targeted engagement of T-cells and exploitation of their effector functions through HLA-non-restricted CD3-mediated activation rather than their antigen-specific HLA-restricted TCRs. Studies of certain bifunctional monoclonal antibodies specific for CD3 and a tumor antigen such as CD-19, HER-2 NEU, or CEA have demonstrated the capacity of these antibodies to link cytotoxic T-cells to tumor cells expressing the other targeted antigen (Bargou et al., 2008, Science 321, 974-977; Topp et al., 2009, Blood (ASH Annual Meeting Abstracts) 114, 840; Kiewe et al., 2006, Clin Cancer Res 12, 3085-3091; Lutterbuese et al., 2009, J Immunother 32, 341-352). Once both antibody receptors are engaged, a cytotoxic T-cell response is initiated against the tumor cells. The T-cell response involves formation of a cytotoxic synapse between the T-cell receptor and the tumor cell as well as perforin and granzyme mediated induction of tumor cell apoptosis (Offner et al., 2006, Mol Immunol 43, 763-771; Brischwein et al., 2006, Mol Immunol 43, 1129-1143). Engagement of CD3 also activates the T-cells, inducing proliferation and generation of effector cytokines that potentiate the antitumor effect (Brischwein et al., 2006, supra; Brischwein et al., 2007, J Immunother 30, 798-807). Strikingly, the activated T-cells upregulate an anti-apoptotic protein c-FLIP which protects them from the cytotoxic effects of TNF and Fas ligand generated during T-cell activation (Dreir et al., 2002, Int J Cancer 100, 690-697). As a result, the T-cell response is magnified. As a consequence, picogram levels of the bifunctional antibody can exert significant antitumor effects in vitro (Lutterbuese et al., 2009, supra; Brandl et al., 2007, Cancer Immunol Immunother 56, 1551-1563) and in vivo, as shown in preclinical animal models and particularly in the results of initial clinical trials of the CD3/CD19 bispecific in the treatment of B-cell lymphomas and ALL (Topp et al., 2009, supra; Kiewe et al., 2006, supra).

It has been hypothesized that the T-cell responses induced can also recruit naïve T-cells and stimulate the generation of tumor-specific T-cells at tumor sites (Koehne et al., 2002, Blood 99, 1730-1740). Bispecific antibodies can also be used to retarget other effector cells besides T-lymphocytes. These effector cells include NK cells, B-lymphocytes, dendritic cells, monocytes, macrophages, neutrophils, mesenchymal stem cells, neural stem cells and other stem cells to cells, tissues or organs that express GD2. When the tissue is tumor, these effector cells can be exploited to kill or to deposit proteins (e.g. cytokines, antibodies, enzymes, or toxins), radioactive isotopes for diagnosis or for therapy. When the tissue is a normal organ, the effector cells can be similarly exploited to deliver proteins or isotopes for diagnosis or for therapy.

Bispecific MoAb may be comprised of dual variable domains, with one domain having anti-3F8 variable domain and the other domain chosen from a group consisting of anti-OKT3 for retargeting T cells for tumor cytotoxicity, or DOTA-metal, C8.2.5 for multistep pretargeting, or Clone 35, CD137, for ADCC with anti-41BB-scFv as agonist, or with CD137, 41BBL for ADC with 41 BBL as agonist. A N297A mutation in the CH2 domain results in aglycosylation leading to no FcR or Clq binding. The amino acid sequence of (hu3F8-LC)-(huOKT3-scFv) where the huOKT3-scFv is disulfide stabilized is shown in SEQ ID NO:23. The amino acid sequence of hu3F8-LC)-(C8.2.5-scFv) (based on Orcutt et al., 2010, Protein Eng Design and Selection 23, 221) with C8.2.5-scFv disulfide stabilized is shown in SEQ ID NO:24.

Bispecific antibody (anti-GD2 and anti-DOTA) can be used in a first step of a multistep pretargeting, followed by blood clearance using DOTA(metal)-Dextran as clearing agent, with a third step introducing DOTA(metal)-conjugated therapeutics such as DOTA(metal)-radioactive metal, DOTA (metal)-nanoparticles, DOTA(metal-liposomes, DOTA (metal)-drugs, DOTA(metal)-DNA, DOTA(metal)-RNA, and DOTA (metal)-toxins. Since C8.2.5 has different affinities for each type of DOTA-metal compels, the affinity of the pretargeted C8.2.5 for the clearing agent and the DOTA-ligand can be precisely controlled.

The amino acid sequence of 3F8, hu3F8 and its variants, can be used to construct chimeric antigen receptor (CAR) as was previously shown for other anti-GD2 antibodies (Krause et al., 1998, J Exp Med 188, 619-626). The CAR strategy of retargeting immune effector cells is independent of the MHC-peptide-TCR interaction and allows cells to react against a large variety of cell surface antigens (Davies and Maher, 2010, Achivum immunologiae et therapiae experimentalis 58, 165-178). Several methods have been used in the design of CARs, with most of them employing the antigen binding domain of a monoclonal antibody in the form of a single-chain variable fragment (scFv) for antigen recognition. The initial T cell activating receptors originated from studies which allowed researchers to elucidate the role of the CD3ζ chain (Irving and Weiss, 1991, Cell 64, 891-901; Romeo et al., 1992, Cell 68, 889-897). In subsequent studies, scFvs of interest were fused to the CD3ζ chain (Eshhar et al., 1993, PNAS USA 90, 720-724) or FcεRIγ (Weijtens et al., 1996, J Immunol 157, 836-843), and both were found to be sufficient for T cell activation. While this laid the blueprint for CAR construction, the incorporation of costimulatory molecules came about after it was found that first generation CARs were able to induce T cell proliferation only up to 2-3 cell divisions, followed rapidly by cell death (Gong et al., 1999, Neoplasia 1, 123-127). By expressing CD80 on the target tumor cell, researchers were able to show that CAR expressing cells could be restimulated, leading to further increases in T cell numbers. The first CARs which incorporated the CD28 costimulatory molecule alongside the CD3ζ chain showed vast improvements over those which expressed the CD3ζ chain alone (Krause et al., 1998, supra; Haynes et al., 2002, Blood 100, 3155-3163; Maher et al., 2002, Nature Biotech 20, 70-75); this included an absolute increase in T cell numbers as well as an increase in IL-2 production. Since then, several other groups began to use other costimulatory molecules, either in combination with CD3ζ alone or with both CD3ζ and CD28. These additional signaling molecules include 4-1BB (Wang et al., 2007, Human Gene Ther 18, 712-725; Brentjens et al., 2007, Clin Cncer Res 13, 5426-5432; Imai et al., 2004, Leukemia 18, 676-684; Finney et al., 2004, J Immunol 172, 104-113), DAP10 (Brentjens et al., 2007, supra), 0X40 (Brentjens et al., 2007, supra; Finney et al., 2004, supra; Wilkie et al., 2008, J Immunol 180, 4901-4909; Nguyen and Geiger, 2003, Gene Therapy 10, 594-604; Pule et al., 2005, Mol Ther 12, 933-941) and ICOS (Finney et al., 2004, supra), and have been applied in the context of T cells as well as NK cells (Daldrup-Link et al., 2005, Eropean radiology 15, 4-13; Imai and Campana, 2004, J Biol Reg Homeostatic Ag 18, 62-71; Roberts et al., 1998, J Immunol 375-384; Kruschinski et al., 2008, PNAS USA 105, 17481-17486; Pegram et al., 2008, J Immunol 181, 3449-3455). While first generation CARs are the only ones which have been tested in the clinic up to this point, both in vitro and in vivo comparisons have demonstrated a clear superiority with second and third generation CARs (Haynes et al., 2002, supra; Brentjens et al., 2007, supra; Teng et al., 2004, Human Gene Ther 15, 699-708; Haynes et al., 2002, J Immunol 169, 5780-5786; Kowolik et al., 2006, Cancer Res 66, 10995-11004; Loskog et al., 2006, Leukemia 20, 1819-1928; Moeller et al., 2004, Cancer Gene Therapy 11, 371-379; Vera et al., 2006, Blood 108, 3890-3897).

Currently, most researchers use bulk human peripheral T cells, however others have recently began to use EBV-specific T cells (Rossig et al., 2002, Blood 99, 2009-2016), lymphoid progenitor cells (Zakrzewski et al., 2006, Nature Med 12, 1039-1047; Zakrzewski et al., 2008, Nature Biotech 26, 453-461), and unfractionated bone marrow cells (Papapetrou et al., 2009, J clin Invest 119, 157-168; Wang et al., 1998, Nature Med 4, 168-172). Killer leukemia cell lines (e.g. NK92, NK92MI, KHYG-1) that are cytolytic and easy to culture can also provide a continuous supply of CAR expressing effector cells for pre-clinical and clinical testing. NK92MI is a human NK cell line derived from a non-Hodgkin's lymphoma and transduced with human IL-2 cDNA; previous studies have demonstrated its strong cytotoxic abilities in mouse models (Tam et al., 1999, J Hematol 8, 281-290; Korbelik and Sun, 2001, Inter J Cancer 93, 269-274). In addition, NK92 cells have also been used in the clinical setting and proven safe after a number of Phase I studies in patients with renal cell carcinoma and melanoma (Arai et al., 2008, Cytotherapy 10, 625-632). Because of their ease of maintenance in vitro and relatively short doubling-times, these cells are ideal effectors for various cytotoxicity assays to test a variety of targeting approaches. While studies using the original IL-2-dependent NK92 cell line have shown minimal toxicities in both mice and humans, the IL-2-transduced NK92MI cells may have a greater leukemogenic potential. One method by which researchers try and avoid leukemogenesis in SCID mice using NK92 cells is by irradiating the effectors with 3000 cGy before inoculation. In phase I clinical trials, this is sufficient in preventing NK92MI cells from proliferating uncontrollably inside of the immunocompromised patient. An alternative safety mechanism is that which involves the employment of suicide genes. One common example is the use of the herpesvirus thymidine kinase gene, which works by killing a cell which expresses the gene by administration of acyclovir or ganciclovir (Helene et al., 1997, J Immunol 5079-5082).

What is claimed is:

1. A humanized or chimeric antibody or fragment thereof capable of binding to GD2, wherein the antibody or fragment thereof comprises any of the following:
   (i) a variable heavy chain domain of SEQ ID NO: 1 and a variable light chain domain of SEQ ID NO:2;
   (ii) a variable heavy chain domain of SEQ ID NO:3 and a variable light chain domain of SEQ ID NO:2;
   (iii) a variable heavy chain domain of SEQ ID NO:4 and a variable light chain domain of SEQ ID NO:5;
   (iv) a variable heavy chain domain of SEQ ID NO:6 and a variable light chain domain of SEQ ID NO:7;
   (v) a variable heavy chain domain of SEQ ID NO:8 and a variable light chain domain of SEQ ID NO:5;
   (vi) a variable heavy chain domain of SEQ ID NO:9 and a variable light chain domain of SEQ ID NO: 10; and
   (vii) a variable heavy chain domain of SEQ ID NO:6 and a variable light chain domain of SEQ ID NO: 5.

2. The humanized or chimeric antibody or fragment of claim 1, wherein the antibody or fragment is glycosylated with terminal mannose, N-acetylglucose or glucose, but no fucose.

3. A pharmaceutical composition comprising the humanized or chimeric antibody or fragment thereof of claim 1, and further comprising a pharmaceutically acceptable carrier or diluent.

4. The humanized or chimeric antibody or fragment thereof of claim 1, wherein the antibody or fragment is conjugated to a cytotoxic agent.

5. A bispecific antibody having first and second antigen binding sites, one of which comprises antigen binding sequences of a light chain and a heavy chain of a humanized 3F8 antibody.

6. The bispecific antibody of claim 5 wherein the second antigen binding site is selected from the group consisting of scFv, scFab, Fab, and Fv.

7. The bispecific antibody of claim 5 wherein the second antigen binding site is associated with an immunological cell chosen from the group consisting of T-lymphocytes, NK cell, B-lymphocytes, dendritic cells, monocytes, macrophages, neutrophils, mesenchymal stem cells, and neural stem cells.

8. The bispecific antibody of claim 5 wherein the second antigen binding site is specific for CD3 or for a DOTA (metal).

9. The bispecific antibody of claim 6, further comprising a peptide of SEQ ID NO:23 that includes the second antigen binding site.

10. The bispecific antibody of claim 6, further comprising a peptide of SEQ ID NO:24 that includes the second antigen binding site.

11. A pharmaceutical composition comprising the bispecific antibody of claim 5, and further comprising a pharmaceutically acceptable carrier or diluent.

12. A chimeric antigen receptor comprising an antigen binding domain of a humanized or chimeric antibody or fragment of claim 1.

13. The chimeric antigen receptor of claim 12, wherein the antigen binding domain is a scFv.

14. The chimeric antigen receptor of claim 13, expressed by an immune effector cell.

15. A bispecific T-cell engaging monoclonal antibody comprising a first binding site comprising scFv from hu3F8 monoclonal antibody, and a second binding site binding to a T-cell.

16. A pharmaceutical composition comprising the antibody or fragment thereof of claim 2, and further comprising a pharmaceutically acceptable carrier or diluent.

17. A pharmaceutical composition comprising the bispecific antibody of claim 6, and further comprising a pharmaceutically acceptable carrier or diluent.

18. A pharmaceutical composition comprising the bispecific antibody of claim 7, and further comprising a pharmaceutically acceptable carrier or diluent.

19. A pharmaceutical composition comprising the bispecific antibody of claim 8, and further comprising a pharmaceutically acceptable carrier or diluent.

20. A pharmaceutical composition comprising the bispecific antibody of claim 9, and further comprising a pharmaceutically acceptable carrier or diluent.

21. A pharmaceutical composition comprising the bispecific antibody of claim 10, and further comprising a pharmaceutically acceptable carrier or diluent.

22. A pharmaceutical composition comprising the antibody or fragment thereof of claim 4, and further comprising a pharmaceutically acceptable carrier or diluent.

23. The humanized or chimeric antibody or fragment thereof of claim 1, wherein the antibody or fragment comprises a variable heavy chain domain of SEQ ID NO: 1 and a variable light chain domain of SEQ ID NO:2.

24. The humanized or chimeric antibody or fragment thereof of claim 1, wherein the antibody or fragment comprises a variable heavy chain domain of SEQ ID NO:3 and a variable light chain domain of SEQ ID NO:2.

25. The humanized or chimeric antibody or fragment thereof of claim 1, wherein the antibody or fragment comprises a variable heavy chain domain of SEQ ID NO:4 and a variable light chain domain of SEQ ID NO:5.

26. The humanized or chimeric antibody or fragment thereof of claim 1, wherein the antibody or fragment comprises a variable heavy chain domain of SEQ ID NO:6 and a variable light chain domain of SEQ ID NO:7.

27. The humanized or chimeric antibody or fragment thereof of claim 1, wherein the antibody or fragment comprises a variable heavy chain domain of SEQ ID NO:8 and a variable light chain domain of SEQ ID NO:5.

28. The humanized or chimeric antibody or fragment thereof of claim 1, wherein the antibody or fragment comprises a variable heavy chain domain of SEQ ID NO:9 and a variable light chain domain of SEQ ID NO: 10.

29. The humanized or chimeric antibody or fragment thereof of claim 1, wherein the antibody or fragment comprises a variable heavy chain domain of SEQ ID NO:6 and a variable light chain domain of SEQ ID NO: 5.

30. The humanized or chimeric antibody or fragment thereof of claim 1, wherein the humanized or chimeric antibody comprises a variant Fc region.

31. The humanized or chimeric antibody or fragment thereof of claim 30, wherein the variant Fc region comprises a substitution of S239D, A330L and 1332E.

32. The humanized or chimeric antibody or fragment thereof of claim 30, wherein the variant Fc region comprises a N297A substitution.

33. The humanized or chimeric antibody or fragment thereof of claim 2, wherein the humanized or chimeric antibody comprises a variant Fc region.

34. The humanized or chimeric antibody or fragment thereof of claim 33, wherein the variant Fc region comprises a substitution of S239D, A330L and 1332E.

35. The humanized or chimeric antibody or fragment thereof of claim 33, wherein the variant Fc region comprises a N297A substitution.

* * * * *

UNITED STATES PATENT AND TRADEMARK OFFICE
CERTIFICATE OF CORRECTION

PATENT NO. : 9,315,585 B2  
APPLICATION NO. : 13/702319  
DATED : April 19, 2016  
INVENTOR(S) : Nai-Kong Cheung, Mahiuddin Ahmed and Hong Xu Page 1 of 1

It is certified that error appears in the above-identified patent and that said Letters Patent is hereby corrected as shown below:

In the claims

Column 122, line 16 (claim 31, line 3) please replace the phrase "and 1332E" with "and I332E".

Column 122, line 25 (claim 34, line 3) please replace the phrase "and 1332E" with "and I332E".

Signed and Sealed this
Twenty-eighth Day of June, 2016

Michelle K. Lee
*Director of the United States Patent and Trademark Office*

UNITED STATES PATENT AND TRADEMARK OFFICE
CERTIFICATE OF CORRECTION

PATENT NO. : 9,315,585 B2  
APPLICATION NO. : 13/702319  
DATED : April 19, 2016  
INVENTOR(S) : Nai-Kong Cheung Page 1 of 1

It is certified that error appears in the above-identified patent and that said Letters Patent is hereby corrected as shown below:

In column 1, beginning at line 1, please insert:

--GOVERNMENT SUPPORT  
This invention was made with government support under grant numbers CA161978 awarded by National Institutes of Health. The government has certain rights in the invention.--

Signed and Sealed this  
Twenty-second Day of November, 2016

Michelle K. Lee  
*Director of the United States Patent and Trademark Office*

UNITED STATES PATENT AND TRADEMARK OFFICE

(12)       CERTIFICATE EXTENDING PATENT TERM
UNDER 35 U.S.C. § 156

| | | | |
|---|---|---|---|
| (68) | PATENT NO. | : | 9,315,585 |
| (45) | ISSUED | : | April 19, 2016 |
| (75) | INVENTOR | : | Nai-Kong Cheung et al. |
| (73) | PATENT OWNER | : | Memorial Sloan Kettering Cancer Center |
| (95) | PRODUCT | : | DANYELZA® (naxitamab-gqgk) |

This is to certify that an application under 35 U.S.C. § 156 has been filed in the United States Patent and Trademark Office, requesting extension of the term of U.S. Patent No. 9,315,585 based upon the regulatory review of the product DANYELZA® (naxitamab-gqgk) by the Food and Drug Administration. According to United States Patent and Trademark Office records, the original expiration date of the patent as of the date of issuance of this certificate is June 20, 2031. Because it appears that the requirements of the law have been met, this certificate extends the term of the patent for the period of

(94)                             961 days subject to the payment of maintenance fees as provided by law, with all rights pertaining thereto as provided by 35 U.S.C. § 156.

I have caused the seal of the United States Patent and Trademark Office to be affixed this 12th day of August 2025.

Coke Morgan Stewart
Acting Under Secretary of Commerce for Intellectual Property and Acting Director of the United States Patent and Trademark Office